United States Patent
Kumanogoh et al.

(10) Patent No.: US 10,688,178 B2
(45) Date of Patent: Jun. 23, 2020

(54) ANTIPLEXIN A1 AGONIST ANTIBODY

(71) Applicants: OSAKA UNIVERSITY, Osaka (JP); CHUGAI SEIYAKU KABUSHIKI KAISHA, Tokyo (JP)

(72) Inventors: Atsushi Kumanogoh, Osaka (JP); Ryusuke Omiya, Shizuoka (JP); Hiroyuki Tsunoda, Shizuoka (JP); Takeshi Baba, Shizuoka (JP); Sachiyo Suzuki, Shizuoka (JP); Yuri Teranishi, Shizuoka (JP)

(73) Assignees: Osaka University, Osaka (JP); Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/741,225

(22) PCT Filed: Jun. 30, 2016

(86) PCT No.: PCT/JP2016/069439
§ 371 (c)(1),
(2) Date: Dec. 29, 2017

(87) PCT Pub. No.: WO2017/002919
PCT Pub. Date: Jan. 5, 2017

(65) Prior Publication Data
US 2018/0193451 A1    Jul. 12, 2018

(30) Foreign Application Priority Data

Jun. 30, 2015  (JP) .................. 2015-132067

(51) Int. Cl.
| C07K 16/28 | (2006.01) |
| A61K 39/395 | (2006.01) |
| C07K 16/46 | (2006.01) |
| C12N 15/09 | (2006.01) |

(52) U.S. Cl.
CPC ............ *A61K 39/395* (2013.01); *C07K 16/28* (2013.01); *C07K 16/2863* (2013.01); *C07K 16/46* (2013.01); *C12N 15/09* (2013.01); *C07K 2317/21* (2013.01); *C07K 2317/24* (2013.01); *C07K 2317/33* (2013.01); *C07K 2317/54* (2013.01); *C07K 2317/55* (2013.01); *C07K 2317/622* (2013.01); *C07K 2317/75* (2013.01); *C07K 2317/76* (2013.01)

(58) Field of Classification Search
CPC ..................................... C07K 16/28
USPC ..................................... 424/136.1
See application file for complete search history.

(56) References Cited

U.S. PATENT DOCUMENTS

| 8,871,205 B2 | 10/2014 | Ting et al. |
| 2005/0118168 A1 | 6/2005 | Figdor et al. |
| 2007/0167607 A1 | 7/2007 | Steinkasserer et al. |
| 2008/0025913 A1 | 1/2008 | Bowdish et al. |
| 2008/0045443 A1* | 2/2008 | Kikutani ............... C07K 16/18 514/16.7 |
| 2008/0213268 A1 | 9/2008 | Watts et al. |
| 2012/0322085 A1 | 12/2012 | Kumanogoh |
| 2013/0115214 A1 | 5/2013 | Watts et al. |
| 2013/0149238 A1 | 6/2013 | Kavlie et al. |
| 2015/0368327 A1 | 12/2015 | Goshima et al. |

FOREIGN PATENT DOCUMENTS

| EP | 1739092 A1 | 1/2007 |
| JP | 2000159670 A | 6/2000 |
| JP | 2003502283 A | 1/2003 |
| JP | 2008504222 A | 2/2006 |
| JP | 2006523432 A | 10/2006 |
| JP | 2009514972 A | 4/2009 |
| WO | WO-2011055550 A1 | 5/2011 |
| WO | WO-2014123186 A1 | 8/2014 |

OTHER PUBLICATIONS

Bielenberg et al (Am J Path, 2012, 181(2): 548-559).*
Plexin A1 Antibody #3813 data sheet (Cell signaling Technology, 2015).*
Amano, M., et al., "Phosphorylation and Activation of Myosin by Rho-associated Kinase (Rho-kinase)," J Biol Chem 271(34):20246-20249 (1996).
Flinn, H. M., and Ridley, A. J., "Rho stimulates tyrosine phosphorylation of focal adhesion kinase, p130 and paxillin," J Cell Science 109:1133-1141 (1996).
Sengoku, K., et al., "Effects of tacrolimus ointment on type I (immediate and late) and IV (delayed) cutaneous allergic reactions in mice," Folia Pharmacol Jpn 112:221-232 (1998)(Abstract).
Tamagnone, L. and Comoglio, P. M., "Signalling by semaphoring receptors: cell guidance and beyond," Trends in Cell Biology 10:377-383 (2000).
Tordjman, R., et al., "A neuronal receptor, neuropilin-I, is essential for the initiation of the primary immune response," Nature Immunology 3(5):477-482 (2002).
Wong, A. W., et al., "CIITA-regulated plexin-A1 affects T-cell-dendritic cell interactions," Nature Immunology 4(9):891-898 (2003).
Ohl, L., et al., "CCR7 Governs Skin Dendritic Cell Migration under Inflammatory and Steady-State Conditions," Immunity 21:279-288 (2004).
Eun, S-Y., et al., "Cutting Edge: Rho Activation and Actin Polarization Are Dependent on Plexin-A1 in Dendritic Cells," J Immunol 177:4271-4275 (2006).
Takegahara, N., et al., "Plexin-A1 and its interaction with DAP12 in immune responses and bone homeostasis," Nat Cell Biol 8(6):615-622 (2006).
Lepelletier, Y., et al., "Immunosuppressive role of semaphorin-3A on T cell proliferation is mediated by inhibition of actin cytoskeleton reorganization," Eur J Immunol 36:1782-1793 (2006).

(Continued)

*Primary Examiner* — Sean E Aeder
(74) *Attorney, Agent, or Firm* — Nixon & Vanderhye P.C.

(57) ABSTRACT

Provided is a novel anti-Plexin-A1 agonist antibody that promotes dendritic cell contraction. Also provided is a pharmaceutical composition comprising such an antibody and a pharmaceutically acceptable carrier.

22 Claims, 10 Drawing Sheets

Specification includes a Sequence Listing.

(56) References Cited

OTHER PUBLICATIONS

Johnson, L. A., et al., "An inflammation-induced mechanism for leukocyte transmigration across lymphatic vessel endothelium," J Exp Med 203(12):2763-2777 (2006).

Mann, F., et al., "Semaphorins in development and adult brain: Implications for neurological diseases," Progress in Neurobiology 82:57-79 (2007).

Anonymous, "Treatments for Type IV Hypersensitivity," RightDiagnosis.com, http://www.rightdiagnosis.com/t/type_iv_hypersensitivity/treatments.htm (2016).

Matsunaga, Y. and Takagi, J., "Three-dimensional conformation of Semaphorin-related molecular groups," Experimental Medicine 31(4):523-531 (with English translation)(2013).

Suzuki, K., et al., "Structure of the Plexin Ectodomain Bound by Semaphorin-Mimicking Antibodies," PLOS ONE 11(6):e0156719 (2016).

Kolodkin, A. L., et al., "The semaphorin Genes Encode a Family Transmembrane and Secreted Growth Cone Guidance Molecules," Cell 75:1389-1399 (1993).

Tessier-Lavigne, M. and Goodman, C. S., "The Molecular Biology of Axon Guidance," Science 274:1123-1133 (1996).

Pasterkamp, R. J., and Kolodkin, A. L., "Semaphorin junction: making tracks toward neural connectivity," Curr Opin Neurobiol 13:79-89 (2003).

Janssen, B. J. C., et al., "Neuropilins lock secreted semaphorins onto plexins in a ternary signaling complex," Nat Struct Mol Biol 19(12):1293-1299 (2012).

Kou, K., et al., "Decreased Expression of Semaphorin-3A, a Neurite-collapsing Factor, is Associated With Itch in Psoriatic Skin," Acta Derm Venereol 92:521-528 (2012).

Tominaga, M., et al., "Psoralen-ultraviolet A theraphy alters epidermal Sema3A and NGF levels and modulates epidermal innervation in atopic dermatitis," J Dermatol Sci 55:40-46 (2009).

Yamaguchi, J., et al., "Semaphorin3A Alleviates Skin Lesions and Scratching Behavior in NC/Nga Mice, an Atopic Dermatitis Model," J Investigative Dermatology 128:2842-2849 (2008).

Negi, O., et al., "Topically applied semaphorin 3A ointment inhibits scratching behavior and improves skin inflammation in NC/Nga mice with atopic dermatitis," J Dermatol Sci 66:37-43 (2012).

Sawaki, H., et al., "Intranasal Administration of Semaphorin-3A Alleviates Sneezing and Nasal Rubbing in a Murine Model of Allergic Rhinitis," J Pharmacol Sci 117:34-44 (2011).

Hayashi, M., et al., "Osteoprotection by semaphoring 3A," Nature 485:69-74 (2012).

Fukuda, T., et al., "Sema3A regulates bone-mass accrual through sensory innervations," Nature 497:490-493 (2013).

Catalano, A., "The Neuroimmune Semaphorin-3A Reduces Inflammation and Progression of Experimental Autoimmune Arthritis," J Immunol 185:6373-6383 (2010).

Vadasz, Z., et al., "Semaphorin 3A is a marker for disease activity and a potential immunoregulator in systemic lupus erythematosus," Arth Res Ther 14:R146 (2012).

Chakraborty, G., et al., "Semaphorin 3A Suppresses Tumor Growth and Metastasis in Mice Melanoma Model," PLOS ONE 7(3):e33633 (2012).

Yamashita, N., et al., "Anti-Semaphorin 3A neutralization monoclonal antibody prevents sepsis development in lipopolysaccharide-treated mice," Intl Immunol 27(9): 459-466 (2015).

Kaila, N., et al., "Diazine Indole Acetic Acids as Potent, Selective, and Orally Bioavailable Antagonists of Chemoattractant Receptor Homologous Molecule Expressed on Th2 Cells (CRTH2) for the Treatment of Allergic Inflammatory Diseases," J Med Chem 55:5088-5109 (2012).

Petersen, T. K., "In vivo Pharmacological Disease Models for Psoriasis and Atopic Dermatitis in Drug Discovery," Basic & Clinical Pharmacology & Toxicology 99:104-115 (2006).

Engeman, T. M., et al., "Inhibition of Functional T Cell Priming and Contact Hypersensitivity Responses by Treatment with Anti-Secondary Lymphoid Chemokine Antibody During Hapten Sensitization," J Immunol 164:5207-5214 (2000).

Lee, J., et al., "Anti-inflammatory and barrier protecting effect of *Lithospermum erythrorhizon* extracts in chronic oxazolone-induced murine atopic dermatitis," J Dermatol Sci 56:58-73 (2009).

International Search Report of International PCT Application No. PCT/JP2016/069439 dated Aug. 9, 2016, 7 pages.

Wu, H., et al., "Humanization of a Murine Monoclonal Antibody by Simultaneous Optimization of Framework and CDR Residues," J Mol Biol 294:151-162 (1999).

Maccallum, R. M., et al., "Antibody-antigen Interactions: Contact Analysis and Binding Site Topography," J Mol Biol 262:732-745 (1998).

Casset, F., et al., "A peptide mimetic of an anti-CD4 monoclonal antibody by rational design," Biochemical and Biophysical Research Communications 307:198-205 (2003).

Skolnick, J. and Fetrow, J. S., "From genes to protein structure and function: novel applications of computational approaches in the genomic era," Trends in Biotechnology 18:34-39 (2000).

Vajdos, F. F., et al., "Comprehensive Functional Maps of the Antigen-binding Site of an Anti-ErbB2 Antibody Obtained with Shotgun Scanning Mutagenesis," J Mol Biol 320:415-428 (2002).

Final Office Action, dated Mar. 9, 2018 in U.S. Appl. No. 14/258,617, Kumanogoh, A., filed Apr. 22, 2014.

Extended European Search Report dated Jan. 3, 2019 in European Patent Application No. 16818027.1.

Hota, P. K. and Buck, M., "Plexin structures are coming: opportunities for multilevel investigations of semaphorin guidance receptors, their cell signaling mechanisms, and functions," Cell Mol Life Sci., 69:3765-3805 (2012).

Kumanogoh, A. and Kikutani, H., "Immunological functions of the neuropilins and plexins as receptors for semaphorins," Nature Rev Immunol., 13:802-814 (2013).

Montolio, M., et al., "A Semaphorin 3A Inhibitor Blocks Axonal Chemorepulsion and Enhances Axon Regeneration," Chem & Biol., 16:691-701 (2009).

Communication pursuant to Article 94(3) EPC dated Jan. 10, 2019 in European Patent Application No. 17189095.7.

Sarris, M., et al., "Neuropilin-1 Expression on Regulatory T Cells Enhances Their Interactions with Dendritic Cells during Antigen Recognition," Immunity, 28:402-413 (2008).

Takamatsu, H. and Kumanogoh, A., "Diverse roles for semaphorin—plexin signaling in the immune system," Trends in Immunology, 33(3):127-135 (2012).

\* cited by examiner

FIG. 11

```
mPlexinA1   1 AISSPPAGLGPQ AFR  VA--S  LI    EQ     CA  I       LL    I     DN K    P  S     78
mPlexinA2   1 --------TTGM  QYS   SENR  TFN   RR    V GA  N V     N   QV  K C   DNK   T PL V      72 mPlexinA1  79 PH    S       L       A   LC  A     QF    D       H       R  REA     L LIAGPPGQGQ    158
mPlexinA2  73 SEV   L   V  M  T   SENR  A  SLY  M KL    D D     P H    T SGQ NKT    YGVIV--RSEGED  150 mPlexinA1 159    P      E       R MANE DAD  FGFVYQDE    QL    SKFPA  I      E       L D 238
mPlexinA2 151    AV     D    SS    PRD SSA  LYELES      LIKTPRD ALVS   N  G SS     I   PE 230 mPlexinA1 239  -QLSPDA      G        N  N     R   CR  S  N LV  A  SN  CA   KQLGLAP       Q 317
mPlexinA2 231  PDGMAINS  DL  Y S LV  K  E  N   GTPR   R  V     LA N  AR  L AQAFNISS    AI GK 310 mPlexinA1 318   NRVK  KE    TL   K R   L S R S     EN LG  INS LQ   D G    QL G TVT   397
mPlexinA2 311    QYHM   D A   PI A  NLQ KER   HQKN E  N L GKDVQSTKA V  D N   I I QPI GGSTPV  390 mPlexinA1 398 TP  VDKE              RI    S  R RIR  LV LAN   RPALA  S   AQEGN   DLVI  RQ    476
mPlexinA2 391 LT  YTTS    T V    V N YS V S   G KLK RA --GP     --GVQ   S FKL G     MA     QL      467 mPlexinA1 477 T         (SEQ ID NO:52)                                              488
mPlexinA2 468 S         (SEQ ID NO:53)                                              479
```

FIG. 12

```
mPlexinA1    1 AISSPPAGLGPQPAFRTFVASDWGLTHLVVHEQTGEVYVGAVNRIYKLSGNLTLLRAHVT  60
hPlexinA1    1 EAGL.R..G.S..P....S.........................................  60 mPlexinA1   61 GPVEDNEKCYPPPSVQSCPHGLGSTDNVNKLLLLDYAANRLLACGSASQGICQFLRLDDL 120
hPlexinA1   61 ............................................................ 120 mPlexinA1  121 FKLGEPHHRKEHYLSSVREAGSMAGVLIAGPPGQGQAKLFVGTPIDGKSEYFPTLSSRRL 180
hPlexinA1  121 .....................Q...................................... 180 mPlexinA1  181 MANEEDADMFGFVYQDEFVSSQLKIFSDTLSKFPAFDIYYVYSFRSEQFVYYLTLQLDTQ 240
hPlexinA1  181 ............................................................ 240 mPlexinA1  241 LTSPDAAGEHFFTSKIVRLCVNDPKFYSYVEFPIGCEQAGVEYRLVQDAYLSRPGQALAK 300
hPlexinA1  241 .......................D.........................R...H 300 mPlexinA1  301 QLGLAEDEEVLFTVFAQGQKNRVKPPKESALCLFTLRAIKEKIKERIQSCYRGEGKLSLP 360
hPlexinA1  301 ......D..................................................... 360 mPlexinA1  361 WLLNKELGCINSPLQIDDDFCGQDFNQPLGGTVTIEGTPLFVDKEDGLTAVAAYDYQGRT 420
hPlexinA1  361 ...............................D...........R... 420 mPlexinA1  421 VVFAGTRSGRIRKILVDLANPSGRPALAYESVVAQEGNPILRDLVLSPNRQYLYAMTEKQ 480
hPlexinA1  421 ................S..G.....................S...........R........ 480 mPlexinA1  481 VTQVPVES    (SEQ ID NO:52)                                   488
hPlexinA1  481 ..R.....    (SEQ ID NO:3)                                    488
```

ANTIPLEXIN A1 AGONIST ANTIBODY

CROSS-REFERENCE TO RELATED APPLICATIONS

This application is a U.S. National Phase of PCT Application No. PCT/JP2016/069439, filed Jun. 30, 2016, which claims the benefit of Japanese Patent Application No. 2015-132067, filed Jun. 30, 2015, each of which is incorporated herein by reference.

REFERENCE TO SEQUENCE LISTING SUBMITTED ELECTRONICALLY

The content of the electronically submitted sequence listing (Name: 6663_0024 Sequence_Listing.txt; Size: 177 kilobytes; and Date of Creation: Dec. 29, 2017) filed with the application is incorporated herein by reference in its entirety.

TECHNICAL FIELD

The present invention relates to an anti-Plexin-A1 agonist antibody and use thereof.

BACKGROUND ART

Semaphorins were discovered in the early 1990's as repulsive molecules for neuronal growth cones (Non Patent Literatures 1 and 2). More than 20 members of semaphorins have been identified to date, and the semaphorin family is characterized by sharing a conserved region consisting of about 500 amino acids, referred to as the Sema domain. These semaphorins are classified into eight sub-classes (Sema 1-7, V) on the basis of structural difference at the C-terminus following the Sema domain.

Plexins (Plexin-A1/A2/A3/A4, Plexin-B1/B2/B3, Plexin-C1, and Plexin-D1) and neuropilins (Nrp-1 and Nrp-2) are known as major receptors that contribute to the semaphorin activity. Semaphorins are known to also bind to integrins, CD72, and Tim-2 (Non Patent Literature 3). Furthermore, the semaphorin receptors, plexins, are known to associate with various co-receptors such as VEGFR-2, c-Met, and Trem2/DAP12, and construct possibly reflect diverse functions of the semaphorins. Indeed, the semaphorins have diverse biological activities such as angiogenesis/vasculogenesis, cancer metastasis/invasion, bone metabolism regulation, retinal homeostasis, and immune regulation, and the involvement of the semaphorins in various diseases such as allergic diseases or autoimmune diseases, metabolic bone diseases, neurodegenerative diseases, retinitis pigmentosa, sudden death from cardiac causes, and cancer metastasis/invasion has been successively reported in the past several years (Non Patent Literature 3). In connection with biological activities of the semaphorins, active research is currently ongoing with a view towards developing diagnostic/therapeutic methods for human diseases.

Plexin-A1 is a receptor for class III and class VI semaphorins. Plexin-A1 has been reported to form receptors together with VEGF receptor and Off-Track during chick heart morphogenesis, and also act as a receptor for neuronal repulsive factors by forming a receptor for class III semaphorins together with Nrp-1. Furthermore, Plexin-A1 has been reported to also act as a receptor for class VI semaphorins, Sema6C and Sema6D, and be involved in axon guidance or cardiac organogenesis.

It has been reported that suppression of Plexin-A1 expression by shRNA in mouse dendritic cells, for example, leads to attenuated non-autoimmune T-cell immunity in vivo or in vitro (Non Patent Literature 4). Plexin-A1 signal analysis in dendritic cells and osteoclasts has also confirmed that Plexin-A1 forms heteroreceptors with Trem-2 and DAP-12 in these cells. It has also been shown that recombinant soluble Sema6D protein stimulation promotes the expression of inflammatory cytokines such as IL-12 from dendritic cells and osteoclast differentiation from precursor cells, and that while Sema6D binds to wild-type dendritic cells, it hardly binds to dendritic cells from Plexin-A1-deficient mice. It has been reported that T-cell immune responses are significantly weaker in Plexin-A1-deficient mice, which spontaneously develops osteopetrosis-like symptoms caused by abnormal osteoclast differentiation (Non Patent Literature 5). Plexin-A1 inhibition by shRNA in mouse dendritic cells has shown that Plexin-A1 controls actin cytoskeleton localization in the immune synapses of dendritic cells and T cells via activation of signal transduction factor Rho (Non Patent Literature 6).

Furthermore, it has been reported that Plexin-A1 is involved in the migration of dendritic cells to the lymph nodes and in antigen-specific T-cell responses. It has also been reported that the expression of Sema3A, rather than Sema6C or Sema6D, is required for migration of dendritic cells as they pass through the endothelial cells of the lymphatic vessels, and Sema3A stimulates myosin-II activity and induce actomyosin contraction (Patent Literature 1).

Furthermore, in connection with Plexin-A2, which is another molecule belonging to the Plexin-A family, a low-resolution (7.0 A) structure of a triple complex, "Sema3A-Plexin-A2-Nrp-1", has been disclosed. Although the binding between Sema3A and Plexin-A2 is too weak to be detected, it has been reported that an interaction between Sema3A and Plexin-A2 was detected in the presence of Nrp-1, even though it was far too weak for the expression of biological activity of Sema3A (Non Patent Document 7). The elucidation of this complex, however, requires further detailed study, because the resolution of this structure is extremely low, and a partial-length protein rather than a full-length protein was used. Non Patent Literature 8, on the other hand, introduces the structure of a triplet complex, "Sema3A-Plexin-A1-Nrp-1", citing Non Patent Literature 7 described above. Non Patent Literature 7, however, fails to disclose the structure of the triplet complex "Sema3A-Plexin-A1-Nrp-1".

Sema3A has been suggested to exhibit therapeutic effects against various diseases such as autoimmune diseases including pruritus due to psoriasis and atopic dermatitis, allergic rhinitis, osteoporosis, rheumatoid arthritis, and systemic lupus erythematosus, inflammatory diseases, and tumors, mainly through expression analysis in patients and experiments with animal models.

For example, decreased expression of Sema3A has been reported in the skin of patients with psoriasis or atopic dermatitis (Non Patent Literatures 9 and 10). Sema3A has inhibitory activity on C-fiber neurite outgrowth. In the skin of patients with psoriasis or atopic dermatitis, the decreased expression of Sema3A induces the outgrowth of C-fiber neurites, which is believed to result in susceptibility to itchiness. Indeed, the application of Sema3A to the skin of atopic dermatitis mouse models through intradermal administration or as an ointment has been reported to improve pruritic behavior caused by atopic dermatitis (Non Patent Literatures 11 and 12).

Sema3A has also been reported to be involved in airway hyperreactivity in allergic rhinitis, for example (Non Patent Literature 13). The expression of Sema3A decreases in epithelial cells in the nasal cavity of allergic rhinitis mouse models, which leads to an increased innervation density in the nasal turbinate lamina propria. This is believed to be one cause of the exacerbation of hypersensitivity such as sneezing and itching. Intranasal administration of Sema3A to allergic rhinitis mouse models has been reported to reduce the innervation density in the nasal turbinate lamina propria, and improve sneezing or pruritic behavior.

Furthermore, Sema3A is known to be also involved in the control of bone density. Sema3A has an activity to both activate osteoblasts and suppress osteoclast differentiation in vitro, and mice with systemic Sema3A deficiency develop osteoporosis-like symptoms. Furthermore, the administration of Sema3A to mouse models in which osteoporosis-like symptoms were induced by oophorectomy has been reported to improve the bone density (Non Patent Literature 14). In addition to the direct action of Sema3A upon osteoblasts and osteoclasts, a Sema3A-mediated bone density control mechanism through sensory innervation to bone has also been reported. In neuron-specific Sema3A-deficient mice, an osteoporosis-like decrease in bone density comparable to that in mice with systemic Sema3A deficiency has been reported (Non Patent Literature 5).

Furthermore, Sema3A has been reported to be involved in autoimmune diseases and inflammatory diseases such as rheumatoid arthritis and systemic lupus erythematosus. For example, there is a report that, compared to normal human peripheral blood, the peripheral blood of rheumatoid arthritis patients shows a decrease in the level of Sema3A mRNA or protein produced upon in vitro activation of peripheral mononuclear blood cells (PBMCs), CD4-positive T cells, and CD8-positive T cells with anti-CD3 antibody and anti-CD28 antibody. Likewise, a decrease in the mRNA expression of Sema3A has been reported in rheumatoid arthritis patient-derived synovial tissue, compared to healthy human-derived synovial tissue. Furthermore, intraperitoneal administration of plasmids encoding Sema3A protein to collagen-induced arthritis mouse models has been reported to show an improvement in arthritis score or an improvement in hindlimb swelling (Non Patent Literature 16).

It has also been reported that the Sema3A concentration in the peripheral blood of systemic lupus erythematosus patients is significantly lower than that in the peripheral blood of healthy humans, and that in $CD19+CD25^{high}$ B cells collected from the peripheral blood of systemic lupus erythematosus patients, the expression of Sema3A is lower than that in the same cells collected from healthy individuals, which suggests the possibility that this change in the expression level of Sema3A in systemic lupus erythematosus patients may affect the activation of B cells (Non Patent Literature 17).

Furthermore, the expression of Sema3A has been reported to be lower in malignant melanoma skin tissues from melanoma patients than that in normal skin tissues. It has also been reported that murine malignant melanoma cell lines in which the Sema3A gene was transfected and stably expressed exhibit reduced migration and invasiveness of tumor cells in vitro and increased sensitivity to anti-cancer agents, compared to parental cell lines not transfected with the Sema3A gene. Likewise, in mouse models injected subcutaneously with tumor cells, murine malignant melanoma cell lines in which the Sema3A gene was transfected and stably expressed have been reported to exhibit suppressed tumor metastasis and retarded tumor growth, compared to parental cell lines not transfected with the Sema3A gene (Non Patent Literature 18).

These reports have suggested the utility of Sema3A as a therapeutic drug for various diseases such as autoimmune diseases including pruritus due to psoriasis and atopic dermatitis, allergic rhinitis, osteoporosis, rheumatoid arthritis, and systemic lupus erythematosus, inflammatory diseases, and tumors.

However, no report has heretofore been made on an antibody that binds to one of the receptors, Plexin-A1, and has an activity similar to that of Sema3A (agonist antibody). Furthermore, it has been unclear as to which region of the amino acid sequence of Plexin-A1 is bound by the antibody that binds to Plexin-A1 and has agonistic activity.

CITATION LIST

Non Patent Literature

Non Patent Literature 1: Kolodkin, A L. et al., Cell, 75, 1389-1399 (1993)
Non Patent Literature 2: Tessier-Lavigne, M. et al., Science, 274, 1123-1133 (1996)
Non Patent Literature 3: Pasterkamp, R J. et al., Curr. Opin. Neurobiol., 13, 79-89 (2003)
Non Patent Literature 4: Wong A W et al., Nat. Immunol., 4(9), 891-898 (2003)
Non Patent Literature 5: Takegahara N. et al., Nat. Cell. Biol., 8, 615-622 (2006)
Non Patent Literature 6: Eun S Y et al., J. Immunol., 177(7), 4271-4275 (2006)
Non Patent Literature 7: Janssen. B. J. et al., Nat. Struct. Mol. Biol., 19, 1293-1299 (2012)
Non Patent Literature 8: Yukiko Matsunaga et al., The Journal of Experimental Medicine 31 (4), 523-530 (2013)
Non Patent Literature 9: Kouo, K. et al., Acta Derm. Venereol., 92, 521-528 (2012)
Non Patent Literature 10: Tominaga, M. et al., Journal of Dermatological Science, 55, 40-46 (2009)
Non Patent Literature 11: Yamaguchi, J. et al., Journal of Investigative Dermatology, 128, 2842-2849 (2008)
Non Patent Literature 12: Negi, O. et al., Journal of Dermatological Science, 66, 37-43 (2012)
Non Patent Literature 13: Sawaki, H. et al., J. Pharmacol. Sci., 117, 34-44 (2011)
Non Patent Literature 14: Hayashi, M. et al., Nature, 485, 69-74 (2012)
Non Patent Literature 15: Fukuda, T. et al., Nature, 497, 490-493 (2013)
Non Patent Literature 16: Catalano, A., The Journal of Immunology, 185, 6373-83 (2010)
Non Patent Literature 17: Vadasz, Z. et al., Arthritis Research & Therapy, 14, R146 (2012)
Non Patent Literature 18: Chakraborty, G. et al., PLoS ONE, 7(3), e33633 (2012)

SUMMARY OF INVENTION

Technical Problem

The present invention was made in view of the aforementioned circumstances, and an object of the present invention is to provide a novel anti-Plexin-A1 agonist antibody, a pharmaceutical composition containing the agonist antibody, a prophylactic and/or therapeutic agent for diseases associated with a quantitative or qualitative decrease in function of a class 3 semaphorin, which contains the pharmaceutical composition, and a kit therefor.

Solution to Problem

As a result of extensive research to solve the aforementioned problem, the present inventors successfully acquired a novel anti-Plexin-A1 agonist antibody. The present inventors also found that the anti-Plexin-A1 agonist antibody recognizes an epitope present in a region of Plexin-A1 different from that of an anti-Plexin-A1 antagonist antibody. The present invention was accomplished on the basis of this finding, and relates to the following [1] to [15]:

[1] An anti-Plexin-A1 agonist antibody.
[2] The antibody according to [1], which has a class 3 semaphorin-like activity.
[3] The antibody according to [2], wherein the class 3 semaphorin-like activity is a semaphorin 3A-like activity.
[4] The antibody according to [2] or [3], wherein the class 3 semaphorin-like activity is an activity to promote dendritic cell contraction or glioma cell contraction.
[5] The antibody according to any of [1] to [4], which specifically binds to an epitope in a sema domain of Plexin-A1.
[6] The antibody according to [5], wherein the epitope in the sema domain is an epitope in a C-terminal region of the sema domain.
[7] The antibody according to [6], wherein the C-terminal region is for binding to residues 461-514 of SEQ ID NO: 3 or residues 459-512 of SEQ ID NO: 52.
[8] The antibody according to any of [1] to [7], which cross-reacts with human Plexin-A1 and mouse Plexin-A1.
[9] The antibody according to any of [1] to [8], which is a monoclonal antibody.
[10] The antibody according to any of claims [1] to [9], which is a chimeric antibody, a humanized antibody, or a human antibody.
[11] The antibody according to any of [1] to [10], which is Fab, scFv, F(ab')2, a single-chain antibody, or a bispecific antibody. [12] A pharmaceutical composition comprising the antibody according to any of [1] to [11] and a pharmaceutically acceptable carrier.
[13] A method for producing a pharmaceutical composition comprising mixing the antibody according to any of [1] to [11] and a pharmaceutically acceptable carrier.
[14] The pharmaceutical composition according to [12], which is for use in prevention and/or treatment of diseases associated with a quantitative or qualitative decrease in function of a class 3 semaphorin.
[15] A kit comprising the antibody according to any of [1] to [11] or the pharmaceutical composition according to [12] or [14] and instructions for administering the antibody or pharmaceutical composition for preventing and/or treating diseases associated with a quantitative or qualitative decrease in function of a class 3 semaphorin.

Advantageous Effects of Invention

According to the present invention, there are provided a novel anti-Plexin-A1 agonist antibody, a pharmaceutical composition containing the agonist antibody, a prophylactic and/or therapeutic agent for diseases associated with a quantitative or qualitative decrease in function of a class 3 semaphorin, which contains the pharmaceutical composition, and a kit therefor.

BRIEF DESCRIPTION OF DRAWINGS

FIG. 11 illustrates a comparison of amino acid sequences between the mouse PlexinA1 sema domain and the mouse PlexinA2 sema domain. A site used for the preparation of the mouse PlexinA1/A2 chimeric protein is underlined.

FIG. 12 illustrates a comparison of amino acid sequences between the mouse PlexinA1 sema domain and the human PlexinA1 sema domain. A site used for the preparation of the mouse PlexinA1/A2 chimeric protein is underlined.

DESCRIPTION OF EMBODIMENTS

Plexin-A1

Figure 1:
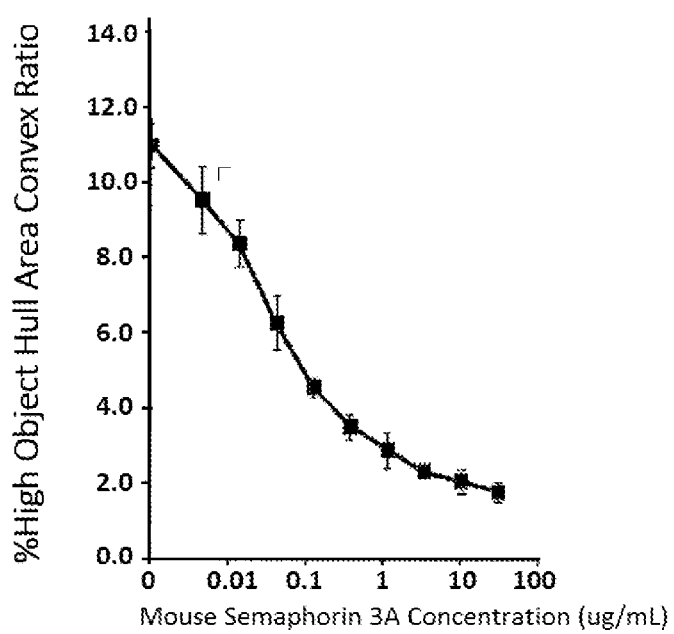
FIG. 1 illustrates a plot showing values of cell contraction upon 5-hour stimulation of mouse bone marrow-derived dendritic cells with mouse semaphorin 3A.

Plexin-A1 may be human or murine Plexin-A1, for example, although not particularly limited thereto. The amino acid sequence and nucleotide sequence of murine Plexin-A1 are published in, for example, Kameyama T et al. "Biochemical and biophysical research communications."; Biochem Biophys Res Commun. 1996, 226(2), 524-9; and Accession No. D86948, NCBI Reference Sequence NP_032907.1 from Genbank. The amino acid sequence and nucleotide sequence of human Plexin-A1 are published in, for example, Tamagnone L et al. Cell. 1999, 99(1), 71-80; Accession No. X87832, NCBI Reference Sequence NP_115618.3 from Genbank; and NCBI Reference Sequence NM_032242. Plexin-A1 can be readily cloned on the basis of the above-described sequence information. The amino acid sequence or nucleotide sequence of Plexin-A1 can be modified, as appropriate, within the scope of the intended use. The amino acid sequence of Plexin-A1 is well-conserved between humans and mice. As used herein, the term "Plexin-A1" is also designated as PlexinA1 or PlxnA1. Furthermore, the simple recitation "Plexin-A1" refers to human and/or murine Plexin-A1, and the same holds true for other factors (e.g., semaphorin 3A).

Anti-Plexin-A1 Agonist Antibody

The anti-Plexin-A1 agonist antibody refers to, for example, an antibody that specifically binds to the Plexin-A1 protein and has Plexin-A1-mediated signaling activity, including, for example, an antibody having a class 3 semaphorin-like activity.

The class 3 semaphorin-like activity refers to at least one of the activities that can be exhibited by a class 3 semaphorin in vitro or in vivo, and is preferably a semaphorin 3A-like activity, i.e., at least one of the activities that can be exhibited by semaphorin 3A in vitro or in vivo. For example, this activity refers to an activity transduced by a complex of semaphorin 3A, neuropilin-1, and Plexin-A1. The activity as used herein includes promoting activity and suppressing activity. Furthermore, the activity transduced by the complex of semaphorin 3A, neuropilin-1, and Plexin-A1 refers to, for example, an activity transduced when semaphorin 3A forms a ternary complex with neuropilin-1 and Plexin-A1. Specific examples of semaphorin 3A-like activities include a cell contraction-promoting activity, for example, a dendritic cell or glioma cell contraction-promoting activity. Examples of glioma cells include human glioblastoma-derived cells and human glioblastoma/astrocytoma-derived cells, and specifically, U-87 MG cells.

One embodiment of the anti-Plexin-A1 agonist antibody of the present invention may be, for example, an antibody having a cell contraction-promoting activity, for example, an antibody having a dendritic cell or glioma cell contraction-promoting activity. The recitation "having an activity" includes the meaning "enhancing the activity".

Anti-Plexin-A1 Antagonist Antibody

The anti-Plexin-A1 antagonist antibody refers to, for example, an antibody that specifically binds to the Plexin-A1 protein to prevent or attenuate the Plexin-A1-mediated signaling activity, including, for example, an antibody that prevents or attenuates the class 3 semaphorin-like activity, and preferably an antibody that prevents or attenuates the semaphorin 3A-like activity. Examples of the anti-Plexin-A1 agonist antibody include an antibody that inhibits cell contraction, which is specifically an antibody that inhibits dendritic cell or glioma cell contraction.

Class 3 Semaphorins

More than 20 members of semaphorins have been identified to date, and the semaphorin family is characterized by sharing a conserved region consisting of about 500 amino acids, referred to as the Sema domain. These semaphorins are classified into eight sub-classes on the basis of structural difference at the C-terminus following the Sema domain. Sema3A, Sema3B, Sema3C, Sema3D, Sema3E, and Sema3F are known as class 3 semaphorins. As used herein, the term "class 3 semaphorins" includes Sema3A, Sema3B, Sema3C, Sema3D, Sema3E, and Sema3F, with Sema3A (semaphorin 3A) being preferred.

Semaphorin 3A

Semaphorin 3A may be human or murine semaphorin 3A, although not particularly limited thereto. The amino acid sequence of human semaphorin 3A is published in NCBI Reference Sequence NP_006071.1, for example. The amino acid sequence of murine semaphorin 3A is published in NP_033178.2, for example. Semaphorin 3A can be readily cloned on the basis of the above-described sequence information. The amino acid sequence of semaphorin 3A can be modified, as appropriate, within the scope of the intended use. Semaphorin 3A is herein also designated as Sema3A.

Sema Domain

The sema domain typically corresponds to positions 51 to 487 of SEQ ID NO: 3 in human Plexin-A1, positions 49 to 485 of SEQ ID NO: 52 in mouse Plexin-A1, and positions 50 to 483 of SEQ ID NO: 53 in mouse Plexin-A2.

Semaphorin 3A-Like Activity

The semaphorin 3A-like activity as one preferred example of the class 3 semaphorin-like activity specifically refers to, for example, the following activities: a cell (e.g., dendritic cell)-contracting activity; an activity to promote migration of dendritic cells to Draining Lymph Node (U.S. Patent Application Publication No. 2012/0322085); an osteoclast differentiation-suppressing activity and an osteoblast differentiation-promoting activity (Hayashi M et al., Nature, 2012, 485, 69-74); and a neuronal outgrowth inhibitory activity (U.S. Pat. No. 7,642,362). The agonist antibody of the present invention may have at least one of the class 3 semaphorin-like activities. For example, the agonist antibody of the present invention promotes cell contraction, and, for example, promotes dendritic cell or glioma cell contraction. The antagonist antibody may inhibit at least one of the class 3 semaphorin-like activities. For example, the antagonist antibody inhibits cell contraction, and, for example, inhibits dendritic cell or glioma cell contraction.

The recitation "has", "have", or "having" the class 3 semaphorin-like activity means that the class 3 semaphorin-like activity increases in the presence of the anti-Plexin-A1 agonist antibody of the present invention, compared to that in the absence of the agonist antibody, preferably by 1% or more, 5% or more, 10% or more, 20% or more, 30% or more, 50% or more, 75% or more, 80% or more, 90% or more, 95% or more, 100% or more, 200% or more, 300% or more, 400% or more, 500% or more, 600% or more, 700% or more, 800% or more, 900% or more, or 1000% or more.

The recitation "prevents or attenuates" the class 3 semaphorin-like activity means that the class 3 semaphorin-like activity is reduced in the presence of the anti-Plexin-A1 antagonist antibody, compared to that in the absence of the antagonist antibody, preferably by 1% or more, 5% or more, 10% or more, 20% or more, 30% or more, 50% or more, 75% or more, 80% or more, 90% or more, or 95% or more.

Cell-Contracting Activity and Neuronal Outgrowth Inhibitory Activity

Sema3A exhibits contracting activities for various cells, for example, by retracting neuronal growth cones of neurons to suppress axonal extension, or by inducing dendritic cell contraction during the process in which dendritic cells pass through microlymphatic vessels, thereby controlling migration of dendritic cells. Sema3A thus controls diverse biological reactions including neuronal circuit formation and immunoreactions.

Any methods known to those skilled in the art can be used as appropriate for measuring cell contraction, and examples of such methods include, although not limited to, a method that involves direct image analysis of cell morphology, and a method that involves measuring changes in cell morphology or adhesiveness as electrical impedance, using an apparatus such as xCELLigence (registered trademark).

Method that Involves Direct Image Analysis of Cell Morphology

Cells such as various tumor cells, endothelial cells including HUVEC, dorsal root ganglion (DRG) neurons, and dendritic cells are seeded into 96-well cell culture plates, and cultured for several hours to 1 day to induce cell adhesion. This is followed by the addition of Sema3A, and the cells are further cultured in a 37° C., $CO_2$ 5% incubator for about 30 minutes to several hours. In this case, wells without the addition of Sema3A are provided as a control. Then, images of cell morphology are taken by microscopic observation or using a cell image analyzer for high-content screening such as ArrayScan (registered trademark), and changes in cell morphology are quantified by means of image analysis software (e.g., Cellomics-vHCSTM:Scan).

As an example of an index used for quantifying changes in cell morphology, an index denoted as the "% High Object Convex Hull Area ratio" may be used, for example. This involves computing the proportion of cells for which the computed value of the ratio of the cell area to the convex hull area exceeds a certain threshold, and comparing this value between the cases with and without the addition of Sema3A to measure the cell contraction-inducing activity of Sema3A. The cell contraction means that the above-described value is reduced with the addition of Sema3A, compared to that without the addition of Sema3A, preferably by 1% or more, 5% or more, 10% or more, 20% or more, 30% or more, 50% or more, 75% or more, 80% or more, 90% or more, or 95% or more.

The recitation "the agonist antibody of the present invention has a contraction-promoting activity" means that the above-described value as measured using the above-described method is reduced in the presence of the antibody, compared to that in the absence of the antibody, preferably by 1% or more, 5% or more, 10% or more, 20% or more, 30% or more, 50% or more, 75% or more, 80% or more, 90% or more, or 95% or more.

Examples of other indices used for quantifying changes in cell morphology include an index obtained by quantifying neurite outgrowth as the average neurite outgrowth/neuron/well through the use of the neurite outgrowth application of image analysis software (e.g., Cellomics-vHCSTM:Scan). The cell contraction means that the above-described value is reduced with the addition of Sema3A, compared to that without the addition of Sema3A, preferably by 1% or more, 5% or more, 10% or more, 20% or more, 30% or more, 50% or more, 75% or more, 80% or more, 90% or more, or 95% or more.

The recitation "the agonist antibody of the present invention has a contraction-promoting activity" means that the above-described value as measured using the above-described method is reduced in the presence of the antibody, compared to that in the absence of the antibody, preferably by 1% or more, 5% or more, 10% or more, 20% or more, 30% or more, 50% or more, 75% or more, 80% or more, 90% or more, or 95% or more.

Additionally, a method can also be used that involves computing the area of cells from taken images, and determining cells for which the cell area has decreased below a certain threshold to be retracted cells.

Method that Involves Measuring Changes in Cell Morphology and/or Adhesiveness as Electrical Impedance Cells such as various tumor cells, endothelial cells including HUVEC, dorsal root ganglion (DRG) neurons, and dendritic cells are seeded into the tissue culture E-Plate having electrodes integrated into the bottom of the wells, and cultured for several hours to 1 day to induce cell adhesion. This is followed by the addition of Sema3A, and the cells are further cultured in a 37° C., $CO_2$ 5% incubator for about several minutes to several hours. In this case, wells without the addition of Sema3A are provided as a control. Changes in cell morphology and/or adhesiveness are detected as electrical impedance, using CELLigence (registered trademark). This electrical impedance is detected using RTCA software (registered trademark), which is analytical software of xCELLigence (registered trademark), and created as a unitless parameter referred to as Cell Index (CI). Alternatively, a unitless parameter referred to as Normalized Cell Index is computed from a relative change in CI with respect to the current cell status. This Normalized CI value is compared between the cases with and without the addition of Sema3A to measure the cell contraction-inducing activity of Sema3A. The cell contraction means that the CI value is reduced with the addition of Sema3A, compared to that without the addition of Sema3A, preferably by 1% or more, 5% or more, 10% or more, 20% or more, 30% or more, 50% or more, 75% or more, 80% or more, 90% or more, or 95% or more.

The recitation that "the agonist antibody of the present invention has a contraction-promoting activity" means that the above-described value as measured using the above-described method is reduced in the presence of the antibody, compared to that in the absence of the antibody, preferably by 1% or more, 5% or more, 10% or more, 20% or more, 30% or more, 50% or more, 75% or more, 80% or more, 90% or more, or 95% or more.

Activity to Promote Migration of Dendritic Cells to Draining Lymph Node

Sema3A exhibits an actomyosin contraction-inducing activity by acting upon a heteroreceptor complex between Plexin-A1 and Neuropilin-1 on dendritic cells, and controls the passage of dendritic cells through intercellular spaces of microlymphatic vessels by inducing changes in cell morphology.

Any methods known to those skilled in the art can be used as appropriate for measuring the activity, and examples of such methods include, although not limited to, a method that involves measuring the activity through the use of an in vitro cell migration assay using the Boyden chamber.

Specifically, the Transwell (Corning) is placed in a 24-well plate containing 0.6 mL of 0.1% BSA in RPMI1640 containing chemokines such as CCL21 and CXCL12. Dendritic cells are added to the upper chamber of the Transwell and incubated at 37° C. for 1 to 3 hours. Then, the number of cells in the lower chamber is counted. For a transendothelial cell migration assay, lymphatic endothelial cells or vascular endothelial cells are deposited on the upper chamber. Briefly, SVEC4-10 or HMVEC-dLy cells are seeded in an upper or lower part of a Transwell insert coated with 2 µg/mL of fibronectin. After 1 to 2 days of culturing, a transendothelial cell migration assay is performed in accordance with the same method as that of the cell migration assay described above. The cell migration-promoting activity of Sema3A is measured as follows: In these assays, Sema3A is added with dendritic cells into the upper chamber of the Transwell, and comparing the measured number of dendritic cells migrated to the lower chamber with that in wells without the addition of Sema3A.

The activity to promote migration of dendritic cells to draining lymph node means that the number of dendritic cells migrated to the lower chamber increases in wells to which Sema3A was added, compared to that in wells to which Sema3A was not added, preferably by 1% or more, 5% or more, 10% or more, 20% or more, 30% or more, 50% or more, 75% or more, 80% or more, 90% or more, or 95% or more.

Osteoclast Differentiation-Suppressing Activity and Osteoblast Differentiation-Promoting Activity Sema3A has been reported to exhibit a bone-protecting activity by exerting suppressive action upon osteoclast differentiation, and simultaneously exerting promotional action upon osteoblast activation, through receptors expressed by osteoclasts and osteoblasts.

Any methods known to those skilled in the art can be used as appropriate for measuring the osteoclast differentiation-suppressing activity or osteoblast differentiation-promoting activity, and examples of such methods include, although not limited to, the following methods.

Osteoclast Differentiation-Suppressing Activity

While a variety of methods are available for measuring the activity, the activity may be evaluated by, for example, tartrate-resistant acid phosphatase (TRAP) staining. Specifically, bone marrow cells are cultured in M-CSF-containing a-MEM medium for 48 hours or longer to prepare bone marrow monocyte/macrophage precursor cells. The medium is replaced with medium supplemented with RANKL, and the culture is continued for several days. For the evaluation of Sema3A, the medium is replaced with medium supplemented with Sema3A, and RANKL is added after 10 to 12 hours and the culture is continued for several days. The medium is replaced at an interval of several days, and after osteoclast formation is confirmed, TRAP staining and nuclear staining are performed. The osteoclast differentiation-suppressing activity of Sema3A is measured as follows: A stained image of cells to which Sema3A was added is acquired using a microscope or a cell image analyzer for high-content screening such as ArrayScan (registered trademark), and this stained image is compared with that of cells to which Sema3A was not added. Specifically, numbers of TRAP-positive cells or numbers of TRAP-positive multinucleated cells per well are counted and compared.

The osteoclast differentiation-suppressing activity means that the number of TRAP-positive cells or the number of TRAP-positive multinucleated cells is reduced in wells to which Sema3A was added, compared to that in wells to which Sema3A was not added, preferably by 1% or more, 5% or more, 10% or more, 20% or more, 30% or more, 50% or more, 75% or more, 80% or more, 90% or more, or 95% or more.

Osteoblast-Activating Activity

While a variety of methods are available for measuring the activity, the activity can be evaluated by, for example, alkaline phosphatase (ALP) staining or ALP activity measurement, or calcification detection. Specifically, calvarial cells or MC3T3-E1 cells are seeded into collagen-coated plates, and cultured in a-MEM medium containing ascorbic acid and β-glycerophosphoric acid. For the evaluation of Sema3A, Sema3A is added to the medium, and the cells are cultured. The medium is replaced at an interval of several days, and, after the completion of culture, ALP staining is performed, and then images are taken with a microscope, or the ALP activity is measured using absorptiometry. For calcification detection, Alizarin Red staining is performed. The osteoblast-activating effect of Sema3A is evaluated as follows: A stained image of cells to which Sema3A was added is acquired with a microscope, and this stained image is compared with that of cells to which Sema3A was not added. Specifically, images of stained cells are taken with a microscope, and the presence or absence of the activity is determined by visually comparing intensities of ALP staining or Alizarin Red staining.

The osteoblast-activating activity means that the absorbance of ALP activity or the intensity of Alizarin Red staining increases in wells to which Sema3A was added, compared to that in wells to which Sema3A was not added, preferably by 1% or more, 5% or more, 10% or more, 20% or more, 30% or more, 50% or more, 75% or more, 80% or more, 90% or more, 95% or more, 100% or more, 200% or more, 300% or more, 400% or more, 500% or more, 600% or more, 700% or more, 800% or more, 900% or more, or 1000% or more.

Antibody

The term "antibody" is used in the broadest sense, and may refer to any of monoclonal antibodies, polyclonal antibodies, dimers, multimers, multi-specific antibodies (e.g., bispecific antibody), antibody derivatives, and modified antibodies (Miller K et al., J Immunol., 2003, 170(9), 4854-61), as long as they exhibit desired biological activities. The antibody may be murine, human, humanized, or chimeric, or may be derived from other species. The antibody disclosed herein may be any type (e.g., IgG, IgE, IgM, IgD, and IgA) or class (e.g., IgG1, IgG2, IgG3, IgG4, IgA1, and IgA2) or subclass of immunoglobulin molecule. The immunoglobulin may be derived from any species (e.g., humans, mice, or rabbits). Note that the terms "antibody" and "immunoglobulin" are interchangeably used in a broad sense.

An "antibody derivative" includes a portion of the antibody, preferably a variable domain of the antibody or at least an antigen binding region of the antibody. Antibody derivatives include, although not limited to, Fab, Fab', F(ab')2 or Fv fragments, linear antibodies, single-chain antibodies (scFv), sc(Fv)$_2$, Fab$_3$, domain antibodies (dAb) (WO 2004/058821 and WO 2003/002609), diabodies, triabodies, tetrabodies, minibodies, and multi-specific antibodies formed from antibody derivatives. As used herein, the term "Fv" refers to a minimal antibody derivative, and includes a complete antigen recognition region and antigen binding region. Furthermore, the antibody derivative may be an IgG antibody fused with Fc. Reference may be made to, for example, the specification of U.S. Pat. No. 5,641,870, EXAMPLE 2; Zapata G et al., Protein Eng., 1995, 8(10), 1057-1062; Olafsen T et al., Protein Eng. Design & Sel., 2004, 17(4):315-323; Holliger P et al., Nat. Biotechnol., 2005, 23(9); 1126-36; Fischer N et al., Pathobiology, 2007, 74(1): 3-14; Shen J et al., J. Immunol Methods., 2007, 318, 65-74; and Wu et al., Nat. Biotechnol., 2007, 25(11), 1290-7.

The term "bispecific" antibody refers to an antibody having variable regions that recognize different epitopes in the same antibody molecule. The bispecific antibody may be an antibody that recognizes two or more different antigens, or may be an antibody that recognizes two or more different epitopes on the same antigen.

An IgG-type bispecific antibody can be secreted by a hybrid hybridoma (quadroma) produced by fusing two types of hybridomas that produce IgG antibodies (Milstein C et al., Nature, 1983, 305: 537-540). An IgG-type bispecific antibody can also be secreted by introducing genes of L chains and H chains constituting two IgGs of interest, i.e., a total of four types of genes, into cells for co-expression.

In this case, if a suitable amino acid substitution is introduced into the CH3 region of an H chain, IgGs having a heterologous combination of H chains can be preferentially secreted (Ridgway J B et al., Protein Engineering, 1996, 9: 617-621; Merchant A M et al., Nature Biotechnology, 1998, 16: 677-681; WO2006/106905; and Davis J H et al., Protein Eng. Des. Sel., 2010, 4: 195-202).

Regarding L chains, L chain variable regions are less diverse than H chain variable regions, and hence, a common L chain that may confer a binding capacity to both H chains can be obtained. Efficient expression of a bispecific IgG is achieved by introducing the genes of the common L chain and both H chains into cells for expression of IgGs.

As used herein, the term "common L chain" refers to an L chain that can associate with two or more different H chains, and exhibit binding capacities to the respective antigens. The term "different H chains" preferably refers to H chains of antibodies directed against different antigens, but is not limited thereto, and also refers to H chains that differ in amino acid sequence from each other. The common L chain can be acquired in accordance with the method described in WO 2006/109592, for example.

A bispecific antibody can also be prepared by chemically crosslinking Fab's. Instead of chemical crosslinking, a leucine zipper derived from Fos, Jun, or the like can also be used, and this method is similarly applicable to scFv, Fv, and the like, without being limited to Fab'.

Additionally, bispecific antibodies are also known including IgG-scFv (Protein Eng. Des. Sel., 2010, April; 23(4): 221-8), sc(Fv)$_2$ such as BiTEs (Drug Discov. Today, 2005 Sep. 15; 10(18): 1237-44), DVD-Ig (Nat. Biotechnol., 2007, November; 25(11): 1290-7. Epub 2007 Oct. 14, MAbs, 2009, July; 1(4): 339-47. Epub 2009 Jul. 10, and IDrugs, 2010, 13: 698-700), two-in-one antibodies (Science, 2009 Mar. 20; 323(5921): 1610-4, and Immunotherapy, 2009, September; 1(5): 749-51), Tri-Fab, tandem scFv, and diabodies (MAbs, 2009, November; 1(6):539-547). Furthermore, bispecific antibodies can be efficiently prepared by preferentially secreting a heterologous combination of Fc fragments, using molecular forms such as scFv-Fc and scaffold-Fc (Ridgway J B et al., Protein Engineering, 1996, 9: 617-621, Merchant A M et al., Nature Biotechnology, 1998, 16: 677-681, WO2006/106905, and Davis J H et al., Protein Eng. Des. Sel., 2010, 4: 195-202).

The "antibody which cross-reacts", which is also referred to as a cross-reacting antibody, cross-reactive antibody, or cross-reaction antibody, refers to an antibody that recognizes an identical or similar epitope on a plurality of antigens. As used herein, the plurality of antigens may be, for example, antigens of the same or different species.

Examples of modified antibodies include antibodies conjugated to various molecules such as polyethylene glycol (PEG). The substance to be conjugated with a modified antibody of the present invention is not limited. Such a modified antibody can be obtained by chemically modifying a produced antibody. Such methods have already been established in the art.

Examples of antigen binding regions include antibodies, scaffold molecules (antibody-like molecules), sites necessary for binding with antigens such as peptides, and fragments including such sites. Scaffold molecules are molecules that exhibit their functions by binding to target molecules, and any conformationally stable polypeptides capable of binding to at least one target antigen can be used as scaffold molecules. Examples of such polypeptides include antibody variable regions, fibronectin (WO 2002/032925), protein A domains (WO 1995/001937), LDL receptor A domains (WO 2004/044011 and WO 2005/040229), ankyrin (WO 2002/020565), and the molecules described in Nygren et al. (Current Opinion in Structural Biology, 7: 463-469 (1997), and Journal of Immunol. Methods, 290: 3-28 (2004)), Binz et al. (Nature Biotech., 23: 1257-1266 (2005)), and Hosse et al. (Protein Science, 15: 14-27 (2006)). Additionally, peptide molecules capable of binding to target antigens can be used, as described in Curr. Opin. Mol. Ther., 2010 August; 12(4): 487-95; and Drugs, 2008; 68(7): 901-12.

The antibody of the present invention is preferably a recombinant antibody produced using a gene recombination technique. A recombinant antibody can be obtained by cloning DNA encoding the antibody from hybridomas or antibody-producing cells such as antibody-producing sensitized lymphocytes, incorporating the cloned DNA into a vector, and introducing the vector into a host (host cells) to produce the antibody.

The antibody of the present invention may be from a non-limiting species, for example, a human antibody, a mouse antibody, or a rat antibody. The antibody of the present invention may also be a genetically engineered antibody such as a chimeric antibody or a humanized antibody.

Genetically engineered antibodies can be produced using existing methods. Specifically, a chimeric antibody, for example, is an antibody containing H chain and L chin variable regions of an antibody from immunized animals, as well as H chain and L chain constant regions of a human antibody. The chimeric antibody can be obtained by ligating DNA encoding the variable regions of the antibody from immunized animals to DNA encoding the constant regions of the human antibody, incorporating the resulting product into an expression vector, and introducing the vector into a host to produce the antibody.

Methods for acquiring human antibodies are already known, and a human antibody of interest can be acquired by, for example, immunizing a transgenic animal having the entire repertoire of human antibody genes with an antigen of interest (see WO 93/12227, WO 92/03918, WO 94/02602, WO 94/25585, WO 96/34096, and WO 96/33735).

Furthermore, a human antibody can be produced by a hybridoma-based method.

Human myeloma and mouse-human heterologous cell lines for the production of human monoclonal antibodies are usable (see Kozbor J., Immunol., 133: 3001 (1984); Brodeur et al., Monoclonal Antibody Production Techniques and Applications, pp 51-63 (Marcel Dekker, Inc., New York, 1987); and Boerner et al., J. Immunol., 147: 86 (1991)). Human antibodies produced via a human B cell hybridoma technique are also known (see Li et al., Proc. Natl. Acad. Sci. USA, 103: 3557-3562 (2006)). A human hybridoma technique (trioma technique) is also usable (see Vollmers and Brandlein, Histology and Histopathology, 20(3): 927-937

(2005); and Vollmers and Brandlein, Methods and Findings in Experimental and Clinical Pharmacology, 27(3): 185-91 (2005)).

A human antibody can also be produced by isolating an Fv clone variable domain sequence selected from a human phage display library. Such a variable domain sequence may be combined with a desired human constant domain. Techniques for selecting human antibodies from antibody libraries will be described hereinafter. Note that these techniques are also applicable to antibodies other than human antibodies.

Many antibody libraries are already known, and methods for preparing such antibody libraries are also known; therefore, those skilled in the art can acquire an antibody library, as appropriate. For phage libraries, for example, reference may be made to documents such as Clackson et al., Nature, 1991, 352: 624-8, Marks et al., J. Mol. Biol., 1991, 222: 581-97, Waterhouses et al., Nucleic Acids Res., 1993, 21: 2265-6, Griffiths et al., EMBO J., 1994, 13: 324.0-60, Vaughan et al., Nature Biotechnology, 1996, 14: 309-14, and WO 96/07754. Additionally, known methods such as a method for producing libraries using eukaryotic cells (WO 95/15393) and a ribosome display method can be used.

Libraries include, although not limited to, libraries known to those skilled in the art (Methods Mol. Biol., 2002; 178: 87-100; J. Immunol. Methods, 2004 June; 289(1-2): 65-80; and Expert Opin. Biol. Ther., 2007 May; 7(5): 763-79), i.e., human naive libraries, non-human animal and human immune libraries, semi-synthetic and synthetic libraries. Examples of methods, however, are not particularly limited thereto.

Furthermore, a technique for acquiring human antibodies through panning by using human antibody libraries is known. For example, human antibody variable regions as single-chain antibodies (scFvs) may be expressed on the phage surface in accordance with a phage display method, and phages bound to the antigen may be selected. Through analysis of the genes of the selected phages, DNA sequences encoding the human antibody variable regions bound to the antigen can be determined. Once the DNA sequences of scFvs bound to the antigen are known, suitable expression vectors can be prepared on the basis of these sequences to acquire human antibodies. Such methods are already well known, and reference can be made to WO 92/01047, WO 92/20791, WO 93/06213, WO 93/11236, WO 93/19172, WO 95/01438, and WO 95/15388.

Antibodies or antibody fragments isolated from human antibody libraries are regarded herein as human antibodies or human antibody fragments.

A humanized antibody is an engineered antibody also referred to as a reshaped human antibody. A humanized antibody is constructed by grafting the CDRs of an antibody derived from an immunized animal into the complementarity determining regions of a human antibody. Common gene recombination techniques therefor are also known (see European Patent Application Publication No. 239,400, WO 96/02576, Sato K et al, Cancer Research, 1993, 53: 851-856, and WO 99/51743).

Specific preferred embodiments of the agonist antibody of the present invention include antibodies comprising the following amino acid sequences described in the Examples below:

(a) An antibody comprising amino acid sequences of H chain CDRs 1, 2 and 3 as set forth in SEQ ID NOS: 23, 24 and 25 (H chain CDRs of hPANL #240) and amino acid sequences of L chain CDRs 1, 2 and 3 as set forth in SEQ ID NOS: 26, 27 and 28 (L chain CDRs of hPANL #240).

(b) An antibody comprising amino acid sequences of H chain CDRs 1, 2 and 3 as set forth in SEQ ID NOS: 29, 30 and 31 (H chain CDRs of 359B-2-2-3-6) and amino acid sequences of L chain CDRs 1, 2 and 3 as set forth in SEQ ID NOS: 32, 33 and 34 (L chain CDRs of 359B-2-2-3-6).

Specific preferred embodiments of the agonist antibody of the present invention further include antibodies comprising the following amino acid sequences described in the Examples below:

(a) An antibody comprising an amino acid sequence of an H chain variable region as set forth in SEQ ID NO: 21 (H chain variable region of hPANL #240) and an amino acid sequence of an L chain variable region as set forth in SEQ ID NO: 22 (L chain variable region of hPANL #240).

(b) An antibody comprising an amino acid sequence of an H chain variable region as set forth in SEQ ID NO: 35 (H chain variable region of 359B-2-2-3-6) and an amino acid sequence of an L chain variable region as set forth in SEQ ID NO: 36 (L chain variable region of 359B-2-2-3-6).

Specific preferred embodiments of the agonist antibody of the present invention further include antibodies comprising the following amino acid sequences described in the Examples below:

(a) An antibody comprising an amino acid sequence of an H chain as set forth in SEQ ID NO: 9 (H chain of hPANL #240) and an amino acid sequence of an L chain as set forth in SEQ ID NO: 10 (L chain of hPANL #240).

(b) An antibody comprising an amino acid sequence of an H chain as set forth in SEQ ID NO: 11 (H chain of 359B-2-2-3-6) and an amino acid sequence of an L chain as set forth in SEQ ID NO: 12 (L chain of 359B-2-2-3-6).

One embodiment of the present invention provides nucleic acid encoding H chain and L chain CDRs, variable regions, or the full length of the antibody sequence of hPANL #240 or 359B-2-2-3-6.

Another embodiment provides a vector incorporating the nucleic acid.

Still another embodiment provides host cells transformed with the vector.

Still another embodiment provides a method for producing the above-described antibodies by culturing the above-described cells.

Still another embodiment provides antibodies produced by the above-described method.

One embodiment of the present invention provides an anti-Plexin-A1 antibody that competes with hPANL #240 or 359B-2-2-3-6 for binding to Plexin-A1. Preferred is an anti-Plexin-A1 antibody that competes with hPANL #240 or 359B-2-2-3-6 for binding to the sema domain of Plexin-A1. More preferred is an anti-Plexin-A1 antibody that competes with hPANL #240 or 359B-2-2-3-6 for binding to residues 461-514 of SEQ ID NO: 3 in the sema domain of human Plexin-A1, or for binding to residues 459-512 of SEQ ID NO: 52 in the same domain of mouse Plexin-A1.

The present invention also provides an antibody that binds to an epitope that overlaps with that bound by the agonist antibody of the present invention. It can be confirmed whether one antibody recognizes an epitope that overlaps with that of another antibody, by competition of these antibodies for the epitope. Competition between antibodies can be evaluated by a competition binding assay, and examples of such means include biomolecular interaction analysis, including enzyme-linked immunosorbent assay (ELISA), fluorescence resonance energy transfer (FRET) assay, fluorometric microvolume assay technology (FMAT (registered trademark)), electrochemiluminescence (ECL), AlphaScreen (chemically amplified luminescence proximity homogeneous assay), radioimmunoassay (RIA), scintillation proximity assay (SPA), surface acoustic wave (SAW), microscale thermophoresis (NanoTemper Technologies), quartz crystal microbalance (QCM), Octet (from ForteBIO), and surface plasmon resonance; and kinetic exclusion assay (KinExA (registered trademark)). The amount of the antibody bound to the antigen is indirectly correlated with the binding capacity of a competing antibody candidate (test antibody) that competes for binding to the overlapping epitope. That is, as the amount or affinity of the test antibody for the overlapping epitope increases, the amount of binding of the antibody to the antigen decreases, and the amount of binding of the test antibody to the antigen increases. Specifically, the suitably labeled antibody and the test antibody are simultaneously added to the antigen, and the bound antibody is detected using the label. The amount of the antibody bound to the antigen can be readily measured by pre-labeling the antibody. For this labeling, any labeling method suitable for the technique may be selected without particular limitation. Examples of labeling methods include fluorescent labeling, radiolabeling, and enzyme labeling. For example, the fluorescently labeled antibody and the unlabeled antibody or test antibody are simultaneously added to Plexin-A1-immobilized beads, and the labeled antibody is detected using the fluorometric microvolume assay technology. Furthermore, through the use of biomolecular interaction analysis or kinetic exclusion assay, competition can be evaluated without the need to use the labeled antibody. The overlapping epitope includes not only a case where the epitopes of two antibodies are completely identical, but also a case where the epitopes are partially identical. The antibody that binds to the overlapping epitope may also be referred to herein as the antibody that binds to a competing epitope, or the competing antibody.

As used herein, the "antibody that binds to the overlapping epitope", "competing antibody", or "antibody that binds to a competing epitope" includes, for example, cases where the antibody and the test antibody do not substantially simultaneously bind to Plexin-A1. As used herein, the recitation "do not substantially simultaneously bind" refers to 60% or less, typically 50% or less, preferably 30% or less, and particularly preferably 15% or less of the binding activity of the antibody for Plexin-A1. Note that analysis of the epitope recognized by the antibody can be performed using a method known to those skilled in the art, for example, Western blotting.

A multi-specific antigen binding molecule having an antigen binding site of an antibody that binds to an epitope bound by the above-described agonist antibody or an epitope that overlaps with the epitope is capable of promoting a class 3 semaphorin-like activity, which is, for example, cell contraction. Furthermore, in the antigen binding site of the antibody that binds to the epitope that overlaps with the epitope bound by the above-described antibody, one or more amino acids can be modified to obtain an improved class 3 semaphorin-like activity.

As used herein, the term “monoclonal antibody” refers to an antibody obtained from a population of substantially homogeneous antibodies, i.e., a population of antibodies in which the individual antibodies constituting the population are homogeneous except for possible naturally occurring mutations that may be present in minor amounts. Monoclonal antibodies are highly specific, and are typically directed against a single antigenic site. Furthermore, in contrast to conventional polyclonal antibody preparations that typically contain different antibodies directed against different antigenic determinants (epitopes), a monoclonal antibody is directed against a single antigenic determinant on the antigen. In addition to their specificities, monoclonal antibodies are advantageous in that they are synthesized by, for example, hybridoma culture that does not include other antibodies. Note that the modifier “monoclonal” suggests the characteristics of the antibody obtained from a population of substantially homogeneous antibodies, and does not require the antibody to be produced by any specific method. For example, the monoclonal antibody used in the present invention may be produced by, for example, the hybridoma method (e.g., Kohler and Milstein, Nature, 256: 495 (1975)) or the recombination method (e.g., U.S. Pat. No. 4,816,567). The monoclonal antibody used in the present invention may also be isolated from phage antibody libraries (e.g., Clackson et al., Nature, 352:624-628 (1991); Marks et al., J. Mol. Biol., 222:581-597 (1991)).

The antibody of the present invention can be produced by a method known to those skilled in the art. Specifically, DNA encoding an antibody of interest is incorporated into an expression vector. In this case, the DNA is incorporated into the expression vector so as to be expressed under the control of an expression-controlled region, for example, an enhancer or promoter. Then, host cells are transformed with this expression vector for expression of the antibody. In this case, a suitable combination of a host and an expression vector may be used.

Examples of vectors include M13-based vectors, pUC-based vectors, pBR322, pBluescript, and pCR-Script. For the purpose of cDNA subcloning or processing, pGEM-T, pDIRECT, and pT7, for example, can be used besides the above-described vectors.

For the purpose of antibody production, expression vectors are particularly useful. For example, when the host is *E. coli* such as JM109, DH5α, HB101, or XL1-Blue, the expression vector to be used essentially has a promoter that can be efficiently expressed in *E. coli*, for example, lacZ promoter (Ward et al., Nature, (1989) 341, 544-546; FASEB J., (1992) 6, 2422-2427), araB promoter (Better et al., Science, (1988) 240, 1041-1043), or T7 promoter. Examples of such vectors include, in addition to the above-described vectors, pGEX-5X-1 (from Pharmacia), “QIAexpress system” (from QIAGEN), pEGFP, and pET (in this case, the host is preferably BL21 expressing T7 RNA polymerase).

The vector may also contain a signal sequence for polypeptide secretion. For production in the periplasm of *E. coli*, the pelB signal sequence (Lei, S. P. et al., J. Bacteriol., (1987) 169, 4397), for example, may be used as the signal sequence for polypeptide secretion. The vector can be introduced into the host cells using, for example, the calcium chloride method or electroporation.

In addition to the *E. coli* expression vectors, examples of vectors for producing the antibody of the present invention include mammalian expression vectors (e.g., pcDNA3 (from Invitrogen), pEGF-BOS (Nucleic Acids. Res., 1990, 18(17), p 5322), pEF, and pCDM8), insect cell expression vectors (e.g., “Bac-to-BAC baculovairus expression system” (from GIBCO BRL) and pBacPAK8), plant expression vectors (e.g., pMH1 and pMH2), animal virus expression vectors (e.g., pHSV, pMV, and pAdexLcw), retroviral expression vectors (e.g., pZIPneo), yeast expression vectors (e.g., “Pichia Expression Kit” (from Invitrogen), pNV11, and SP-Q01), and *Bacillus subtilis* expression vectors (e.g., pPL608 and pKTH50).

For the purpose of expression in animal cells such as CHO cells, COS cells, and NIH3T3 cells, the expression vector to be used essentially has a promoter required for intracellular expression, for example, SV40 promoter (Mulligan et al., Nature, (1979) 277, 108), MMTV-LTR promoter, EF1α promoter (Mizushima et al., Nucleic Acids Res., (1990) 18, 5322), CAG promoter (Gene, (1991) 108, 193), or CMV promoter, and the expression vector preferably also has a gene for selection of transformed cells. Examples of genes for selection of transformed cells include drug resistance genes that can be distinguished by drugs (e.g., neomycin and G418). Examples of vectors having such characteristics include pMAM, pDR2, pBK-RSV, pBK-CMV, pOPRSV, and pOP13.

Furthermore, for the purpose of stable gene expression and amplification of gene copy number in cells, nucleic acid synthesis pathway-deficient CHO cells may be transfected with a vector (e.g., pCHOI) having the DHFR gene complementary thereto, and the gene may be amplified using methotrexate (MTX). For the purpose of transient gene expression, COS cells having an SV40 T antigen-expressing gene on the chromosome may be transformed with a vector (e.g., pcD) having an SV40 replication origin. A replication origin derived from polyomavirus, adenovirus, or bovine papillomavirus (BPV), for example, may also be used. Furthermore, for amplification of gene copy number in a host cell system, the expression vector may contain, as a selection marker, aminoglycoside transferase (APH) gene, thymidine kinase (TK) gene, E. coli xanthine guanine phosphoribosyl transferase (Ecogpt) gene, or dihydrofolate reductase (dhfr) gene, for example.

The antibody of the present invention thus obtained can be isolated from inside or outside the host cells (e.g., medium), and purified as a substantially pure, homogeneous antibody. There are no limitations on methods for separation and purification of the antibody, and those that are commonly used for antibody purification may be used. For example, the antibody can be separated and purified by suitably selecting and combining methods including chromatography columns, filters, ultrafiltration, salting out, solvent precipitation, solvent extraction, distillation, immunoprecipitation, SDS-polyacrylamide gel electrophoresis, isoelectric focusing, dialysis, and recrystallization.

Examples of chromatography include affinity chromatography, ion exchange chromatography, hydrophobic chromatography, gel filtration, reversed phase chromatography, and adsorption chromatography (Strategies for Protein Purification and Characterization: A Laboratory Course Manual. Ed Daniel R. Marshak et al., Cold Spring Harbor Laboratory Press, 1996). These types of chromatography can be performed using liquid phase chromatography, for example, HPLC or FPLC. Examples of columns used for affinity chromatography include Protein A columns and Protein G columns. Examples of columns using Protein A include Hyper D, POROS, and Sepharose FF (GE Amersham Biosciences). The present invention also includes antibodies that are highly purified using these purification methods.

The obtained antibody can be purified to homogeneity. For antibody separation and purification, any separation and purification methods commonly used for proteins may be used. For example, the antibody can be separated and purified by suitably selecting and combining methods including, although not limited to, chromatography columns for affinity chromatography and the like, filters, ultrafiltration, salting out, dialysis, SDS-polyacrylamide gel electrophoresis, and isoelectric focusing (Antibodies: A Laboratory Manual. Ed Harlow and David Lane, Cold Spring Harbor Laboratory, 1988). Examples of columns used for affinity chromatography include Protein A columns and Protein G columns.

One embodiment of the present invention provides a method for producing an anti-Plexin-A1 agonist antibody by using, as an antigen, a peptide consisting of residues 461-514 of SEQ ID NO: 3 in the sema domain of human Plexin-A1 or a peptide consisting of residues 459-512 of SEQ ID NO: 52 in the same domain of mouse Plexin-A1. Another embodiment of the present invention provides an anti-Plexin-A1 agonist antibody produced by the above-described method. The anti-Plexin-A1 agonist antibody can be produced using the methods already described herein or methods well known to those skilled in the art.

Use of Anti-Plexin-A1 Agonist Antibody

The anti-Plexin-A1 agonist antibody of the present invention, which exhibits a class 3 semaphorin-like activity by binding to Plexin-A1, is useful for treating and preventing diseases associated with a quantitative or qualitative decrease in function of a class 3 semaphorin, preferably Sema3A. The anti-Plexin-A1 agonist antibody of the present invention is particularly useful for treating and preventing various diseases such as autoimmune diseases including pruritus due to psoriasis and atopic dermatitis, allergic rhinitis, osteoporosis, rheumatoid arthritis, and systemic lupus erythematosus, inflammatory diseases, and tumors.

Pharmaceutical Composition

The present invention also provides a pharmaceutical composition containing the anti-Plexin-A1 agonist antibody of the present invention. As described above, the anti-Plexin-A1 agonist antibody of the present invention is useful as a prophylactic/therapeutic agent for diseases associated with a quantitative or qualitative decrease in function of a class 3 semaphorin, preferably Sema3A (e.g., autoimmune diseases including pruritus due to psoriasis and atopic dermatitis, allergic rhinitis, osteoporosis, rheumatoid arthritis, and systemic lupus erythematosus, inflammatory diseases, and tumors). Furthermore, when the anti-Plexin-A1 agonist antibody of the present invention is used as a pharmaceutical composition, it is preferably a human antibody or humanized antibody in view of antigenicity in humans, for example.

The pharmaceutical composition of the present invention may contain a pharmaceutically acceptable carrier. Examples of pharmaceutically acceptable carriers include sterilized water, saline solution, stabilizers, excipients, antioxidants (e.g., ascorbic acid), buffers (e.g., phosphoric acid, citric acid, and other organic acids), preservatives, surfactants (e.g., PEG and Tween), chelating agents (e.g., EDTA), and binders. The pharmaceutical composition of the present invention may additionally contain proteins such as low-molecular-weight polypeptides, serum albumin, gelatin, and immunoglobulins, amino acids such as glycine, glutamine, asparagine, arginine, and lysine, carbohydrates or saccharides such as polysaccharides and monosaccharides, and sugar alcohols such as mannitol and sorbitol. When the pharmaceutical composition of the present invention is formulated into injectable aqueous solutions, examples of such aqueous solutions include saline solution and isotonic solutions containing glucose or other adjuvants, such as D-sorbitol, D-mannose, D-mannitol, and sodium chloride. These aqueous solutions may be used in combination with suitable solubilizing agents, such as alcohols (e.g., ethanol), polyalcohols (e.g., propylene glycol and PEG), and nonionic surfactants (e.g., polysorbate 80 and HCO-50).

The pharmaceutical composition of the present invention can be encapsulated in microcapsules (microcapsules such as hydroxymethylcellulose, gelatin, and poly[methylmethacrylate]), or can be formulated into a colloidal drug delivery system (e.g., liposomes, albumin microspheres, microemulsions, nanoparticles, and nanocapsules), as required (see, for example, "Remington's Pharmaceutical Science 16th edition", Oslo Ed., 1980). Methods for the preparation of sustained-release drugs are also known, and can be applied to the present invention (Langer et al., J. Biomed. Mater. Res., 1981, 15: 167-277; Langer, Chem. Tech., 1982, 12: 98-105; US3773919; EP58481; Sidman et al., Biopolymers, 1983, 22: 547-556; and EP133988).

The pharmaceutical composition of the present invention can be administered to patients either orally or parenterally, preferably parenterally. Examples of forms (dosage forms) of the pharmaceutical composition of the present invention include, although not particularly limited to, injection dosage forms, nasal dosage forms, pulmonary dosage forms, percutaneous dosage forms, lyophilized dosage forms, and solution dosage forms.

Lyophilization can be performed using methods well known to those skilled in the art (Pharm. Biotechnol., 2002, 13, 109-33, Int. J. Pharm., 2000, 203(1-2), 1-60, and Pharm. Res., 1997, 14(8), 969-975). For example, lyophilization may be performed as follows: A suitable volume of the solution is dispensed into a container used for lyophilization such as a vial, and then lyophilized in a lyophilizer or freeze-dryer, or the solution is immersed in refrigerants such as acetone/dry ice and liquid nitrogen. Furthermore, the antibody preparation can be formulated into a highly concentrated solution preparation, using a method well known to those skilled in the art. For example, the membrane concentration method using a TFF membrane may be used, as described in J. Pharm. Sc., 2004, 93(6), 1390-1402.

An injectable dosage form can be systemically or locally administered by, for example, intravenous injection, intramuscular injection, intraperitoneal injection, or subcutaneous injection. The administration method can be selected as appropriate, according to the patient's age and symptoms. The dose can be selected from, for example, the range of 0.0001 to 1000 mg per kg body weight at one time. Alternatively, the dose can be selected from, for example, the range of 0.001 to 100000 mg/body per patient. However, the dose, administration method, and the like of the present invention are not limited to those described above.

A therapeutically and prophylactically effective amount of the anti-Plexin-A1 agonist antibody means an amount of the agonist that is effective for preventing, retarding, alleviating, or inhibiting symptoms or activity associated with a disease or disorder when the anti-Plexin-A1 agonist antibody is administered to a subject. The anti-Plexin-A1 agonist antibody may be administered in one or multiple doses, and may be given in combination with other pharmacological composition(s).

Kit

The present invention provides a kit for preventing and/or treating diseases associated with a quantitative or qualitative decrease in function of a class 3 semaphorin, preferably Sema3A, which kit comprises at least the anti-Plexin-A1 agonist antibody or pharmaceutical composition of the present invention. In particular, the present invention provides a kit for preventing and/or treating autoimmune diseases including pruritus due to psoriasis and atopic dermatitis, allergic rhinitis, osteoporosis, rheumatoid arthritis, and systemic lupus erythematosus, inflammatory diseases, and tumors, which kit comprises the anti-Plexin-A1 agonist antibody or pharmaceutical composition. Additionally, a syringe, an injection needle, a pharmacologically acceptable medium, an alcohol cotton cloth, plaster, instructions describing the method of use, and the like may be packaged with this kit.

The present invention also relates to use of the anti-Plexin-A1 agonist antibody or pharmaceutical composition of the present invention for the manufacture of a prophylactic and/or therapeutic agent for diseases associated with a quantitative or qualitative decrease in function of a class 3 semaphorin, preferably Sema3A. In particular, the present invention relates to use of the anti-Plexin-A1 agonist antibody or pharmaceutical composition for the manufacture of a prophylactic and/or therapeutic agent for autoimmune diseases including pruritus due to psoriasis and atopic dermatitis, allergic rhinitis, osteoporosis, rheumatoid arthritis, and systemic lupus erythematosus, inflammatory diseases, and tumors.

The present invention also relates to the anti-Plexin-A1 agonist antibody or pharmaceutical composition of the present invention for preventing and/or treating diseases associated with a quantitative or qualitative decrease in function of a class 3 semaphorin, preferably Sema3A. In particular, the present invention relates to the anti-Plexin-A1 agonist antibody or pharmaceutical composition for preventing and/or treating autoimmune diseases including pruritus due to psoriasis and atopic dermatitis, allergic rhinitis, osteoporosis, rheumatoid arthritis, and systemic lupus erythematosus, inflammatory diseases, and tumors.

The anti-Plexin-A1 agonist antibody or pharmaceutical composition of the present invention can be used in combination with other therapeutic agent(s). The anti-Plexin-A1 agonist antibody or pharmaceutical composition of the present invention may be administered simultaneously with the other therapeutic agent(s), or may be administered at a different time. Furthermore, the present invention may be implemented as a kit including a combination of the anti-Plexin-A1 agonist antibody or pharmaceutical composition of the present invention with the other therapeutic agent(s). When the anti-Plexin-A1 agonist antibody or pharmaceutical composition of the present invention is used in combination with the other therapeutic agent(s), the dose of each of these components may be set smaller, as desired, than that when any of these components is used alone.

As used herein, the embodiments expressed using the phrase "comprising . . . "
includes embodiments expressed using the phrase "essentially consisting of . . . " and embodiments expressed using the phrase "consisting of . . . ".

The contents of all patent and reference documents explicitly cited herein shall be incorporated herein by reference in their entirety.

The present invention will be further illustrated using the following examples, which are not intended to limit the present invention.

EXAMPLES

The present invention will be hereinafter described in more detail with Examples, which are not intended to restrict the present invention.

Example 1: Preparation of Semaphorin 3A Recombinant Proteins

To prepare mouse semaphorin 3A protein, gene synthesis was performed on the basis of the sequence of NCBI Reference Sequence NP_033178.2, and arginine residues (positions 552, 555, 758, 760, and 761) in the protease recognition site were converted to alanine. The signal peptide (from the N-terminus to alanine at position 20) was replaced with artificial signal peptide HMM+38 (SEQ ID NO: 7), and His-tag sequence was inserted between the artificial signal peptide and asparagine at position 21, via a glutamic acid-aspartic acid-arginine spacer. Furthermore, serine at position 771 and valine at position 772 were deleted from the C-terminus. The amino acid sequence of the prepared mouse semaphorin 3A recombinant protein is shown in SEQ ID NO: 1. The prepared gene was incorporated into an expression vector and then introduced into FreeStyle293 cells from Invitrogen for expression, and the semaphorin 3A protein was purified from the culture supernatant by affinity purification using HisTrap excel (from GE Healthcare) and gel filtration chromatography.

To prepare human semaphorin 3A protein, gene synthesis was performed on the basis of the sequence of NCBI Reference Sequence NP_006071.1, and arginine residues (positions 552, 555, 757, 759, and 760) in the protease recognition site were converted to alanine. The signal peptide (from the N-terminus to alanine at position 20) was replaced with artificial signal peptide HMM+38 (SEQ ID NO: 7), and His-tag sequence was inserted between the artificial signal peptide and asparagine at position 21, via a glutamic acid-aspartic acid-arginine spacer. FLAG tag sequence (SEQ ID NO: 5) was further inserted at the C-terminus. The amino acid sequence of the prepared human semaphorin 3A recombinant protein is shown in SEQ ID NO: 2. The prepared gene was incorporated into an expression vector and then introduced into FreeStyle293 cells from Invitrogen for expression, and the semaphorin 3A protein was purified from the culture supernatant by affinity purification using HisTrap excel (from GE Healthcare) and gel filtration chromatography.

Example 2: Construction of Evaluation System for Mouse Semaphorin 3A Activity Using Mouse Dendritic Cell Contraction as Index For evaluation of the action of the semaphorin 3A protein upon dendritic cell morphology contraction, a contraction assay using mouse bone marrow-derived dendritic cells was performed. The contraction assay was performed by the following method.

Mouse bone marrow-derived dendritic cells were prepared in accordance with the method of Inaba et al. (J Exp Med., 1992, 176(6): 1693-702). The mouse bone marrow-derived dendritic cells were suspended in RPMI1640 medium (from Nacalai Tesque) containing 10% FBS (from Moregate) and mouse GM-CSF (40 ng/mL; R&D systems), and the suspension was seeded into 96-well plates at $2\times10^4$ cells/well and then cultured at 37° C. for 12 to 24 hours. The mouse semaphorin 3A protein was diluted to a suitable concentration with 10% FBS-containing RPMI1640 medium and added to the cell culture medium, and then the mixture was further incubated at 37° C. for 5 hours. The cells were fixed by treatment with PBS containing 4% paraformaldehyde, and cell membranes were permeabilized by treatment with PBS solution containing 0.1% Triton X-100. Then, the cells were treated with Alexa Fluor 488 (registered trademark)-labeled phalloidin and DAPI-containing PBS, thereby allowing actin polymers (F-actin) and nuclei to be stained, respectively. Cell morphology images were acquired using ArrayScan VTI (Thermo Fischer Scientific Inc.). These images were analyzed using the Morphology v4 protocol of the analytical software Cellomics-vHCSTM:Scan (Thermo Fischer Scientific Inc.), and changes in the morphology of dendritic cells were quantified using the index referred to as % High Object Convex Hull Area Ratio.

After 12 to 24 hours of culture, the dendritic cells exhibited a spindle-shaped cell morphology like an extended pseudopod; however, cell contraction was induced by further culturing the dendritic cells at 37° C. for 5 hours in the presence of mouse semaphorin 3A. FIG. 1 shows the results obtained by quantifying the cell contraction, using the above-described method.

Example 3: Preparation of Biotin-Labeled Human PlexinA1

The extracellular region of human Plexin-A1 (hPlexinA1), a single-pass transmembrane protein, was prepared as follows. From hPlexinA1 gene synthesized on the basis of the amino acid sequence of NCBI Reference Sequence NP_115618.3 (SEQ ID NO: 3), the portion after alanine at position 1245 predicted as the transmembrane region was removed, and the FLAG tag sequence (SEQ ID NO: 5) was added instead. Furthermore, the signal peptide from positions 1-26 (SEQ ID NO: 6) was replaced with artificial signal peptide HMM+38 (SEQ ID NO: 7). The prepared gene encoding hPlexinA1 (SEQ ID NO: 4) was incorporated into an animal cell expression vector, and then introduced into FreeStyle293 cells (Invitrogen) using 293Fectin (Invitrogen). At this time, the gene expressing EBNA1 (SEQ ID NO: 8) was simultaneously introduced for improved expression efficiency of the gene of interest. The cells transfected with the genes in accordance with the above-described procedure were cultured for 6 days at 37° C. and 8% $CO_2$, for secretion of the protein of interest in the culture supernatant.

The cell culture medium containing hPlexinA1 of interest was filtered through a 0.22 μm bottle-top filter to obtain culture supernatant. The culture supernatant was applied to anti-FLAG antibody M2 agarose (Sigma-Aldrich) equilibrated with D-PBS(-) (Wako Pure Chem), and then FLAG peptide in D-PBS was added, thereby allowing hPlexinA1 of interest to be eluted. Then, fractions containing hPlexinA1 were separated by gel filtration chromatography using D-PBS(-)-equilibrated Superdex 200 (GE Health Care).

Soluble hPlexinA1 prepared as described above was labeled with EZ-Link NHS-PEG4-Biotin (Thermo SCIENTIFIC), thereby preparing biotin-labeled hPlexinA1.

Example 4: Production of Soluble Mouse PlexinA1 Protein

Soluble mouse PlexinA1 protein was designed on the basis of the amino acid sequence of NCBI Reference Sequence NP_032907.1 (SEQ ID NO: 52) up to the extracellular domain. The signal peptide (from the N-terminus to isoleucine at position 24) was replaced with artificial signal peptide HMM+38 (SEQ ID NO: 7), and the FLAG tag sequence (SEQ ID NO: 5) was inserted at the C-terminus. The prepared amino acid sequence is shown in (SEQ ID NO: 16). The prepared gene was incorporated into an expression vector and then introduced into FreeStyle293 cells from Invitrogen for expression, and the soluble mouse PlexinA1 protein was purified from the culture supernatant by affinity purification using anti-FLAG M2 antibody affinity gel (Sigma-Aldrich) and gel filtration chromatography.

Example 5: Production of Anti-PlexinA1 Antibodies

Rabbits were immunized by the following method to prepare anti-mouse PlexinA1 antibodies.

Rabbits were immunized as follows: Initially, the rabbits were intradermally injected with a total of 100 μg of the soluble mouse PlexinA1 protein or soluble human PlexinA1 protein in complete Freund's adjuvant (CFA). Then, the rabbits received two or more booster immunizations with 50 μg per immunization of the soluble mouse PlexinA1 protein or soluble human PlexinA1 protein in incomplete Freund's adjuvant (IFA) at an interval of 1 week or longer.

Then, tissues were collected from the immunized rabbits, and a single cell suspension was prepared. Specifically, spleens and blood were obtained from individuals having elevated serum antibody titers, and peripheral mononuclear blood cells (PBMCs) were prepared from the blood. The peripheral mononuclear blood cells were prepared using the Ficoll method. The collected spleens were treated through a cell strainer (BD Falcon) to prepare the single cell suspension. The soluble PlexinA1 protein biotinylated with PBS(-) containing 0.5% BSA was added to the cells, and the cells were suspended. The cell suspension was incubated on ice for 30 minutes. The cells were washed with PBS(-) containing 0.5% BSA to remove biotinylated soluble PlexinA1 protein unbound to the cells. MACS streptavidin beads (Miltenyi Biotec) were added to the cells, and the cells were suspended and incubated on ice. After washing, MACS streptavidin bead-bound positive cell fractions were collected using the autoMACS Pro Separator. After the addition of anti-rabbit IgG-PE to the cells and incubation on ice, cell fractions of the cell suspension having high PE fluorescence values were collected using FACSAria (BD).

Collected B cells were cultured by the following method. The collected cells were seeded into 96-well plates to which activated rabbit T cell conditioned medium and EL4 cells (European Collection of Cell Cultures) were added. The activated rabbit T cell conditioned medium is a medium prepared by culturing thymocytes collected from rabbits in RPMI-1640 containing phytohaemagglutinin (Roche), phorbol 12-myristate 13-acetate (Sigma-Aldrich), and FBS. These cells were cultured for 5 to 12 days at 37° C. and 5% $CO_2$, and then a portion of the supernatant containing secreted antibodies was collected. The rabbit antibodies in the supernatant were evaluated for their binding activity to mouse PlexinA1.

Total RNA was collected from B cells whose binding activity was confirmed, and H chain and L chain antibody variable region genes were synthesized by RT-PCR. Antibody expression vectors were prepared by ligating these genes to the rabbit antibody H chain constant region sequence (SEQ ID NO: 17) and the rabbit antibody L chain constant region sequence (SEQ ID NO: 18). H chain and L chain expression vectors derived from the same well were mixed, FreeStyle293 (Invitrogen) cells were transfected with the genes, and the antibodies were purified from the culture supernatants.

Figure 2:
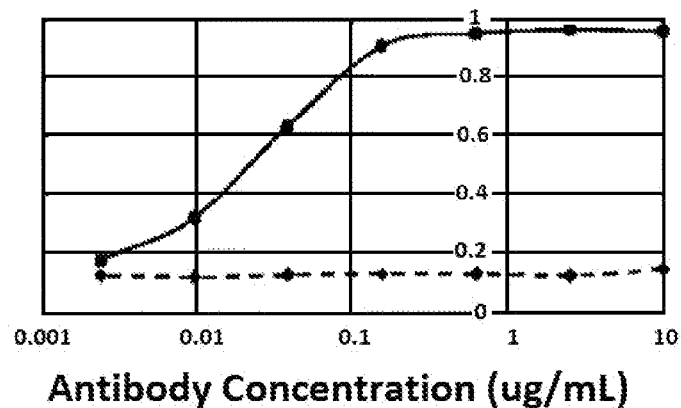
FIG. 2 illustrates plots each showing the binding activity of anti-mouse PlexinA1 antibody, PXB361b, PXB693, or PXB727, to mouse PlexinA1. The X-axis represents the antibody concentration, and the Y-axis represents the absorbance at a wavelength of 405 nm. The solid line represents binding to the Ba/F3 cell line expressing a high level of mouse PlexinA1, and the dashed line represents binding to Ba/F3 cells.
Figure 2:
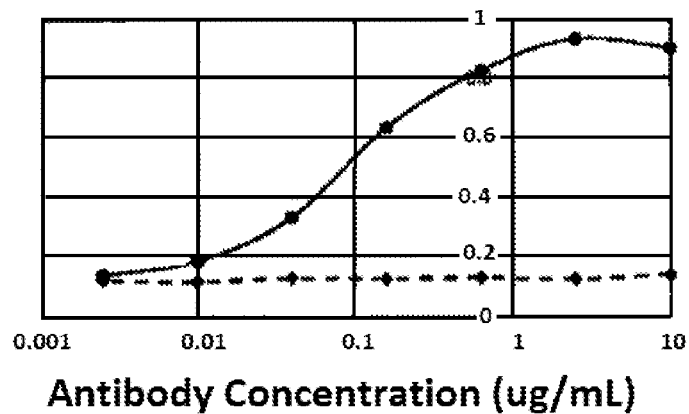
Figure 2:
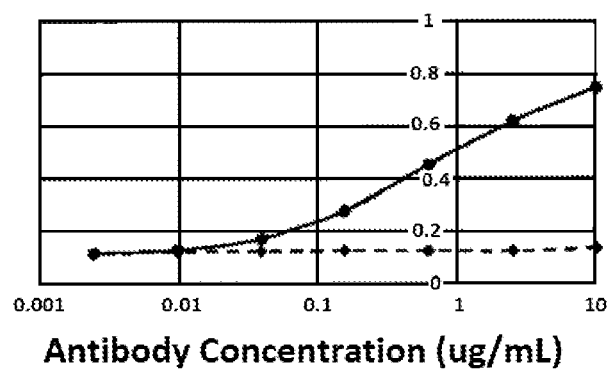
Figure 3:
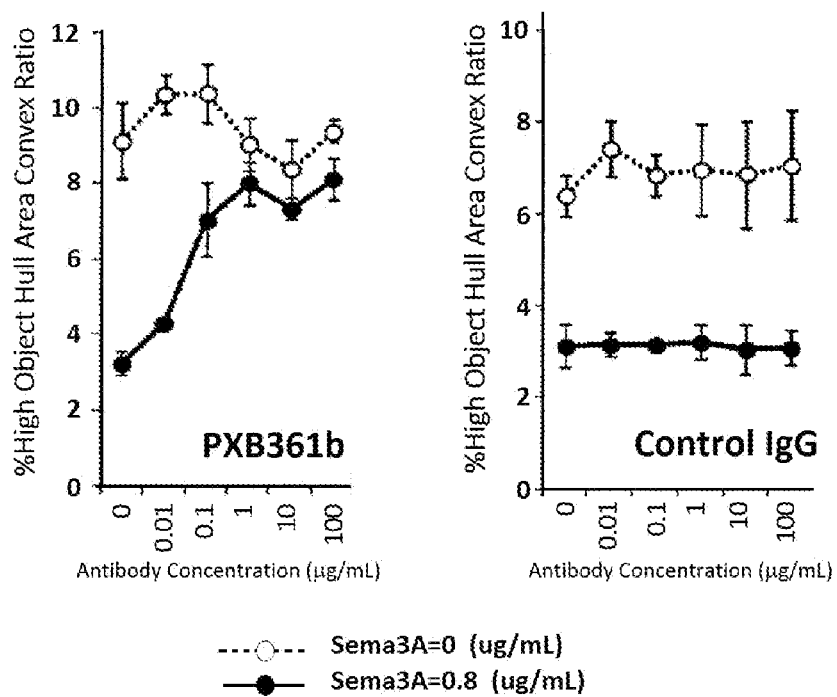
FIG. 3 illustrates plots each showing dose-dependent antagonistic activity of a control antibody or anti-PlexinA1 antibody (rabbit IgG) at concentrations of 0 to 100 µg/mL against semaphorin 3A-dependent mouse bone marrow-derived dendritic cell contraction.

Using the purified antibodies, antigen binding activities were evaluated by ELISA using a mouse PlexinA1-expressing cell line. The results are shown in FIG. 2. Anti-mouse PlexinA1 antibodies PXB361b, PXB693, and PXB727 were confirmed to be specifically bound to the mouse PlexinA1-expressing cell line in an antibody concentration-dependent manner. The amino acid sequences of the H chain and L chain variable regions of PXB361b are shown in SEQ ID NOS: 19 and 20, respectively, the amino acid sequences of the H chain and L chain variable regions of PXB693 are shown in SEQ ID NOS: 41 and 42, respectively, and the amino acid sequences of the H chain and L chain variable regions of PXB727 are shown in SEQ ID NOS: 43 and 44, respectively. Antagonistic activity of an anti-mouse PlexinA1 antibody was evaluated using the semaphorin 3A-dependent mouse bone marrow-derived dendritic cell contraction assay system described in Example 2. The results are shown in FIG. 3. The obtained anti-mouse PlexinA1 antibody PXB361b was observed to suppress dendritic cell contraction in a concentration-dependent manner, and was confirmed to exhibit an antagonistic activity to suppress semaphorin 3A signaling.

Example 6: Evaluation of Antibodies by Cell ELISA

The antibodies obtained above were subjected to cell ELISA by the following procedure. Initially, 384-well plates were prepared, and mouse PlexinA1-expressing Ba/F3 cells and Ba/F3 cells (see Example 11) were each captured onto the bottom of different wells. After washing each well of the plates with PBS, the prepared antibodies were added at 20 μL/well, and the mixture was allowed to stand at room temperature for 1 hour. Then, each well was washed with 0.05% Tween 20-PBS, HRP-labeled anti-rabbit IgG antibody (Betyl, A120-101P) diluted 10000 times with 2% FBS-PBS was added at 20 μL/well, and the mixture was allowed to stand at room temperature for 1 hour. After washing each well of the plates with 0.05% Tween 20-PBS, the substrate solution (ABTS peroxidase substrate system) was dispensed at 20 L/well to develop color for 1 hour at room temperature. Then, binding of the antibodies to mouse PlexinA1 was confirmed by measuring absorbance at 405 nm using SpectraMax from Molecular Devices, LLC.

Example 7: Production of Human Antibody Naive Library

Using Poly A RNA prepared from human PBMC or commercially available human Poly A RNA as a template, a gene library of antibody heavy chain variable regions and a gene library of antibody light chain variable regions were amplified by PCR.

The prepared gene library of antibody heavy chain variable regions and gene library of antibody light chain variable regions were combined, and then inserted into a phagemid vector to construct a human antibody phage display library displaying Fab domains consisting of human antibody sequences. For the construction method, reference was made to Methods Mol Biol., (2002) 178, 87-100. The above-described library was constructed using phage display library sequences in which a trypsin cleavage sequence was inserted into the linker region connecting the Fab and phage pIII protein of the phagemid, as well as between the N2 and CT domains of the helper phage pIII protein gene.

Example 8: Acquisition of Antibody Fragments That Bind to hPlexinA1 from Human Antibody Naive Library by Bead Panning Phages were produced using *E. coli* carrying the constructed phagemids for phage display. A population of phages precipitated by adding 2.5M NaCl/10% PEG to the culture medium of *E. coli* used for the phage production was diluted with TBS to obtain phage library solution. This is followed by the addition of BSA and $CaCl_2$ to the phage library solution, thereby adjusting the phage library solution to final concentrations of 4% BSA and 1.2 mM calcium ions. For panning, reference was made to common panning methods using antigens immobilized onto magnetic beads (J. Immunol. Methods., (2008) 332 (1-2), 2-9; J. Immunol.

Methods., (2001) 247 (1-2), 191-203; Biotechnol. Prog., (2002) 18(2) 212-20; Mol. Cell Proteomics, (2003) 2 (2), 61-9). NeutrAvidin coated beads (Sera-Mag SpeedBeads NeutrAvidin-coated) or streptavidin coated beads (Dynabeads M-280-Streptavidin) were used as the magnetic beads.

Specifically, 250 pmol of the above-described biotin-labeled hPlexinA1 was added to the prepared phage library solution, thereby allowing the phage library solution to contact the antigen at room temperature for 60 minutes. BSA-blocked magnetic beads were added, and the antigen-phage complex was bound to the magnetic beads at room temperature for 15 minutes. The beads were washed three times with 1 mL of 1.2 mM $CaCl_2$/TBST (TBST containing 1.2 mM $CaCl_2$), and then further washed twice with 1 mL of 1.2 mM $CaCl_2$/TBS (TBS containing 1.2 mM $CaCl_2$). Then, 0.5 mL of 1 mg/mL trypsin was added to the beads and the beads were suspended at room temperature for 15 minutes, and then immediately, the beads were separated using a magnetic stand to collect phage solution. The collected phage solution was added to 10 mL of E. coli strain ER2738 in the logarithmic growth phase (OD600: 0.4-0.7). Culturing the E. coli cells by stirring gently at 37° C. for 1 hour infected the E. coli cells with the phages. The infected E. coli cells were seeded into 225×225 mm plates. Then, the phages were collected from the culture medium of the seeded E. coli cells, thereby preparing phage library solution, which was used for a second round of panning.

The second round of panning involved adding 40 pmol of the biotin-labeled antigen to the prepared phage library solution, and performing the same procedure as that in the first round of panning, thereby preparing phage library solution. This prepared solution was used to perform a third round of panning.

The third round of panning involved adding 10 pmol of the biotin-labeled antigen to the prepared phage library solution, and performing the same procedure as that in the first and second rounds of panning to collect the seeded E. coli cells.

Example 9: Evaluation by Phage ELISA

Phage-containing culture supernatants were collected in accordance with a conventional method (Methods Mol. Biol., (2002) 178, 133-145) from the single colonies of E. coli obtained by the above-described method.

The phage-containing culture supernatants, to which skim milk and CaC12 were added, were subjected to ELISA by the following procedure. StreptaWell 96 microtiter plates (Roche) were coated overnight with 100 µL of PBS containing the biotin-labeled antigen. Each well of the plates was washed with PBST to remove the antigen, and then the well was blocked with 250 µL of 0.02% skim milk-TBS for 1 hour or longer. The prepared culture supernatants were added to each well from which 0.02% skim milk-TBS was removed, and the plates were allowed to stand at 37° C. for 1 hour, thereby allowing phage-displayed antibodies to be bound to the antigen present in each well. After washing with 1.2 mM CaC12/TBST, HRP-conjugated anti-M13 antibody (GE Healthcare, 27-9421-01) diluted 25,000× with 1.2 mM $CaCl_2$/TBS was added to each well, and the well was incubated for 1 hour. After washing with 1.2 mM $CaCl_2$/TBST, TMB solution (LifeTechnologies, 00-2023) was added to each well, the color development reaction of the solution in each well was stopped by the addition of sulfuric acid, and then the color was measured on the basis of absorbance at 450 nm.

The clones subjected to phage ELISA as described above were amplified using specific primers, and nucleotide sequence analysis was performed on these genes. Then, on the basis of the results of phage ELISA and sequence analysis described above, the pool of antibody fragments after the third round of panning was converted to full-length human antibodies for further evaluation.

Example 10: Conversion of Antibody Fragments to Full-Length Antibodies, Expression and Purification The phagemids were extracted from the E. coli cells collected during the third round of panning, using NucleoBond Xtra Midi Plus (MACHEREY-NAGEL, 740412.50). Then, the antibody variable regions were cut by the restriction enzyme treatment, and ligated to a cassette vector in which an antibody constant region was introduced into a vector carrying EF1 promoter and the replication origin OriP of EBNA1. E. coli DH5α (TOYOBO, DNA-903) was transformed with the ligation products, and full-length antibody plasmids for expression in animal cells were extracted from the obtained single colonies.

Expression of the antibodies was performed using the following method. The human embryonic kidney cell-derived FreeStyle 293-F cell line (Invitrogen) was suspended in FreeStyle 293 Expression Medium (Invitrogen), and the cells were seeded at 190 µL per well of 96-well plates at a cell density of $5.0 \times 10^4$ cells/well. Each of the prepared plasmids was introduced into the cells by lipofection. The cells were cultured for 5 days in a $CO_2$ incubator (37° C. and 8% $CO_2$) for secretion of antibodies in the culture supernatants. The secreted antibodies in the culture supernatants were purified using Multi screen HTS GV (Millipore, MSGVN2250).

Example 11: Construction of Human and Mouse PlexinA1-Expressing Cells

Antigen-expressing cell lines were constructed by the following method. A plasmid was prepared by inserting, into pCXND3 vector carrying CAG promoter and a neomycin-resistant gene, a cDNA constructed to express the portion of human PlexinA1 (NCBI Reference Sequence NP_115618.3) or mouse PlexinA1 (NCBI Reference Sequence NP_032907.1) up to the transmembrane region (up to position 1300 in human PlexinA1 and position 1290 in mouse PlexinA1) in which the signal peptide was replaced with HMM+38 (SEQ ID NO: 7), as a protein C-terminally fused with the Myc tag (SEQ ID NO: 51). The amino acid sequence of the prepared human PlexinA1 is shown in SEQ ID NO: 15, and the amino acid sequence of mouse PlexinA1 is shown in SEQ ID NO: 37.

The prepared plasmid was cleaved with restriction enzyme PvuI into a linear form, and then introduced into Ba/F3 cells by electroporation using GenePulserX cell (Bio-Rad). After the introduction, the cells were seeded into 96-well plates by the limiting dilution method, and selected using G418. After 1 to 2 weeks, the selected cells were visually observed for single colony formation in the wells, and a portion of single colony-forming cells were collected and subjected to Western blot analysis using the Myc tag antibody. In parallel with this, the cells were captured onto 96-well plates and fixed with 4% paraformaldehyde, acetone, and methanol, and then ELISA was used to examine whether the Myc tag antibody reacts to the cells having holes in the cell membranes. These results of Western blot analysis and ELISA established that human PlexinA1 and mouse PlexinA1 are expressed in the Ba/F3 cells.

Example 12: Evaluation by Cell ELISA

The antibody supernatants obtained in Example 10 were subjected to cell ELISA by the following procedure. Initially, 384-well plates were prepared, and human PlexinA1- and mouse PlexinA1-expressing Ba/F3 cells were each captured onto the bottom of different wells. After washing each well of the plates with PBS, the prepared antibody supernatants were added at 20 μL/well and allowed to stand at room temperature for 1 hour. Then, each well was washed with 1 M Hepes (pH 7.4), HRP-labeled anti-human IgG antibody (Invitrogen, AHI0304) diluted 5000× with TBS was added at 20 μL/well, and the mixture was allowed to stand at room temperature for 1 hour. After washing each well of the plates with 1 M Hepes (pH 7.4), the substrate solution (ABTS peroxidase substrate system) was dispensed at 20 μL/well to develop color for 1 hour at room temperature. Then, binding of the antibodies to human PlexinA1 and mouse PlexinA1 was confirmed by measuring absorbance at 405 nm using SpectraMax from Molecular Devices, LLC.

Figure 4:
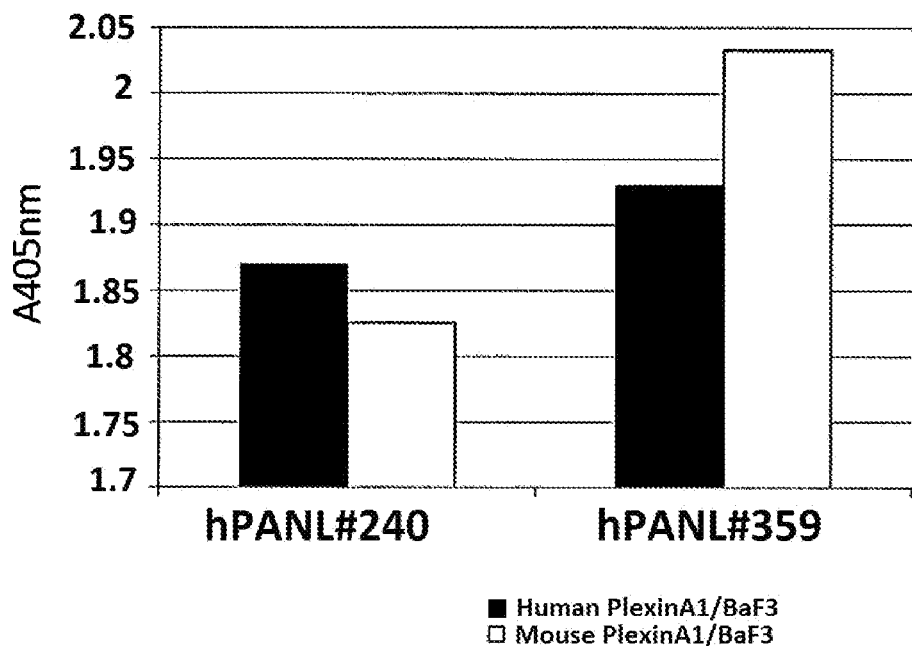
FIG. 4 illustrates a plot showing absorbance values of binding responses of antibodies bound to BaF3 cells expressing human PlexinA1 or mouse PlexinA1 on the cell membrane surface.

Antibodies having an absorbance of 0.2 or more for human PlexinA1/BaF3 and having an absorbance of 0.2 or more for mouse PlexinA1/BaF3 were selected, and subjected to the in vitro activity evaluation assay described below. By way of example, antibodies exhibiting the absorbance values shown in FIG. 4 and Table 1 were selected as human/mouse cross-reactive PlexinA1 antibodies (hPANL #240 and hPANL #359). The vertical axis in FIG. 4 represents absorbance values (405 nm) measured by cell ELISA, and the values are shown in Table 1. The amino acid sequence of an H chain of hPANL #240 is shown in SEQ ID NO: 9, and the amino acid sequence of an L chain of hPANL #240 is shown in SEQ ID NO: 10 (see also Table 2).

TABLE 1

| A405 nm | Human PlexinA1/BaF3 | Mouse PlexinA1/BaF3 |
|---|---|---|
| hPANL#240 | 1.8706 | 1.8259 |
| hPANL#359 | 1.9304 | 2.033 |

TABLE 2

| | |
|---|---|
| hPANL#240<br>H Chain<br>(SEQ ID NO: 9) | QVQLQQSGPGLVKPSQTLSLTCAISGD<br>SLSSTSAAWNWIRQSPSGGLEWLGRTY<br>YRSKWYNDYAVSVKSRITINPDTSKNQ<br>FSLQLNSVTPEDTSVYYCARDRGYYNG<br>VDVWGQGTMVTVSSASTKGPSVFPLAP<br>SSKSTSGGTAALGCLVKDYFPEPVTVS<br>WNSGALTSGVHTPPAVLQSSGLYSLSS<br>VVTVPSSSLGTQTYICNVNHKPSNTKV<br>DKKVEPKSCDKTHTCPPCPAPELLGGP<br>SVFLFPPKPKDTLMISRTPEVTCVVVD<br>YSHEDPEVKFNWYYDGVEVHNAKTKPR<br>EEQYNSTYRVVSVLTVLHQDWLNGKEY<br>KCKVSNKALPAPIEKTISKAKGQPREP<br>QVYTLPPSRDELTKNQVSLTCLVKGFY<br>PSDIAVEWESNGQPENNYKTIPPVLDS<br>DGSFFLYSKLTVDKSRWQQGNVFSCSV<br>MHEALHNHYTQKSLSLSP |
| hPANL#240<br>L Chain<br>(SEQ ID NO: 10) | SYELTQPPSVSVSPGQTASITCSGDKL<br>GDKYASWYQQRPGQSPLLVIYQDNKRP<br>SGIPQRFSGSNSGNTATLTISGTQAMD<br>EADYFCQAWDSGTFVFGTGTKVTILRQ<br>PKANPTVTLFPPSSEELQANKATLVCL<br>ISDFYPGAVTVAWKADGSPVKAGVEIT<br>KPSKQSNNKYAASSYLSLTPEQWKSHR<br>SYSCQVTHEGSTVEKTVAPTECS |

Example 13: Affinity Maturation of Selected Antibody hPANL #359 selected in Example 12 was subjected to affinity maturation, using a method known to those skilled in the art. Specifically, with reference to, for example, (Biochemical and Biophysical Research Communications, (2000), 275, 2, 553-557), a new library was prepared by substituting the light chain of the antibody with a human light chain library, and then the library was subjected to two rounds of the panning procedure against biotin-labeled human PlexinA1. Phage-containing culture supernatants were collected from the obtained single colonies of E. coli, and subjected to phage ELISA in the same manner as described above.

Nucleotide sequence analysis was performed on E. coli cells of the clones that showed color development in the antigen-immobilized wells by phage ELISA. Furthermore, the phagemids were extracted from the E. coli cells, and introduced into an animal cell expression vector. Then, the vector was introduced into the FreeStyle 293-F cell line (Invitrogen) by lipofection to obtain culture supernatants in which antibodies were secreted.

Example 14: Confirmation of Binding Capacities of Acquired Antibodies

Binding capacities of the antibody culture supernatants prepared in Example 13 to human PlexinA1 were confirmed using OctetRED384 (ForteBIO). Specifically, the antibody culture supernatants diluted to 1.25 μg/mL were immobilized onto Protein G biosensors (ForteBIO), and human PlexinA1 was subsequently applied thereto, for measurement of binding responses between the antibodies immobilized onto the biosensors and the antigen.

As a result, several types of antibodies confirmed to be bound to human PlexinA1 were acquired. 359B2-2-3-6 (H chain, SEQ ID NO: 11, L chain, SEQ ID NO: 12) is an antibody having an improved binding capacity compared to the parent antibody before affinity maturation.

TABLE 3

| | |
|---|---|
| 359B2-2-3-6<br>H Chain<br>(SEQ ID NO: 11) | QVQLVQSGAEVKKPGASVKVSCKASGY<br>TFTSYYMHWVRQAPGQGLEWMGIINPS<br>CGSTSYAQKFQGRVTMTRDTSTSTVYM<br>ELSSLRSEDTAVYYCARAPGHYYYGMD<br>VWGQGTTVTVSSASTKGPSVFPLAPSS<br>KSTSGGTAALGCLVKDYFPEPVTVSWN<br>SGALTSGVNTFPAVLQSSGLYSLSSVV<br>TVPSSSLGTQTYICNVNHKPSNTKVDK<br>KVEPKSCDKTHTCPPCPAPELLGGPSV<br>FLFPPKPKDTLMISRTPEVTCVVVDVS<br>HEDPEVKFNWYVDGVEVHNAKTKPREE<br>QYNSTYRVVSVLTVLHQDWLNGKEYKC<br>KVSNKALPAPIEKTISKAKGQPREPQV<br>YTLPPSRDELTKNQVSLTCLVKGFYPS<br>DIAVEWESNGQPENNYKTTPPVLDSDG<br>SFFLYSKLTVDKSRWQQGNVFSCSVMH<br>EALHNHYTQKSLSLSP |
| 359B2-2-3-6<br>L Chain<br>(SEQ ID NO: 12) | SYELTQPPSVSVSPGQTASITCSGDKL<br>EDKYASWYQLKPGHSPVLVIYQDSKRP<br>SGIPERFSGSNSGNTATLTISGTQAMD<br>EADYYCRAWDSNTGDVVFGGGTKLTVL<br>RQPKAAPSVTLFPPSSEELQANKATLV<br>CLISDFYPGAVTVAWKADSSPVKAGVE<br>TTTPSKQSNNKYAASSYLSLTPEQWKS<br>HRSYSCQVTHEGSTVEKTVAPTECS |

Furthermore, mouse chimeric antibodies (hPANL #240-mFc: H chain, SEQ ID NO: 13, L chain, SEQ ID NO: 10; 359 B-2-2-3-6-mFc: H chain, SEQ ID NO: 14, L chain SEQ ID NO: 12) produced by the below-described method from these antibodies acquired from the human antibody naive library, as well as immunized rabbit-derived mouse chimeric antibodies (PXB693-mFc: H chain, SEQ ID NO: 45, L-chain, SEQ ID NO: 46; PXB727-mFc: H-chain, SEQ ID NO: 47, L-chain, SEQ ID NO: 48; PXB361 b-mFc: H chain, SEQ ID NO: 49, L chain, SEQ ID NO: 50) were evaluated for their human/mouse cross-reactivity, using OctetRED384 (ForteBIO). Note that the L chains of the antibodies derived from the human antibody naive library were not chimerized.

Figure 5:
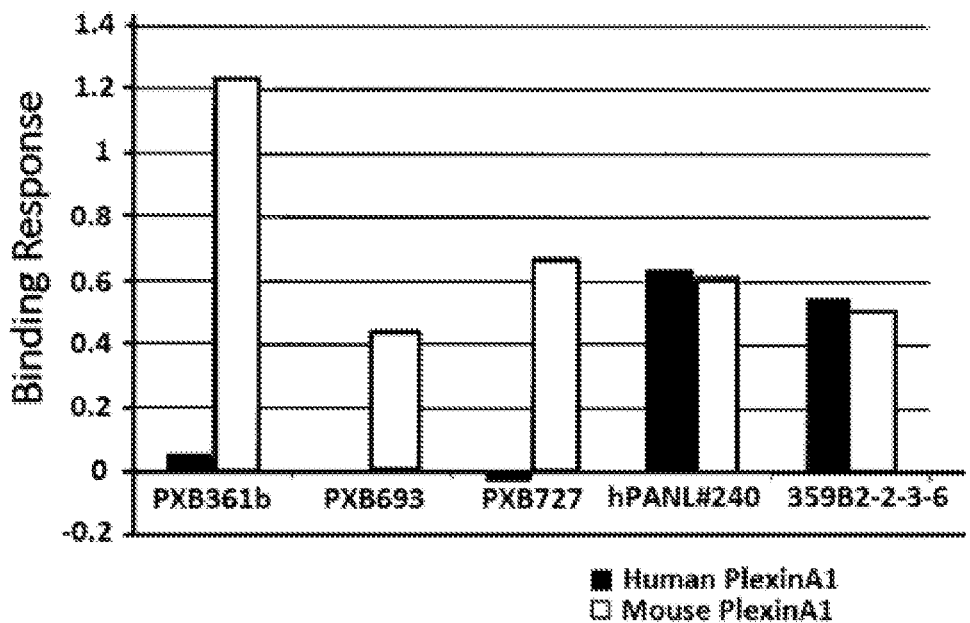
FIG. 5 illustrates a plot showing binding responses measured by immobilizing mouse chimeric antibodies hPANL #240-mFc, 359B-2-2-3-6-mFc, PXB693-mFc, PXB727-mFc, and PXB361b-mFc onto Protein G biosensors, and applying human PlexinA1 and mouse PlexinA1 thereto.

Specifically, the antibodies adjusted to 10 μg/mL by 10× diluted HBS-EP+ (GE healthcare, BR-1006-69) were immobilized onto Protein G biosensors (ForteBIO), and human and mouse PlexinA1 adjusted to 260 nM with HBS-EP+ were applied thereto. The Protein G biosensors were regenerated using 10 mmol/L Glycine-HCl, pH 1.5 (GE Healthcare, BR-1003-54). After the measurement, analytical software Data analysis 7.0 (ForteBIO) was used to compute amounts of binding (FIG. 5). These results showed that PXB361b, PXB693, and PXB727 exhibit binding affinities only for mouse PlexinA1, and hPANL #240 and 359B2-2-3-6 are human/mouse cross-reactive antibodies. In FIG. 5, the vertical axis represents amounts of binding to human and mouse PlexinA1.

TABLE 4

| | |
|---|---|
| hPANL#240-mFc<br>H Chain<br>(SEQ ID NO: 13) | QVQLQQSGPGLVKPSQTLSLTCAISG<br>DSLSSTSAAWNWIRQSPSGGLEWLGR<br>TYYRSKWYNDYAVSVKSRITINPDTS<br>KNQFSLQLNSVTPEDTSVYYCARDRG<br>VYNGVDYWGQGTMVTVSSAKTTAPSV<br>YPLAPYCGDTTGSSVTLGCLVKGYFP<br>EPVTLTWNSGSLSSGVHTFPAVLQSD<br>LYTLSSSVTVTSSTWPSQSITCNVAH<br>PASSTKVDKKIEPRGPTIKPCPPCKC<br>PAPNLRRGPKVFIFPPKIKDVLMISL<br>SPIVTCVVVDVSEDDPDVQISWFVNN<br>VEVHTAQTQTMREDYNSTLRVVSALP<br>IQHQDWMSGKEFKCKVNNKDLPAPIE<br>RTISKPKGSVRAPQVYVLPPPEEEMT<br>KKQVTLTCMVTDFMPEDIYVEWTNNG<br>KTELNYKNTEPVLDSDGSYFMYSKLR<br>VEKKNWYERNSYSCSVVHEGLHNHHT<br>TKSFSRTPGK |
| 359B2-2-3-6-mFc<br>L Chain<br>(SEQ ID NO: 14) | QVQLVQSGAEVKKPGASVKVSCKASG<br>YTFTSYYMHWVRQAPGQGLEWMGIIN<br>PSGGSTSYAQKFQGRYTMTRDTSTST<br>YYMELSSLRSEDTAVYYCARAPGHYY<br>YGMDVWGQGTTVTVSSAKTTAPSVYP<br>LAPVCGDTTGSSVTLGCLVKGYFPEP<br>VTLTWNSGSLSSGVHTFPAVLQSDLY<br>TLSSSVTVTSSTWPSQSITCNVAHPA<br>SSTKVDKKIEPRGPTIKPCPPCKCPA<br>PNLRNGPKVFIFPPKIKDVLMISLSP<br>IVTCVVVDVSEDDPDVQISWFVNNVE<br>VHTAQTQTHREDYNSTLRVVSALPIQ<br>HQDWMSGKEFKCKVNNKDLPAPIERT<br>ISKPKGSVRAPQVYVLPPPEEEMTKK<br>QVTLTCMVTDFMPEDIYVEWTNNGKT<br>ELNYKNTEPVLDSDGSYFMYSKLRVE<br>KKNWVERNSYSCSVVHEGLHNHHYYK<br>SFSRTPGK |

Example 15: Production of Mouse Chimeric Antibodies

The heavy chain variable regions of the antibodies were amplified with specific primers, and the amplified products were cloned, together with mouse heavy chain constant region fragments, into a restriction enzyme-linearized animal cell expression vector, using In-Fusion HD Cloning Kit (Takara Bio). A mouse IgG2a-derived heavy chain constant region was used for hPANL #240, 359B-2-2-3-6, PXB693, and PXB727, and a mouse IgG1-derived heavy chain constant region was used for PXB361b.

Furthermore, the light chain variable regions of PXB693, PXB727, and PXB361b were amplified with specific primers, and the amplified products were cloned, together with a mouse light chain constant region, into a restriction enzyme-linearized animal cell expression vector, using In-Fusion HD Cloning Kit (Takara Bio).

The heavy chain expression vectors carrying the mouse constant region and the human light chain sequence expression vectors or the light chain expression vectors carrying the mouse constant region were introduced into the FreeStyle 293-F cell line (Invitrogen) by lipofection. The cells were cultured for 5 days in a $CO_2$ incubator (37° C., 8% $CO_2$, 90 rpm), and then the antibodies were purified from the culture supernatants obtained above by a method known to those skilled in the art, using rProtein A Sepharose™ Fast Flow (Amersham Biosciences). Absorbance at 280 nm was measured using a spectrophotometer for the purified antibody solutions, and antibody concentrations were computed from the measured values, using extinction coefficients computed by the PACE method (Protein Science, (1995) 4, 2411-2423).

Example 16: Epitope Binning

Regarding the five types of mouse chimeric antibodies (PXB361b-mFc, PXB693-mFc, PXB727-mFc, hPANL #240-mFc, and 359B2-2-3-6-mFc) prepared in Example 15, it was verified whether any pair of these antibodies can bind to the antigen, mouse PlexinA1, without competing, by using Octet RED 384 (ForteBIO). The five types of mouse chimeric antibodies can be grouped according to epitope, by verifying the competition pattern. This was accomplished with reference to a common epitope binning technique (mAbs (2012) 5: 2, 270-278).

Specifically, the five types of antibodies (assumed as antibodies A to E) adjusted to 10 μg/mL as "Ab1" were immobilized onto five Protein G biosensors, respectively. Mouse PlexinA1 adjusted to 260 nM was applied thereto. Then, the antibody A as "Ab2" was bound to the five sensors on which the five types of "Ab1" were immobilized. After regeneration of the Protein G biosensors using 10 mmol/L Glycine-HC1, pH 1.5 (GE Healthcare, BR-1003-54), the five types of "Ab1" were again immobilized onto the sensors, the antigen was applied thereto, and then the antibody B as "Ab2" was bound to the sensors. This procedure was repeated until the antibody E, while regenerating the biosensors.

Analytical software Data analysis 7.0 (ForteBIO) was used to compute the parameters. If the antibodies A and B compete with each other, no binding response of the antibody B to the antigen bound to the immobilized antibody A is observed. If the antibodies A and B do not compete with each other, an elevated binding response of the antibody B to the antigen bound to the immobilized antibody A can be confirmed.

Figure 6:
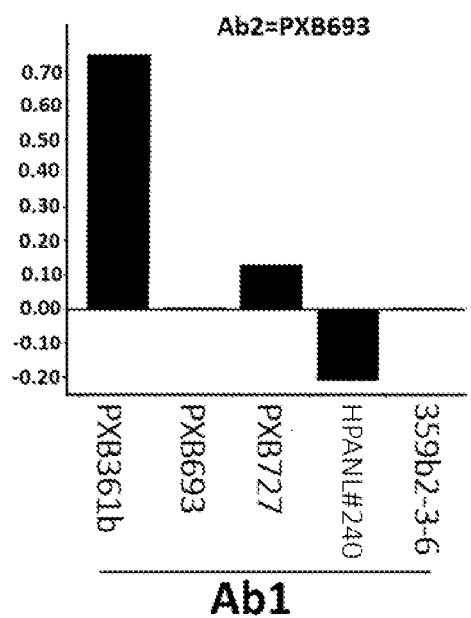
FIG. 6 illustrates a plot showing the results obtained by immobilizing PXB693 onto Protein G biosensors and applying antigen, and then further applying the various antibodies, thereby evaluating whether the various antibodies compete for binding. Competition ratios of the various antibodies relative to PXB693 are shown.

The competition ratio of the antibody B relative to the antibody A (FIG. 6) was evaluated as the value determined by dividing the value obtained by subtracting {the binding response of the antigen bound to "Ab1; antibody A"} from {the binding response 200 seconds after the binding of "Ab2; antibody B" to the antigen}, by {the immobilization response of "Ab1; antibody B" to the Protein G biosensor}. PXB693 was used as Ab2.

The results revealed that PXB361b acquired as an antagonist antibody does not compete with the other four antibodies acquired as agonist antibodies. Furthermore, the four types of agonist antibodies (PXB693, PXB727, hPANL #240, and 359B2-2-3-6) were shown to compete with one another.

Example 17: Construction of Evaluation System for Semaphorin 3A Activity Against U87-MG Cells by Using xCELLigence System An assay was performed using the xCELLigence system (ACEA) to evaluate the action of semaphorin 3A protein in human cells. The xCELLigence system can evaluate morphological changes, migration, and the like, on the basis of electrical impedance produced on the cell adhesion surface and on microelectrodes arranged on the bottom of a special plate. The assay was performed by the following method.

Figure 7:
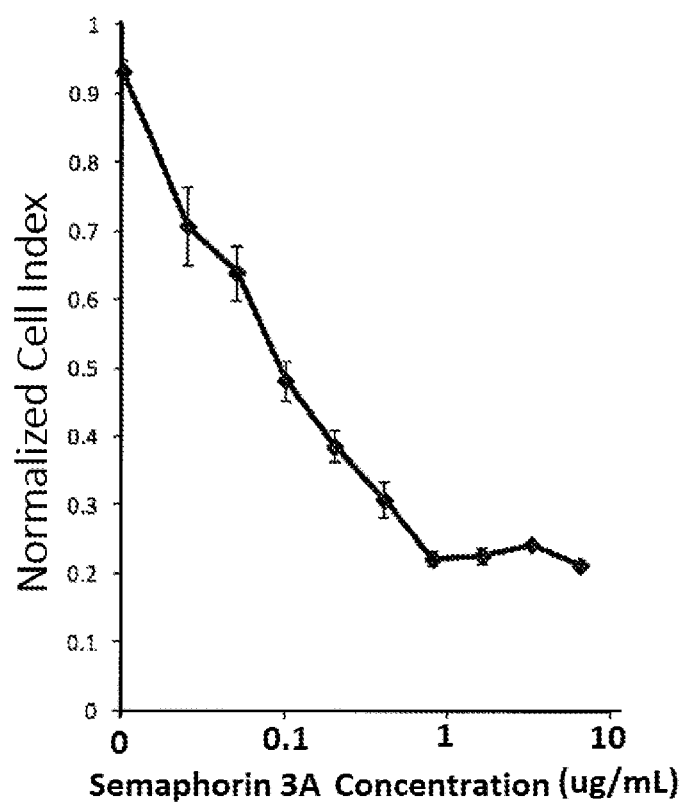
FIG. 7 illustrates a plot showing changes in Cell index value upon 1-hour stimulation of U87-MG cells with human semaphorin 3A using the xCELLigence system.

U87-MG cells of a human glioblastoma cell line cultured in 5% FBS-containing EMEM medium (ATCC) were used. U87-MG cells were seeded at a density of $1\times10^4$ cells/well in the E-plate 96 (ACEA), which is a special plate for the xCELLigence system, and cultured at 37° C. for 12 to 24 hours. Then, human semaphorin 3A was diluted with 5% FBS-containing EMEM medium to a suitable concentration and added to the cell culture medium, and the Cell index value for each well was measured by the xCELLigence system (ACEA). Cell index values measured 1 hour after the addition of semaphorin 3A are shown in FIG. 7. A semaphorin 3A-induced concentration-dependent decrease in Cell index value was confirmed. Note that the Cell index value was used as an index of the size of cell morphology and/or the cell adhesion strength.

Example 18: Evaluation of Activities of Anti-Mouse PlexinA1 Antibodies

Figure 8:
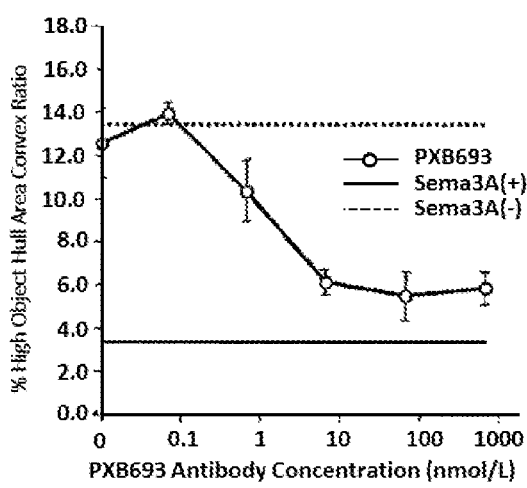
FIG. 8 illustrates plots showing dose-dependent semaphorin 3A-like agonistic activities of anti-PlexinA1 antibodies for mouse bone marrow-derived dendritic cell contraction. Sema3A(+) represents values measured with the addition of 0.8 µg/mL of mouse semaphorin 3A, and Sema3A(−) represents values measured without the addition of mouse semaphorin 3A.
Figure 8:
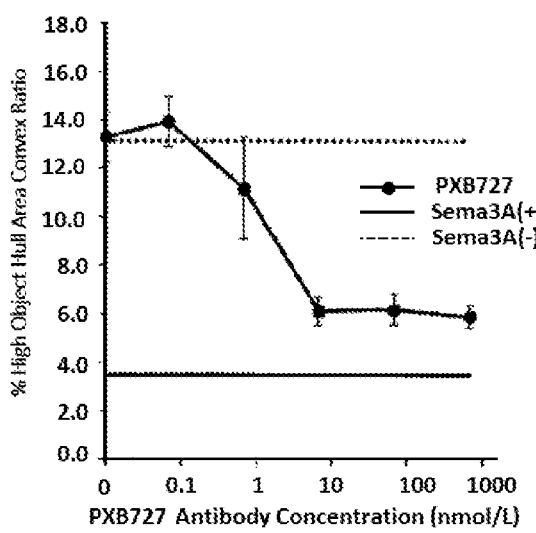
Figure 8:
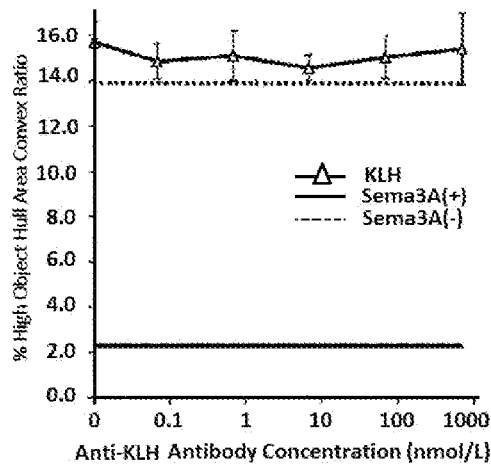
Figure 8:
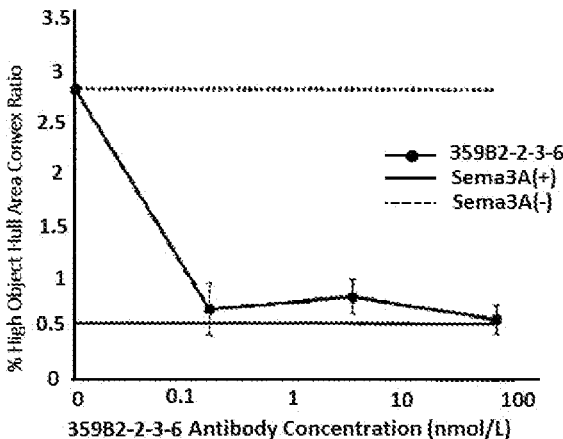

Activities of the prepared anti-mouse PlexinA1 antibodies and anti-human/mouse PlexinA1 antibody were evaluated using the mouse semaphorin 3A-dependent mouse bone marrow-derived dendritic cell contraction assay system described in Example 2. Specifically, mouse bone marrow-derived dendritic cells were seeded into 96-well plates at $2\times10^4$ cells/well in RPMI1640 medium containing FBS and mouse GM-CSF, and cultured at 37° C. for 12 to 24 hours. The anti-mouse PlexinA1 antibodies and anti-human/mouse PlexinA1 antibody, an anti-KLH antibody of the same isotype as a control, and mouse semaphorin 3A were diluted to a suitable concentration with 10% FBS-containing RPMI1640 medium, and then added to the cell culture medium and the mixtures were cultured at 37° C. for 5 hours. Then, dendritic cell contraction was quantified using the method described in Example 2, and then evaluated. The results are shown in FIG. 8. The anti-mouse PlexinA1 antibodies (PXB693-mFc and PXB727-mFc) and the anti-human/mouse PlexinA1 antibody (359B2-2-3-6-mFc) were confirmed to promote dendritic cell contraction in a concentration-dependent manner, and exhibit the same activity as semaphorin 3A signaling.

Figure 9:
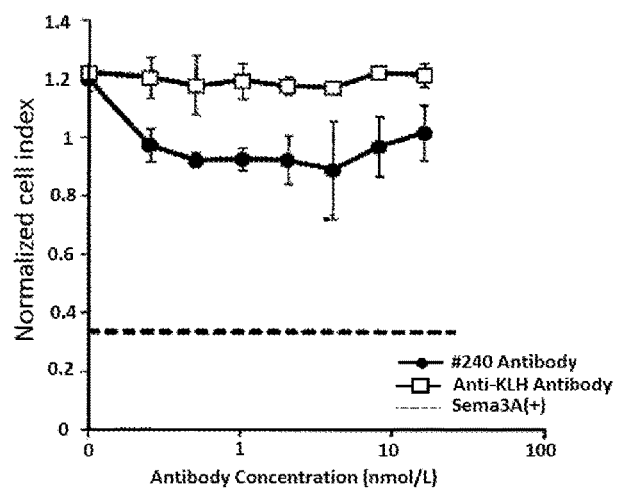
FIG. 9 illustrates plots showing semaphorin 3A-like agonistic activities of anti-PlexinA1 antibodies against U87-MG cells. Sema3A(+) represents values measured with the addition of 1.6 µg/mL of human semaphorin 3A.
Figure 9:
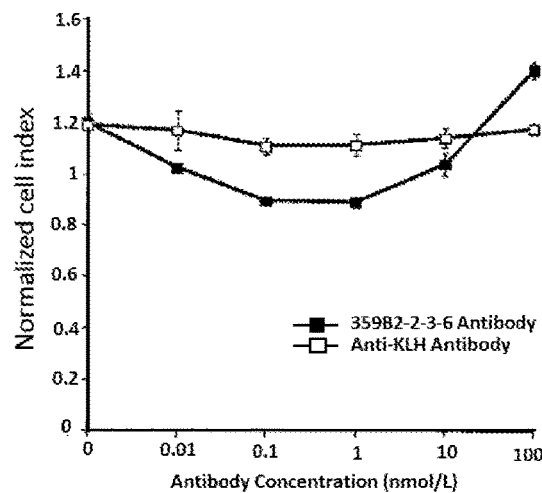
Figure 9:
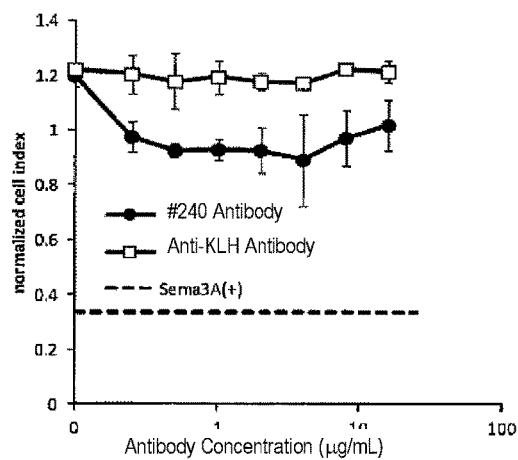
Figure 9:
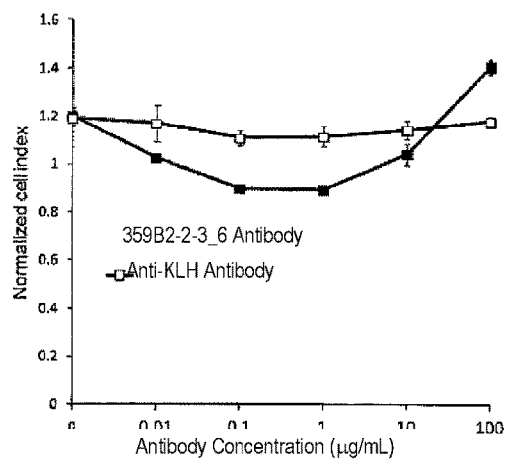

Example 19: Evaluation of Activities of Anti-Human/Mouse PlexinA1 Antibodies Activities of the prepared anti-human/mouse PlexinA1 antibodies were evaluated using the human semaphorin 3A activity measurement system with the aid of the xCELLigence system as described in Example 17. U87-MG cells were seeded at a density of $1\times10^4$ cells/well in the E-plate 96 (ACEA), which is a special plate for the xCELLigence system, and cultured at 37° C. for 12 to 24 hours. The anti-human/mouse PlexinA1 antibodies and an anti-KLH antibody of the same isotype as a control were diluted to a suitable concentration with 5% FBS-containing EMEM medium and added to each well, and then the Cell index value for each well was measured 1 hour after the addition to the well. The results are shown in FIG. 9. The anti-human/mouse PlexinA1 antibodies (hPANL #240 and 359B2-2-3-6) were confirmed to reduce the Cell index in a concentration-dependent manner, and exhibit the same activity as semaphorin 3A signaling.

Example 20: Preparation of Mouse PlexinA1 Sema Domain Recombinant Protein

A mouse PlexinA1 sema domain protein gene was designed on the basis of the sequence of NCBI Reference Sequence NP 032907.1 to encode a sequence in which the signal peptide (from the N-terminus to isoleucine at position 24) was replaced with artificial signal peptide HMM+38 (SEQ ID NO: 7), and the FLAG tag (SEQ ID NO: 5) and the termination codon were added after serine at position 512. This gene was prepared by gene synthesis. The amino acid sequence is shown in SEQ ID NO: 38. The prepared gene was incorporated into an expression vector and then introduced into FreeStyle293 cells from Invitrogen for expression, and the mouse PlexinA1 sema domain protein was purified from the culture supernatant by affinity purification using anti-FLAG M2 antibody affinity gel (Sigma-Aldrich) and gel filtration chromatography.

Example 21: Preparation of Mouse PlexinA2 Sema Domain Recombinant Protein

A mouse PlexinA2 sema domain protein gene was designed on the basis of the sequence of NCBI Reference Sequence NP 032908.2 (SEQ ID NO: 53) to encode a sequence in which the signal peptide (from the N-terminus to glycine at position 31) was replaced with artificial signal peptide HMM+38 (SEQ ID NO: 7), and the FLAG tag (SEQ ID NO: 5) and the termination codon were added after serine at position 510. This gene was prepared by gene synthesis. The amino acid sequence is shown in SEQ ID NO: 39. The prepared gene was incorporated into an expression vector and then introduced into FreeStyle293 cells from Invitrogen for expression, and the mouse PlexinA2 sema domain protein was purified from the culture supernatant by affinity purification using anti-FLAG M2 antibody affinity gel (Sigma-Aldrich) and gel filtration chromatography.

Example 22: Preparation of Mouse PlexinA1/A2 Sema Domain Chimeric Protein

A mouse PlexinA1/A2 sema domain chimeric protein gene was designed on the basis of the sequence of NCBI Reference Sequence NP_032907.1 to encode a sequence in which the signal peptide (from the N-terminus to isoleucine at position 24) was replaced with artificial signal peptide HMM+38 (SEQ ID NO: 7), and a sequence from arginine at position 459 to serine at position 510 of the mouse PlexinA2 sema domain protein, the FLAG tag (SEQ ID NO: 5), and the termination codon were added to a sequence after isoleucine at position 458 of the mouse PlexinA1 sema domain protein. This gene was prepared by gene synthesis. The amino acid sequence is shown in SEQ ID NO: 40. The prepared gene was incorporated into an expression vector and then introduced into FreeStyle293 cells from Invitrogen for expression, and the mouse PlexinA1/A2 sema domain

Figure 10A:
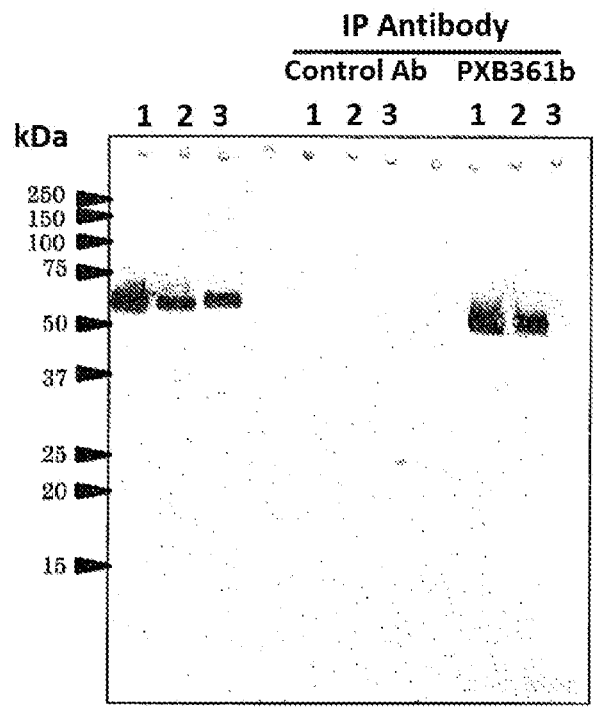
FIG. 10A illustrates a plot showing binding affinities of the antagonist antibody mouse chimera PXB361b for mouse PlexinA1, mouse PleixinA2, and the chimeric protein of mouse PlexinA1 and PlexinA2. 1: Mouse PlexinA1 sema domain, 2: mouse PlexinA1/A2 sema domain chimera, 3: mouse PlexinA2 sema domain, Control Ab: control antibody, PXB361b: mouse chimeric antibody PXB361b-mFc.
Figure 10B:
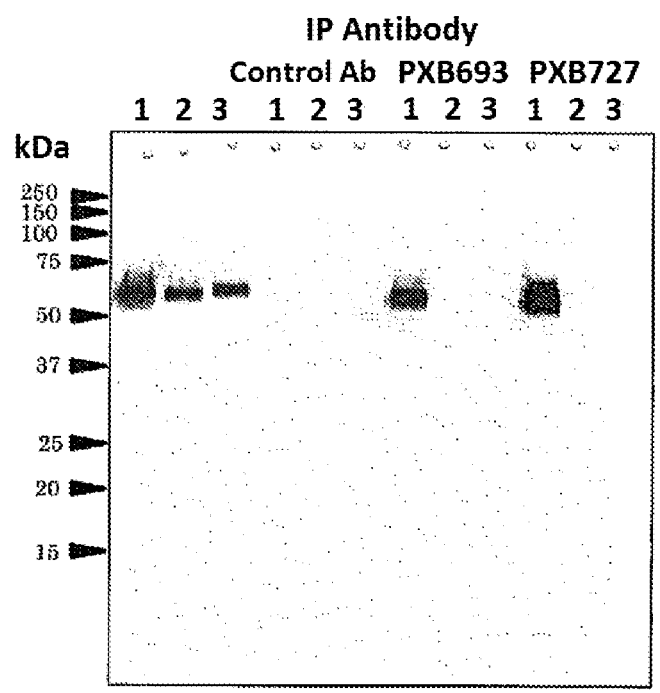
FIG. 10B illustrates a plot showing binding affinities of the agonist antibody mouse chimeras PXB693 and PXB727 for mouse PlexinA1, mouse PleixinA2, and the chimeric protein of mouse PlexinA1 and PlexinA2. 1: Mouse PlexinA1 sema domain, 2: mouse PlexinA1/A2 sema domain chimera, 3: mouse PlexinA2 sema domain, Control Ab: control antibody, PXB693: mouse chimeric antibody PXB693-mFc, PBX727-mFc: mouse chimeric antibody PXB727.

Example 23: Identification of Binding Site Regions of Anti-PlexinA1 Antibodies The mouse chimeric antibodies PXB693-mFc (mouse IgG2a), PXB727-mFc (mouse IgG2a), and PXB361b-mFc (mouse IgG1) prepared in Example 15, as well as a KLH antibody of the same isotype as each antibody were bound to Protein G-immobilized magnetic beads, and then reacted with the protein solutions prepared in Examples 20 to 22. The reacted magnetic beads were collected, and then a 4 times diluted sample buffer (containing 3-mercapto-1,2-propanediol, Wako Pure Chem) was added and the proteins were heat treated. The three types of mouse PlexinA1 sema domain proteins and the proteins released from the beads were resolved by SDS-PAGE, transferred to the PVDF membrane, and then reacted with alkaline phosphatase-labeled anti-FLAG antibody (Sigma-Aldrich) using iBind Western System (Life Technologies). Then, the proteins of interest were detected using BCIP-NBT Solution Kit (Nacalai Tesque). The Western blot results are shown in FIG. 10. The results revealed that the agonist antibodies (PXB693-mFc and PXB727-mFc) recognize the underlined region shown in FIG. 11 of the amino acid sequence of PlexinA1. This region corresponds to the underlined region of the human PlexinA1 sema domain shown in FIG. 12. The homology between the underlined human PlexinA1 sema domain and mouse PlexinA1 sema domain is considerably high; therefore, on the basis of the above-described data, the anti-human Plexin-A1 agonist antibodies of the present invention are believed to exhibit agonistic action and effects by binding to the epitope present in the underlined region of human Plexin-A1. Note that a human PlexinA1 sema domain recombinant protein, a human PlexinA2 sema domain recombinant protein, and a human PlexinA1/A2 sema domain chimeric protein can be created with reference to the description in Examples 20 to 22, and the method described in Example 23 can be used to confirm the region bound by hPANL #240 or 359B2-2-3-6.

SEQUENCE LISTING FREE TEXT

SEQ ID NO: 1: Amino acid sequence of mouse semaphorin 3A recombinant protein
SEQ ID NO: 2: Amino acid sequence of human semaphorin 3A recombinant protein
SEQ ID NO: 3: Amino acid sequence of human Plexin-A1 (NCBI Reference Sequence NP_115618.3)
SEQ ID NO: 4: Amino acid sequence of human Plexin-A1 recombinant protein
SEQ ID NO: 5: FLAG tag sequence
SEQ ID NO: 6: Amino acid sequence of the signal peptide of human Plexin-A1
SEQ ID NO: 7: Amino acid sequence of artificial signal peptide HMM+38
SEQ ID NO: 8: Amino acid sequence of EBNA1
SEQ ID NO: 9: Amino acid sequence of an H chain of human/mouse cross-reactive PlexinA1 antibody hPANL #240
SEQ ID NO: 10: Amino acid sequence of an L chain of human/mouse cross-reactive PlexinA1 antibody hPANL #240
SEQ ID NO: 11: Amino acid sequence of an H chain of human/mouse cross-reactive PlexinA1 antibody 359B2-2-3-6
SEQ ID NO: 12: Amino acid sequence of an L chain of human/mouse cross-reactive PlexinA1 antibody 359B2-2-3-6
SEQ ID NO: 13: Amino acid sequence of an H chain of mouse chimeric human/mouse cross-reactive PlexinA1 antibody hPANL #240-mFc
SEQ ID NO: 14: Amino acid sequence of an H chain of mouse chimeric human/mouse cross-reactive PlexinA1 antibody 359B2-2-3-6-mFc
SEQ ID NO: 15: Amino acid sequence of human Plexin-A1 recombinant protein
SEQ ID NO: 16: Amino acid sequence of soluble mouse PlexinA1 protein
SEQ ID NO: 17: Rabbit antibody H chain constant region sequence
SEQ ID NO: 18: Rabbit antibody L chain constant region sequence
SEQ ID NO: 19: Amino acid sequence of an H chain variable region of anti-mouse PlexinA1 antibody PXB361b
SEQ ID NO: 20: Amino acid sequence of an L chain variable region of anti-mouse PlexinA1 antibody PXB361b
SEQ ID NO: 21: Amino acid sequence of an H chain variable region of hPANL #240
SEQ ID NO: 22: Amino acid sequence of an L chain variable region of hPANL #240
SEQ ID NO: 23: Amino acid sequence of H chain CDR1 of hPANL #240
SEQ ID NO: 24: Amino acid sequence of H chain CDR2 of hPANL #240
SEQ ID NO: 25: Amino acid sequence of H chain CDR3 of hPANL #240
SEQ ID NO: 26: Amino acid sequence of L chain CDR1 of hPANL #240
SEQ ID NO: 27: Amino acid sequence of L chain CDR2 of hPANL #240
SEQ ID NO: 28: Amino acid sequence of L chain CDR3 of hPANL #240
SEQ ID NO: 29: Amino acid sequence of H chain CDR1 of 359B-2-2-3-6
SEQ ID NO: 30: Amino acid sequence of H chain CDR2 of 359B-2-2-3-6
SEQ ID NO: 31: Amino acid sequence of H chain CDR3 of 359B-2-2-3-6
SEQ ID NO: 32: Amino acid sequence of L chain CDR1 of 359B-2-2-3-6
SEQ ID NO: 33: Amino acid sequence of L chain CDR2 of 359B-2-2-3-6
SEQ ID NO: 34: Amino acid sequence of L chain CDR3 of 359B-2-2-3-6
SEQ ID NO: 35: Amino acid sequence of an H chain variable region of 359B2-2-3-6
SEQ ID NO: 36: Amino acid sequence of an L chain variable region of 359B2-2-3-6
SEQ ID NO: 37: Amino acid sequence of mouse Plexin-A1 recombinant protein
SEQ ID NO: 38: Amino acid sequence of mouse PlexinA1 sema domain recombinant protein
SEQ ID NO: 39: Amino acid sequence of mouse PlexinA2 sema domain recombinant protein
SEQ ID NO: 40: Amino acid sequence of mouse PlexinA1/A2 sema domain chimeric protein
SEQ ID NO: 41: Amino acid sequence of an H chain variable region of anti-mouse PlexinA1 antibody PXB693

SEQ ID NO: 42: Amino acid sequence of an L chain variable region of anti-mouse PlexinA1 antibody PXB693
SEQ ID NO: 43: Amino acid sequence of an H chain variable region of anti-mouse PlexinA1 antibody PXB727
SEQ ID NO: 44: Amino acid sequence of an L chain variable region of anti-mouse PlexinA1 antibody PXB727
SEQ ID NO: 45: Amino acid sequence of an H chain of mouse chimeric anti-mouse PlexinA1 antibody PXB693
SEQ ID NO: 46: Amino acid sequence of an L chain of mouse chimeric anti-mouse PlexinA1 antibody PXB693
SEQ ID NO: 47: Amino acid sequence of an H chain of mouse chimeric anti-mouse PlexinA1 antibody PXB727
SEQ ID NO: 48: Amino acid sequence of an L chain of mouse chimeric anti-mouse PlexinA1 antibody PXB727
SEQ ID NO: 49: Amino acid sequence of an H chain of mouse chimeric anti-mouse PlexinA1 antibody PXB361b
SEQ ID NO: 50: Amino acid sequence of an L chain of mouse chimeric anti-mouse PlexinA1 antibody PXB361b
SEQ ID NO: 51: Myc tag sequence
SEQ ID NO: 52: Amino acid sequence of mouse PlexinA1 (NCBI Reference Sequence NP 032907.1)
SEQ ID NO: 53: Amino acid sequence of mouse PlexinA2 (NCBI Reference Sequence NP 032908.2)

The invention claimed is:

1. An anti-Plexin-A1 agonist antibody selected from the group:
    (a) an isolated antibody that binds to Plexin-A1 comprising heavy chain variable region CDRs of SEQ ID NOS: 23, 24 and 25 and light chain variable regions CDRs of SEQ ID NOS: 26, 27 and 28,
    (b) an isolated antibody that binds to Plexin-A1 comprising heavy chain variable region CDRs of SEQ ID NOS: 29, 30 and 31 and light chain variable regions CDRs of SEQ ID NOS:32, 33 and 34,
    (c) an isolated antibody that binds to Plexin-A1 comprising heavy chain variable region CDRs comprised in SEQ ID NOS: 41 and light chain variable regions CDRs comprised in SEQ ID NOS:42, and
    (d) an isolated antibody that binds to Plexin-A1 comprising heavy chain variable region CDRs comprised in SEQ ID NOS: 43 and light chain variable regions CDRs comprised in SEQ ID NOS:44.

2. The antibody according to claim 1, which has a class 3 semaphorin-like activity.

3. The antibody according to claim 2, wherein the class 3 semaphorin-like activity is a semaphorin 3A-like activity.

4. The antibody according to claim 3, wherein the class 3 semaphorin-like activity is an activity to promote dendritic cell contraction or glioma cell contraction.

5. The antibody according to claim 4, which specifically binds to an epitope in a sema domain of Plexin-A1.

6. The antibody according to claim 5, wherein the epitope in the sema domain is an epitope in a C-terminal region of the sema domain.

7. The antibody according to claim 6, wherein the C-terminal region is for binding to residues 461 to 514 of SEQ ID NO: 3 or residues 459 to 512 of SEQ ID NO: 52.

8. The antibody according to claim 7, which cross-reacts with human Plexin-A1 and mouse Plexin-A1.

9. The antibody according to claim 8, which is a monoclonal antibody.

10. The antibody according to claim 9, which is a chimeric antibody, a humanized antibody, or a human antibody.

11. The antibody according to claim 10, which is Fab, scFv, F(ab')2, a single-chain antibody, or a bispecific antibody.

12. A pharmaceutical composition comprising the antibody according to claim 1 and a pharmaceutically acceptable carrier.

13. A method for producing a pharmaceutical composition comprising mixing the antibody according to claim 1 and a pharmaceutically acceptable carrier.

14. The pharmaceutical composition according to claim 12, which is for use in prevention and/or treatment of a disease associated with a quantitative or qualitative decrease in function of a class 3 semaphorin.

15. A kit comprising the antibody according to claim 1 and instructions for administering the antibody for preventing or treating a disease associated with a quantitative or qualitative decrease in function of a class 3 semaphorin.

16. A kit comprising the pharmaceutical composition according to claim 12 and instructions for administering the pharmaceutical composition for preventing or treating a disease associated with a quantitative or qualitative decrease in function of a class 3 semaphorin.

17. A method of treating or preventing a disease associated with a quantitative or qualitative decrease in function of a class 3 semaphorin, said method comprising administering an effective amount of the antibody according to claim 1 to a subject in in need thereof.

18. The method of claim 17, wherein the disease is an autoimmune disease, inflammatory disease or cancer.

19. The method of claim 18, wherein the autoimmune disease is a member selected from the group consisting of pruritus due to psoriasis and atopic dermatitis, allergic rhinitis, osteoporosis, rheumatoid arthritis, and systemic lupus erythematosus.

20. A method of treating or preventing a disease associated with a quantitative or qualitative decrease in function of a class 3 semaphorin, said method comprising administering an effective amount of the pharmaceutical composition according to claim 12 to a subject in need thereof.

21. The method of claim 20, wherein the disease is an autoimmune disease, inflammatory disease or cancer.

22. The method of claim 21, wherein the autoimmune disease is a member selected from the group consisting of pruritus due to psoriasis and atopic dermatitis, allergic rhinitis, osteoporosis, rheumatoid arthritis, and systemic lupus erythematosus.

* * * * *

SEQUENCE LISTING

<160> NUMBER OF SEQ ID NOS: 53

<210> SEQ ID NO 1
<211> LENGTH: 780
<212> TYPE: PRT
<213> ORGANISM: Artificial Sequence
<220> FEATURE:
<223> OTHER INFORMATION: Mouse semaphorin 3A recombinant protein

<400> SEQUENCE: 1

```
Met Trp Trp Arg Leu Trp Trp Leu Leu Leu Leu Leu Leu Leu Leu Trp
1               5                   10                  15

Pro Met Val Trp Ala Glu Asp Arg His His His His His His Asn Tyr
            20                  25                  30

Ala Asn Gly Lys Asn Asn Val Pro Arg Leu Lys Leu Ser Tyr Lys Glu
        35                  40                  45

Met Leu Glu Ser Asn Asn Val Ile Thr Phe Asn Gly Leu Ala Asn Ser
    50                  55                  60

Ser Ser Tyr His Thr Phe Leu Leu Asp Glu Glu Arg Ser Arg Leu Tyr
65                  70                  75                  80

Val Gly Ala Lys Asp His Ile Phe Ser Phe Asn Leu Val Asn Ile Lys
                85                  90                  95

Asp Phe Gln Lys Ile Val Trp Pro Val Ser Tyr Thr Arg Arg Asp Glu
            100                 105                 110

Cys Lys Trp Ala Gly Lys Asp Ile Leu Lys Glu Cys Ala Asn Phe Ile
        115                 120                 125

Lys Val Leu Glu Ala Tyr Asn Gln Thr His Leu Tyr Ala Cys Gly Thr
    130                 135                 140

Gly Ala Phe His Pro Ile Cys Thr Tyr Ile Glu Val Gly His His Pro
145                 150                 155                 160

Glu Asp Asn Ile Phe Lys Leu Gln Asp Ser His Phe Glu Asn Gly Arg
                165                 170                 175

Gly Lys Ser Pro Tyr Asp Pro Lys Leu Leu Thr Ala Ser Leu Leu Ile
            180                 185                 190

Asp Gly Glu Leu Tyr Ser Gly Thr Ala Ala Asp Phe Met Gly Arg Asp
        195                 200                 205

Phe Ala Ile Phe Arg Thr Leu Gly His His His Pro Ile Arg Thr Glu
    210                 215                 220

Gln His Asp Ser Arg Trp Leu Asn Asp Pro Arg Phe Ile Ser Ala His
225                 230                 235                 240

Leu Ile Pro Glu Ser Asp Asn Pro Glu Asp Asp Lys Val Tyr Phe Phe
                245                 250                 255

Phe Arg Glu Asn Ala Ile Asp Gly Glu His Ser Gly Lys Ala Thr His
            260                 265                 270
```

```
Ala Arg Ile Gly Gln Ile Cys Lys Asn Asp Phe Gly His Arg Ser
            275                 280                 285
Leu Val Asn Lys Trp Thr Thr Phe Leu Lys Ala Arg Leu Ile Cys Ser
        290                 295                 300
Val Pro Gly Pro Asn Gly Ile Asp Thr His Phe Asp Glu Leu Gln Asp
305                 310                 315                 320
Val Phe Leu Met Asn Ser Lys Asp Pro Lys Asn Pro Ile Val Tyr Gly
                325                 330                 335
Val Phe Thr Thr Ser Ser Asn Ile Phe Lys Gly Ser Ala Val Cys Met
                340                 345                 350
Tyr Ser Met Ser Asp Val Arg Arg Val Phe Leu Gly Pro Tyr Ala His
            355                 360                 365
Arg Asp Gly Pro Asn Tyr Gln Trp Val Pro Tyr Gln Gly Arg Val Pro
    370                 375                 380
Tyr Pro Arg Pro Gly Thr Cys Pro Ser Lys Thr Phe Gly Gly Phe Asp
385                 390                 395                 400
Ser Thr Lys Asp Leu Pro Asp Asp Val Ile Thr Phe Ala Arg Ser His
                405                 410                 415
Pro Ala Met Tyr Asn Pro Val Phe Pro Ile Asn Asn Arg Pro Ile Met
            420                 425                 430
Ile Lys Thr Asp Val Asn Tyr Gln Phe Thr Gln Ile Val Val Asp Arg
    435                 440                 445
Val Asp Ala Glu Asp Gly Gln Tyr Asp Val Met Phe Ile Gly Thr Asp
    450                 455                 460
Val Gly Thr Val Leu Lys Val Val Ser Val Pro Lys Glu Thr Trp His
465                 470                 475                 480
Asp Leu Glu Glu Val Leu Leu Glu Glu Met Thr Val Phe Arg Glu Pro
                485                 490                 495
Thr Thr Ile Ser Ala Met Glu Leu Ser Thr Lys Gln Gln Leu Tyr
            500                 505                 510
Ile Gly Ser Thr Ala Gly Val Ala Gln Leu Pro Leu His Arg Cys Asp
    515                 520                 525
Ile Tyr Gly Lys Ala Cys Ala Glu Cys Cys Leu Ala Arg Asp Pro Tyr
    530                 535                 540
Cys Ala Trp Asp Gly Ser Ser Cys Ser Arg Tyr Phe Pro Thr Ala Lys
545                 550                 555                 560
Arg Ala Thr Arg Ala Gln Asp Ile Arg Asn Gly Asp Pro Leu Thr His
                565                 570                 575
Cys Ser Asp Leu Gln His His Asp Asn His His Gly Pro Ser Leu Glu
            580                 585                 590
Glu Arg Ile Ile Tyr Gly Val Glu Asn Ser Ser Thr Phe Leu Glu Cys
        595                 600                 605
Ser Pro Lys Ser Gln Arg Ala Leu Val Tyr Trp Gln Phe Gln Arg Arg
610                 615                 620
Asn Glu Asp Arg Lys Glu Glu Ile Arg Met Gly Asp His Ile Ile Arg
625                 630                 635                 640
Thr Glu Gln Gly Leu Leu Leu Arg Ser Leu Gln Lys Lys Asp Ser Gly
                645                 650                 655
Asn Tyr Leu Cys His Ala Val Glu His Gly Phe Met Gln Thr Leu Leu
            660                 665                 670
Lys Val Thr Leu Glu Val Ile Asp Thr Glu His Leu Glu Glu Leu Leu
            675                 680                 685
His Lys Asp Asp Asp Gly Asp Gly Ser Lys Ile Lys Glu Met Ser Ser
```

-continued

```
            690             695             700
Ser Met Thr Pro Ser Gln Lys Val Trp Tyr Arg Asp Phe Met Gln Leu
705                 710                 715                 720

Ile Asn His Pro Asn Leu Asn Thr Met Asp Glu Phe Cys Glu Gln Val
                725                 730                 735

Trp Lys Arg Asp Arg Lys Gln Arg Gln Arg Pro Gly His Ser Gln
                740                 745                 750

Gly Ser Ser Asn Lys Trp Lys His Met Gln Glu Ser Lys Lys Gly Ala
                755                 760                 765

Asn Ala Ala Thr His Glu Phe Glu Arg Ala Pro Arg
770                 775                 780
```

<210> SEQ ID NO 2
<211> LENGTH: 789
<212> TYPE: PRT
<213> ORGANISM: Artificial Sequence
<220> FEATURE:
<223> OTHER INFORMATION: Human semaphorin 3A recombinant protein

<400> SEQUENCE: 2

```
Met Trp Trp Arg Leu Trp Trp Leu Leu Leu Leu Leu Leu Leu Trp
1               5                   10                  15

Pro Met Val Trp Ala Glu Asp Arg His His His His His Asn Tyr
                20                  25                  30

Gln Asn Gly Lys Asn Asn Val Pro Arg Leu Lys Leu Ser Tyr Lys Glu
                35                  40                  45

Met Leu Glu Ser Asn Asn Val Ile Thr Phe Asn Gly Leu Ala Asn Ser
50                  55                  60

Ser Ser Tyr His Thr Phe Leu Leu Asp Glu Glu Arg Ser Arg Leu Tyr
65                  70                  75                  80

Val Gly Ala Lys Asp His Ile Phe Ser Phe Asp Leu Val Asn Ile Lys
                85                  90                  95

Asp Phe Gln Lys Ile Val Trp Pro Val Ser Tyr Thr Arg Arg Asp Glu
                100                 105                 110

Cys Lys Trp Ala Gly Lys Asp Ile Leu Lys Glu Cys Ala Asn Phe Ile
                115                 120                 125

Lys Val Leu Lys Ala Tyr Asn Gln Thr His Leu Tyr Ala Cys Gly Thr
130                 135                 140

Gly Ala Phe His Pro Ile Cys Thr Tyr Ile Glu Ile Gly His His Pro
145                 150                 155                 160

Glu Asp Asn Ile Phe Lys Leu Glu Asn Ser His Phe Glu Asn Gly Arg
                165                 170                 175

Gly Lys Ser Pro Tyr Asp Pro Lys Leu Leu Thr Ala Ser Leu Leu Ile
                180                 185                 190

Asp Gly Glu Leu Tyr Ser Gly Thr Ala Ala Asp Phe Met Gly Arg Asp
                195                 200                 205

Phe Ala Ile Phe Arg Thr Leu Gly His His Pro Ile Arg Thr Glu
210                 215                 220

Gln His Asp Ser Arg Trp Leu Asn Asp Pro Lys Phe Ile Ser Ala His
225                 230                 235                 240

Leu Ile Ser Glu Ser Asp Asn Pro Glu Asp Lys Val Tyr Phe Phe
                245                 250                 255

Phe Arg Glu Asn Ala Ile Asp Gly Glu His Ser Gly Lys Ala Thr His
                260                 265                 270

Ala Arg Ile Gly Gln Ile Cys Lys Asn Asp Phe Gly Gly His Arg Ser
```

```
                275                 280                 285
Leu Val Asn Lys Trp Thr Thr Phe Leu Lys Ala Arg Leu Ile Cys Ser
290                 295                 300

Val Pro Gly Pro Asn Gly Ile Asp Thr His Phe Asp Glu Leu Gln Asp
305                 310                 315                 320

Val Phe Leu Met Asn Phe Lys Asp Pro Lys Asn Pro Val Val Tyr Gly
                325                 330                 335

Val Phe Thr Thr Ser Ser Asn Ile Phe Lys Gly Ser Ala Val Cys Met
                340                 345                 350

Tyr Ser Met Ser Asp Val Arg Arg Val Phe Leu Gly Pro Tyr Ala His
                355                 360                 365

Arg Asp Gly Pro Asn Tyr Gln Trp Val Pro Tyr Gln Gly Arg Val Pro
370                 375                 380

Tyr Pro Arg Pro Gly Thr Cys Pro Ser Lys Thr Phe Gly Gly Phe Asp
385                 390                 395                 400

Ser Thr Lys Asp Leu Pro Asp Asp Val Ile Thr Phe Ala Arg Ser His
                405                 410                 415

Pro Ala Met Tyr Asn Pro Val Phe Pro Met Asn Asn Arg Pro Ile Val
                420                 425                 430

Ile Lys Thr Asp Val Asn Tyr Gln Phe Thr Gln Ile Val Asp Arg
                435                 440                 445

Val Asp Ala Glu Asp Gly Gln Tyr Asp Val Met Phe Ile Gly Thr Asp
450                 455                 460

Val Gly Thr Val Leu Lys Val Val Ser Ile Pro Lys Glu Thr Trp Tyr
465                 470                 475                 480

Asp Leu Glu Glu Val Leu Leu Glu Glu Met Thr Val Phe Arg Glu Pro
                485                 490                 495

Thr Ala Ile Ser Ala Met Glu Leu Ser Thr Lys Gln Gln Leu Tyr
                500                 505                 510

Ile Gly Ser Thr Ala Gly Val Ala Gln Leu Pro Leu His Arg Cys Asp
                515                 520                 525

Ile Tyr Gly Lys Ala Cys Ala Glu Cys Cys Leu Ala Arg Asp Pro Tyr
                530                 535                 540

Cys Ala Trp Asp Gly Ser Ala Cys Ser Arg Tyr Phe Pro Thr Ala Lys
545                 550                 555                 560

Arg Ala Thr Arg Ala Gln Asp Ile Arg Asn Gly Asp Pro Leu Thr His
                565                 570                 575

Cys Ser Asp Leu His His Asp Asn His His Gly His Ser Pro Glu Glu
                580                 585                 590

Arg Ile Ile Tyr Gly Val Glu Asn Ser Ser Thr Phe Leu Glu Cys Ser
                595                 600                 605

Pro Lys Ser Gln Arg Ala Leu Val Tyr Trp Gln Phe Gln Arg Arg Asn
610                 615                 620

Glu Glu Arg Lys Glu Glu Ile Arg Val Asp Asp His Ile Ile Arg Thr
625                 630                 635                 640

Asp Gln Gly Leu Leu Leu Arg Ser Leu Gln Gln Lys Asp Ser Gly Asn
                645                 650                 655

Tyr Leu Cys His Ala Val Glu His Gly Phe Ile Gln Thr Leu Leu Lys
                660                 665                 670

Val Thr Leu Glu Val Ile Asp Thr Glu His Leu Glu Glu Leu Leu His
                675                 680                 685

Lys Asp Asp Gly Asp Gly Ser Lys Thr Lys Glu Met Ser Asn Ser
                690                 695                 700
```

```
Met Thr Pro Ser Gln Lys Val Trp Tyr Arg Asp Phe Met Gln Leu Ile
705                 710                 715                 720

Asn His Pro Asn Leu Asn Thr Met Asp Glu Phe Cys Glu Gln Val Trp
                725                 730                 735

Lys Arg Asp Arg Lys Gln Arg Arg Gln Arg Pro Gly His Thr Pro Gly
            740                 745                 750

Asn Ser Asn Lys Trp Lys His Leu Gln Glu Asn Lys Lys Gly Ala Asn
        755                 760                 765

Ala Ala Thr His Glu Phe Glu Arg Ala Pro Arg Ser Val Asp Tyr Lys
    770                 775                 780

Asp Asp Asp Asp Lys
785

<210> SEQ ID NO 3
<211> LENGTH: 1896
<212> TYPE: PRT
<213> ORGANISM: Homo sapiens

<400> SEQUENCE: 3

Met Pro Leu Pro Pro Arg Ser Leu Gln Val Leu Leu Leu Leu Leu Leu
1               5                   10                  15

Leu Leu Leu Leu Pro Gly Met Trp Ala Glu Ala Gly Leu Pro Arg
                20                  25                  30

Ala Gly Gly Gly Ser Gln Pro Pro Phe Arg Thr Phe Ser Ala Ser Asp
            35                  40                  45

Trp Gly Leu Thr His Leu Val Val His Glu Gln Thr Gly Glu Val Tyr
        50                  55                  60

Val Gly Ala Val Asn Arg Ile Tyr Lys Leu Ser Gly Asn Leu Thr Leu
65                  70                  75                  80

Leu Arg Ala His Val Thr Gly Pro Val Glu Asp Asn Glu Lys Cys Tyr
                85                  90                  95

Pro Pro Pro Ser Val Gln Ser Cys Pro His Gly Leu Gly Ser Thr Asp
            100                 105                 110

Asn Val Asn Lys Leu Leu Leu Leu Asp Tyr Ala Ala Asn Arg Leu Leu
        115                 120                 125

Ala Cys Gly Ser Ala Ser Gln Gly Ile Cys Gln Phe Leu Arg Leu Asp
    130                 135                 140

Asp Leu Phe Lys Leu Gly Glu Pro His His Arg Lys Glu His Tyr Leu
145                 150                 155                 160

Ser Ser Val Gln Glu Ala Gly Ser Met Ala Gly Val Leu Ile Ala Gly
                165                 170                 175

Pro Pro Gly Gln Gly Gln Ala Lys Leu Phe Val Gly Thr Pro Ile Asp
            180                 185                 190

Gly Lys Ser Glu Tyr Phe Pro Thr Leu Ser Ser Arg Arg Leu Met Ala
        195                 200                 205

Asn Glu Glu Asp Ala Asp Met Phe Gly Phe Val Tyr Gln Asp Glu Phe
    210                 215                 220

Val Ser Ser Gln Leu Lys Ile Pro Ser Asp Thr Leu Ser Lys Phe Pro
225                 230                 235                 240

Ala Phe Asp Ile Tyr Tyr Val Tyr Ser Phe Arg Ser Glu Gln Phe Val
                245                 250                 255

Tyr Tyr Leu Thr Leu Gln Leu Asp Thr Gln Leu Thr Ser Pro Asp Ala
            260                 265                 270

Ala Gly Glu His Phe Phe Thr Ser Lys Ile Val Arg Leu Cys Val Asp
```

```
               275                 280                 285
Asp Pro Lys Phe Tyr Ser Tyr Val Glu Phe Pro Ile Gly Cys Glu Gln
290                 295                 300

Ala Gly Val Glu Tyr Arg Leu Val Gln Asp Ala Tyr Leu Ser Arg Pro
305                 310                 315                 320

Gly Arg Ala Leu Ala His Gln Leu Gly Leu Ala Glu Asp Glu Asp Val
                    325                 330                 335

Leu Phe Thr Val Phe Ala Gln Gly Gln Lys Asn Arg Val Lys Pro Pro
                340                 345                 350

Lys Glu Ser Ala Leu Cys Leu Phe Thr Leu Arg Ala Ile Lys Glu Lys
            355                 360                 365

Ile Lys Glu Arg Ile Gln Ser Cys Tyr Arg Gly Gly Lys Leu Ser
370                 375                 380

Leu Pro Trp Leu Leu Asn Lys Glu Leu Gly Cys Ile Asn Ser Pro Leu
385                 390                 395                 400

Gln Ile Asp Asp Phe Cys Gly Gln Asp Phe Asn Gln Pro Leu Gly
                405                 410                 415

Gly Thr Val Thr Ile Glu Gly Thr Pro Leu Phe Val Asp Lys Asp Asp
                420                 425                 430

Gly Leu Thr Ala Val Ala Ala Tyr Asp Tyr Arg Gly Arg Thr Val Val
                435                 440                 445

Phe Ala Gly Thr Arg Ser Gly Arg Ile Arg Lys Ile Leu Val Asp Leu
450                 455                 460

Ser Asn Pro Gly Gly Arg Pro Ala Leu Ala Tyr Glu Ser Val Val Ala
465                 470                 475                 480

Gln Glu Gly Ser Pro Ile Leu Arg Asp Leu Val Leu Ser Pro Asn His
                485                 490                 495

Gln Tyr Leu Tyr Ala Met Thr Glu Lys Gln Val Thr Arg Val Pro Val
                500                 505                 510

Glu Ser Cys Val Gln Tyr Thr Ser Cys Glu Leu Cys Leu Gly Ser Arg
                515                 520                 525

Asp Pro His Cys Gly Trp Cys Val Leu His Ser Ile Cys Ser Arg Arg
                530                 535                 540

Asp Ala Cys Glu Arg Ala Asp Glu Pro Gln Arg Phe Ala Ala Asp Leu
545                 550                 555                 560

Leu Gln Cys Val Gln Leu Thr Val Gln Pro Arg Asn Val Ser Val Thr
                565                 570                 575

Met Ser Gln Val Pro Leu Val Leu Gln Ala Trp Asn Val Pro Asp Leu
                580                 585                 590

Ser Ala Gly Val Asn Cys Ser Phe Glu Asp Phe Thr Glu Ser Glu Ser
                595                 600                 605

Val Leu Glu Asp Gly Arg Ile His Cys Arg Ser Pro Ser Ala Arg Glu
610                 615                 620

Val Ala Pro Ile Thr Arg Gly Gln Gly Asp Gln Arg Val Val Lys Leu
625                 630                 635                 640

Tyr Leu Lys Ser Lys Glu Thr Gly Lys Lys Phe Ala Ser Val Asp Phe
                645                 650                 655

Val Phe Tyr Asn Cys Ser Val His Gln Ser Cys Leu Ser Cys Val Asn
                660                 665                 670

Gly Ser Phe Pro Cys His Trp Cys Lys Tyr Arg His Val Cys Thr His
                675                 680                 685

Asn Val Ala Asp Cys Ala Phe Leu Glu Gly Arg Val Asn Val Ser Glu
690                 695                 700
```

```
Asp Cys Pro Gln Ile Leu Pro Ser Thr Gln Ile Tyr Val Pro Val Gly
705                 710                 715                 720

Val Val Lys Pro Ile Thr Leu Ala Ala Arg Asn Leu Pro Gln Pro Gln
            725                 730                 735

Ser Gly Gln Arg Gly Tyr Glu Cys Leu Phe His Ile Pro Gly Ser Pro
        740                 745                 750

Ala Arg Val Thr Ala Leu Arg Phe Asn Ser Ser Leu Gln Cys Gln
            755                 760                 765

Asn Ser Ser Tyr Ser Tyr Glu Gly Asn Asp Val Ser Asp Leu Pro Val
770                 775                 780

Asn Leu Ser Val Val Trp Asn Gly Asn Phe Val Ile Asp Asn Pro Gln
785                 790                 795                 800

Asn Ile Gln Ala His Leu Tyr Lys Cys Pro Ala Leu Arg Glu Ser Cys
                805                 810                 815

Gly Leu Cys Leu Lys Ala Asp Pro Arg Phe Glu Cys Gly Trp Cys Val
            820                 825                 830

Ala Glu Arg Arg Cys Ser Leu Arg His His Cys Ala Ala Asp Thr Pro
        835                 840                 845

Ala Ser Trp Met His Ala Arg His Gly Ser Ser Arg Cys Thr Asp Pro
850                 855                 860

Lys Ile Leu Lys Leu Ser Pro Glu Thr Gly Pro Arg Gln Gly Gly Thr
865                 870                 875                 880

Arg Leu Thr Ile Thr Gly Glu Asn Leu Gly Leu Arg Phe Glu Asp Val
                885                 890                 895

Arg Leu Gly Val Arg Val Gly Lys Val Leu Cys Ser Pro Val Glu Ser
            900                 905                 910

Glu Tyr Ile Ser Ala Glu Gln Ile Val Cys Glu Ile Gly Asp Ala Ser
        915                 920                 925

Ser Val Arg Ala His Asp Ala Leu Val Glu Val Cys Val Arg Asp Cys
930                 935                 940

Ser Pro His Tyr Arg Ala Leu Ser Pro Lys Arg Phe Thr Phe Val Thr
945                 950                 955                 960

Pro Thr Phe Tyr Arg Val Ser Pro Ser Arg Gly Pro Leu Ser Gly Gly
                965                 970                 975

Thr Trp Ile Gly Ile Glu Gly Ser His Leu Asn Ala Gly Ser Asp Val
            980                 985                 990

Ala Val Ser Val Gly Gly Arg Pro Cys Ser Phe Ser Trp Arg Asn Ser
        995                 1000                1005

Arg Glu Ile Arg Cys Leu Thr Pro Pro Gly Gln Ser Pro Gly Ser
    1010            1015                1020

Ala Pro Ile Ile Ile Asn Ile Asn Arg Ala Gln Leu Thr Asn Pro
    1025            1030                1035

Glu Val Lys Tyr Asn Tyr Thr Glu Asp Pro Thr Ile Leu Arg Ile
    1040            1045                1050

Asp Pro Glu Trp Ser Ile Asn Ser Gly Gly Thr Leu Leu Thr Val
    1055            1060                1065

Thr Gly Thr Asn Leu Ala Thr Val Arg Glu Pro Arg Ile Arg Ala
    1070            1075                1080

Lys Tyr Gly Gly Ile Glu Arg Glu Asn Gly Cys Leu Val Tyr Asn
    1085            1090                1095

Asp Thr Thr Met Val Cys Arg Ala Pro Ser Val Ala Asn Pro Val
    1100            1105                1110
```

```
Arg Ser Pro Pro Glu Leu Gly Glu Arg Pro Asp Glu Leu Gly Phe
    1115            1120                1125

Val Met Asp Asn Val Arg Ser Leu Leu Val Leu Asn Ser Thr Ser
    1130            1135                1140

Phe Leu Tyr Tyr Pro Asp Pro Val Leu Glu Pro Leu Ser Pro Thr
    1145            1150                1155

Gly Leu Leu Glu Leu Lys Pro Ser Ser Pro Leu Ile Leu Lys Gly
    1160            1165                1170

Arg Asn Leu Leu Pro Pro Ala Pro Gly Asn Ser Arg Leu Asn Tyr
    1175            1180                1185

Thr Val Leu Ile Gly Ser Thr Pro Cys Thr Leu Thr Val Ser Glu
    1190            1195                1200

Thr Gln Leu Leu Cys Glu Ala Pro Asn Leu Thr Gly Gln His Lys
    1205            1210                1215

Val Thr Val Arg Ala Gly Gly Phe Glu Phe Ser Pro Gly Thr Leu
    1220            1225                1230

Gln Val Tyr Ser Asp Ser Leu Leu Thr Leu Pro Ala Ile Val Gly
    1235            1240                1245

Ile Gly Gly Gly Gly Gly Leu Leu Leu Leu Val Ile Val Ala Val
    1250            1255                1260

Leu Ile Ala Tyr Lys Arg Lys Ser Arg Asp Ala Asp Arg Thr Leu
    1265            1270                1275

Lys Arg Leu Gln Leu Gln Met Asp Asn Leu Glu Ser Arg Val Ala
    1280            1285                1290

Leu Glu Cys Lys Glu Ala Phe Ala Glu Leu Gln Thr Asp Ile His
    1295            1300                1305

Glu Leu Thr Asn Asp Leu Asp Gly Ala Gly Ile Pro Phe Leu Asp
    1310            1315                1320

Tyr Arg Thr Tyr Ala Met Arg Val Leu Phe Pro Gly Ile Glu Asp
    1325            1330                1335

His Pro Val Leu Lys Glu Met Glu Val Gln Ala Asn Val Glu Lys
    1340            1345                1350

Ser Leu Thr Leu Phe Gly Gln Leu Leu Thr Lys Lys His Phe Leu
    1355            1360                1365

Leu Thr Phe Ile Arg Thr Leu Glu Ala Gln Arg Ser Phe Ser Met
    1370            1375                1380

Arg Asp Arg Gly Asn Val Ala Ser Leu Ile Met Thr Ala Leu Gln
    1385            1390                1395

Gly Glu Met Glu Tyr Ala Thr Gly Val Leu Lys Gln Leu Leu Ser
    1400            1405                1410

Asp Leu Ile Glu Lys Asn Leu Glu Ser Lys Asn His Pro Lys Leu
    1415            1420                1425

Leu Leu Arg Arg Thr Glu Ser Val Ala Glu Lys Met Leu Thr Asn
    1430            1435                1440

Trp Phe Thr Phe Leu Leu Tyr Lys Phe Leu Lys Glu Cys Ala Gly
    1445            1450                1455

Glu Pro Leu Phe Met Leu Tyr Cys Ala Ile Lys Gln Gln Met Glu
    1460            1465                1470

Lys Gly Pro Ile Asp Ala Ile Thr Gly Glu Ala Arg Tyr Ser Leu
    1475            1480                1485

Ser Glu Asp Lys Leu Ile Arg Gln Gln Ile Asp Tyr Lys Thr Leu
    1490            1495                1500

Thr Leu Asn Cys Val Asn Pro Glu Asn Glu Asn Ala Pro Glu Val
```

-continued

```
            1505                1510                1515

Pro Val Lys Gly Leu Asp Cys Asp Thr Val Thr Gln Ala Lys Glu
        1520                1525                1530

Lys Leu Leu Asp Ala Ala Tyr Lys Gly Val Pro Tyr Ser Gln Arg
        1535                1540                1545

Pro Lys Ala Ala Asp Met Asp Leu Glu Trp Arg Gln Gly Arg Met
        1550                1555                1560

Ala Arg Ile Ile Leu Gln Asp Glu Asp Val Thr Thr Lys Ile Asp
        1565                1570                1575

Asn Asp Trp Lys Arg Leu Asn Thr Leu Ala His Tyr Gln Val Thr
        1580                1585                1590

Asp Gly Ser Ser Val Ala Leu Val Pro Lys Gln Thr Ser Ala Tyr
        1595                1600                1605

Asn Ile Ser Asn Ser Ser Thr Phe Thr Lys Ser Leu Ser Arg Tyr
        1610                1615                1620

Glu Ser Met Leu Arg Thr Ala Ser Ser Pro Asp Ser Leu Arg Ser
        1625                1630                1635

Arg Thr Pro Met Ile Thr Pro Asp Leu Glu Ser Gly Thr Lys Leu
        1640                1645                1650

Trp His Leu Val Lys Asn His Asp His Leu Asp Gln Arg Glu Gly
        1655                1660                1665

Asp Arg Gly Ser Lys Met Val Ser Glu Ile Tyr Leu Thr Arg Leu
        1670                1675                1680

Leu Ala Thr Lys Gly Thr Leu Gln Lys Phe Val Asp Asp Leu Phe
        1685                1690                1695

Glu Thr Ile Phe Ser Thr Ala His Arg Gly Ser Ala Leu Pro Leu
        1700                1705                1710

Ala Ile Lys Tyr Met Phe Asp Phe Leu Asp Glu Gln Ala Asp Lys
        1715                1720                1725

His Gln Ile His Asp Ala Asp Val Arg His Thr Trp Lys Ser Asn
        1730                1735                1740

Cys Leu Pro Leu Arg Phe Trp Val Asn Val Ile Lys Asn Pro Gln
        1745                1750                1755

Phe Val Phe Asp Ile His Lys Asn Ser Ile Thr Asp Ala Cys Leu
        1760                1765                1770

Ser Val Val Ala Gln Thr Phe Met Asp Ser Cys Ser Thr Ser Glu
        1775                1780                1785

His Lys Leu Gly Lys Asp Ser Pro Ser Asn Lys Leu Leu Tyr Ala
        1790                1795                1800

Lys Asp Ile Pro Asn Tyr Lys Ser Trp Val Glu Arg Tyr Tyr Ala
        1805                1810                1815

Asp Ile Ala Lys Met Pro Ala Ile Ser Asp Gln Asp Met Ser Ala
        1820                1825                1830

Tyr Leu Ala Glu Gln Ser Arg Leu His Leu Ser Gln Phe Asn Ser
        1835                1840                1845

Met Ser Ala Leu His Glu Ile Tyr Ser Tyr Ile Thr Lys Tyr Lys
        1850                1855                1860

Asp Glu Ile Leu Ala Ala Leu Glu Lys Asp Glu Gln Ala Arg Arg
        1865                1870                1875

Gln Arg Leu Arg Ser Lys Leu Glu Gln Val Val Asp Thr Met Ala
        1880                1885                1890

Leu Ser Ser
        1895
```

<210> SEQ ID NO 4
<211> LENGTH: 1247
<212> TYPE: PRT
<213> ORGANISM: Artificial Sequence
<220> FEATURE:
<223> OTHER INFORMATION: Human plexin A1 recombinant protein

<400> SEQUENCE: 4

```
Met Trp Trp Arg Leu Trp Trp Leu Leu Leu Leu Leu Leu Leu Leu Trp
1               5                   10                  15

Pro Met Val Trp Ala Glu Ala Gly Leu Pro Arg Ala Gly Gly Gly Ser
            20                  25                  30

Gln Pro Pro Phe Arg Thr Phe Ser Ala Ser Asp Trp Gly Leu Thr His
        35                  40                  45

Leu Val Val His Glu Gln Thr Gly Glu Val Tyr Val Gly Ala Val Asn
    50                  55                  60

Arg Ile Tyr Lys Leu Ser Gly Asn Leu Thr Leu Leu Arg Ala His Val
65                  70                  75                  80

Thr Gly Pro Val Glu Asp Asn Glu Lys Cys Tyr Pro Pro Ser Val
                85                  90                  95

Gln Ser Cys Pro His Gly Leu Gly Ser Thr Asp Asn Val Asn Lys Leu
            100                 105                 110

Leu Leu Leu Asp Tyr Ala Ala Asn Arg Leu Leu Ala Cys Gly Ser Ala
        115                 120                 125

Ser Gln Gly Ile Cys Gln Phe Leu Arg Leu Asp Asp Leu Phe Lys Leu
    130                 135                 140

Gly Glu Pro His His Arg Lys Glu His Tyr Leu Ser Ser Val Gln Glu
145                 150                 155                 160

Ala Gly Ser Met Ala Gly Val Leu Ile Ala Gly Pro Pro Gly Gln Gly
                165                 170                 175

Gln Ala Lys Leu Phe Val Gly Thr Pro Ile Asp Gly Lys Ser Glu Tyr
            180                 185                 190

Phe Pro Thr Leu Ser Ser Arg Arg Leu Met Ala Asn Glu Glu Asp Ala
        195                 200                 205

Asp Met Phe Gly Phe Val Tyr Gln Asp Glu Phe Val Ser Ser Gln Leu
    210                 215                 220

Lys Ile Pro Ser Asp Thr Leu Ser Lys Phe Pro Ala Phe Asp Ile Tyr
225                 230                 235                 240

Tyr Val Tyr Ser Phe Arg Ser Glu Gln Phe Val Tyr Tyr Leu Thr Leu
                245                 250                 255

Gln Leu Asp Thr Gln Leu Thr Ser Pro Asp Ala Ala Gly Glu His Phe
            260                 265                 270

Phe Thr Ser Lys Ile Val Arg Leu Cys Val Asp Asp Pro Lys Phe Tyr
        275                 280                 285

Ser Tyr Val Glu Phe Pro Ile Gly Cys Glu Gln Ala Gly Val Glu Tyr
    290                 295                 300

Arg Leu Val Gln Asp Ala Tyr Leu Ser Arg Pro Gly Arg Ala Leu Ala
305                 310                 315                 320

His Gln Leu Gly Leu Ala Glu Asp Glu Asp Val Leu Phe Thr Val Phe
                325                 330                 335

Ala Gln Gly Gln Lys Asn Arg Val Lys Pro Pro Lys Glu Ser Ala Leu
            340                 345                 350

Cys Leu Phe Thr Leu Arg Ala Ile Lys Glu Lys Ile Lys Glu Arg Ile
        355                 360                 365
```

```
Gln Ser Cys Tyr Arg Gly Glu Gly Lys Leu Ser Leu Pro Trp Leu Leu
    370                 375                 380

Asn Lys Glu Leu Gly Cys Ile Asn Ser Pro Leu Gln Ile Asp Asp Asp
385                 390                 395                 400

Phe Cys Gly Gln Asp Phe Asn Gln Pro Leu Gly Gly Thr Val Thr Ile
                405                 410                 415

Glu Gly Thr Pro Leu Phe Val Asp Lys Asp Gly Leu Thr Ala Val
            420                 425                 430

Ala Ala Tyr Asp Tyr Arg Gly Arg Thr Val Val Phe Ala Gly Thr Arg
            435                 440                 445

Ser Gly Arg Ile Arg Lys Ile Leu Val Asp Leu Ser Asn Pro Gly Gly
    450                 455                 460

Arg Pro Ala Leu Ala Tyr Glu Ser Val Val Ala Gln Glu Gly Ser Pro
465                 470                 475                 480

Ile Leu Arg Asp Leu Val Leu Ser Pro Asn His Gln Tyr Leu Tyr Ala
                485                 490                 495

Met Thr Glu Lys Gln Val Thr Arg Val Pro Val Glu Ser Cys Val Gln
                500                 505                 510

Tyr Thr Ser Cys Glu Leu Cys Leu Gly Ser Arg Asp Pro His Cys Gly
                515                 520                 525

Trp Cys Val Leu His Ser Ile Cys Ser Arg Arg Asp Ala Cys Glu Arg
    530                 535                 540

Ala Asp Glu Pro Gln Arg Phe Ala Ala Asp Leu Leu Gln Cys Val Gln
545                 550                 555                 560

Leu Thr Val Gln Pro Arg Asn Val Ser Val Thr Met Ser Gln Val Pro
                565                 570                 575

Leu Val Leu Gln Ala Trp Asn Val Pro Asp Leu Ser Ala Gly Val Asn
                580                 585                 590

Cys Ser Phe Glu Asp Phe Thr Glu Ser Glu Ser Val Leu Glu Asp Gly
                595                 600                 605

Arg Ile His Cys Arg Ser Pro Ser Ala Arg Glu Val Ala Pro Ile Thr
    610                 615                 620

Arg Gly Gln Gly Asp Gln Arg Val Val Lys Leu Tyr Leu Lys Ser Lys
625                 630                 635                 640

Glu Thr Gly Lys Lys Phe Ala Ser Val Asp Phe Val Phe Tyr Asn Cys
                645                 650                 655

Ser Val His Gln Ser Cys Leu Ser Cys Val Asn Gly Ser Phe Pro Cys
                660                 665                 670

His Trp Cys Lys Tyr Arg His Val Cys Thr His Asn Val Ala Asp Cys
    675                 680                 685

Ala Phe Leu Glu Gly Arg Val Asn Val Ser Glu Asp Cys Pro Gln Ile
    690                 695                 700

Leu Pro Ser Thr Gln Ile Tyr Val Pro Val Gly Val Val Lys Pro Ile
705                 710                 715                 720

Thr Leu Ala Ala Arg Asn Leu Pro Gln Pro Gln Ser Gly Gln Arg Gly
                725                 730                 735

Tyr Glu Cys Leu Phe His Ile Pro Gly Ser Pro Ala Arg Val Thr Ala
                740                 745                 750

Leu Arg Phe Asn Ser Ser Ser Leu Gln Cys Gln Asn Ser Ser Tyr Ser
            755                 760                 765

Tyr Glu Gly Asn Asp Val Ser Asp Leu Pro Val Asn Leu Ser Val Val
    770                 775                 780
```

```
Trp Asn Gly Asn Phe Val Ile Asp Asn Pro Gln Asn Ile Gln Ala His
785                 790                 795                 800

Leu Tyr Lys Cys Pro Ala Leu Arg Glu Ser Cys Gly Leu Cys Leu Lys
            805                 810                 815

Ala Asp Pro Arg Phe Glu Cys Gly Trp Cys Val Ala Glu Arg Cys
            820                 825                 830

Ser Leu Arg His His Cys Ala Ala Asp Thr Pro Ala Ser Trp Met His
            835                 840                 845

Ala Arg His Gly Ser Ser Arg Cys Thr Asp Pro Lys Ile Leu Lys Leu
            850                 855                 860

Ser Pro Glu Thr Gly Pro Arg Gln Gly Gly Thr Arg Leu Thr Ile Thr
865                 870                 875                 880

Gly Glu Asn Leu Gly Leu Arg Phe Glu Asp Val Arg Leu Gly Val Arg
                885                 890                 895

Val Gly Lys Val Leu Cys Ser Pro Val Glu Ser Glu Tyr Ile Ser Ala
                900                 905                 910

Glu Gln Ile Val Cys Glu Ile Gly Asp Ala Ser Ser Val Arg Ala His
                915                 920                 925

Asp Ala Leu Val Glu Val Cys Val Arg Asp Cys Ser Pro His Tyr Arg
                930                 935                 940

Ala Leu Ser Pro Lys Arg Phe Thr Phe Val Thr Pro Thr Phe Tyr Arg
945                 950                 955                 960

Val Ser Pro Ser Arg Gly Pro Leu Ser Gly Thr Trp Ile Gly Ile
                965                 970                 975

Glu Gly Ser His Leu Asn Ala Gly Ser Asp Val Ala Val Ser Val Gly
                980                 985                 990

Gly Arg Pro Cys Ser Phe Ser Trp Arg Asn Ser Arg Glu Ile Arg Cys
                995                 1000                1005

Leu Thr Pro Pro Gly Gln Ser Pro Gly Ser Ala Pro Ile Ile Ile
    1010                1015                1020

Asn Ile Asn Arg Ala Gln Leu Thr Asn Pro Glu Val Lys Tyr Asn
    1025                1030                1035

Tyr Thr Glu Asp Pro Thr Ile Leu Arg Ile Asp Pro Glu Trp Ser
    1040                1045                1050

Ile Asn Ser Gly Gly Thr Leu Leu Thr Val Thr Gly Thr Asn Leu
    1055                1060                1065

Ala Thr Val Arg Glu Pro Arg Ile Arg Ala Lys Tyr Gly Gly Ile
    1070                1075                1080

Glu Arg Glu Asn Gly Cys Leu Val Tyr Asn Asp Thr Thr Met Val
    1085                1090                1095

Cys Arg Ala Pro Ser Val Ala Asn Pro Val Arg Ser Pro Pro Glu
    1100                1105                1110

Leu Gly Glu Arg Pro Asp Glu Leu Gly Phe Val Met Asp Asn Val
    1115                1120                1125

Arg Ser Leu Leu Val Leu Asn Ser Thr Ser Phe Leu Tyr Tyr Pro
    1130                1135                1140

Asp Pro Val Leu Glu Pro Leu Ser Pro Thr Gly Leu Leu Glu Leu
    1145                1150                1155

Lys Pro Ser Ser Pro Leu Ile Leu Lys Gly Arg Asn Leu Leu Pro
    1160                1165                1170

Pro Ala Pro Gly Asn Ser Arg Leu Asn Tyr Thr Val Leu Ile Gly
    1175                1180                1185

Ser Thr Pro Cys Thr Leu Thr Val Ser Glu Thr Gln Leu Leu Cys
```

```
              1190          1195          1200
Glu Ala  Pro Asn Leu Thr Gly  Gln His Lys Val  Thr Val Arg Ala
     1205          1210          1215

Gly Gly Phe Glu Phe Ser Pro  Gly Thr Leu Gln Val  Tyr Ser Asp
     1220          1225          1230

Ser Leu  Leu Thr Leu Pro Asp  Tyr Lys Asp Asp  Asp Lys
     1235          1240          1245

<210> SEQ ID NO 5
<211> LENGTH: 8
<212> TYPE: PRT
<213> ORGANISM: Artificial Sequence
<220> FEATURE:
<223> OTHER INFORMATION: FLAG tag sequence

<400> SEQUENCE: 5

Asp Tyr Lys Asp Asp Asp Asp Lys
1               5

<210> SEQ ID NO 6
<211> LENGTH: 26
<212> TYPE: PRT
<213> ORGANISM: Homo sapiens

<400> SEQUENCE: 6

Met Pro Leu Pro Pro Arg Ser Leu Gln Val Leu Leu Leu Leu Leu
1               5                   10                  15

Leu Leu Leu Leu Leu Pro Gly Met Trp Ala
            20                  25

<210> SEQ ID NO 7
<211> LENGTH: 21
<212> TYPE: PRT
<213> ORGANISM: Artificial Sequence
<220> FEATURE:
<223> OTHER INFORMATION: Artificial signal peptide HMM+38

<400> SEQUENCE: 7

Met Trp Trp Arg Leu Trp Trp Leu Leu Leu Leu Leu Leu Leu Trp
1               5                   10                  15

Pro Met Val Trp Ala
            20

<210> SEQ ID NO 8
<211> LENGTH: 641
<212> TYPE: PRT
<213> ORGANISM: Homo sapiens

<400> SEQUENCE: 8

Met Ser Asp Glu Gly Pro Gly Thr Gly Pro Gly Asn Gly Leu Gly Glu
1               5                   10                  15

Lys Gly Asp Thr Ser Gly Pro Glu Gly Ser Gly Gly Ser Gly Pro Gln
            20                  25                  30

Arg Arg Gly Gly Asp Asn His Gly Arg Gly Arg Gly Arg Gly Arg Gly
        35                  40                  45

Arg Gly Gly Gly Arg Pro Gly Ala Pro Gly Gly Ser Gly Ser Gly Pro
    50                  55                  60

Arg His Arg Asp Gly Val Arg Arg Pro Gln Lys Arg Pro Ser Cys Ile
65                  70                  75                  80

Gly Cys Lys Gly Thr His Gly Gly Thr Gly Ala Gly Ala Gly Ala Gly
                85                  90                  95
```

Gly Ala Gly Ala Gly Ala Gly Ala Gly Gly Ala Gly Ala Gly
            100                 105                 110
Gly Gly Ala Gly Gly Ala Gly Ala Gly Gly Ala Gly Ala Gly Gly
            115                 120                 125
Gly Ala Gly Ala Gly Gly Ala Gly Gly Ala Gly Gly Ala Gly Ala
            130                 135                 140
Gly Gly Gly Ala Gly Ala Gly Gly Ala Gly Ala Gly Ala Gly
145                 150                 155                 160
Gly Gly Ala Gly Gly Ala Gly Ala Gly Ala Gly Gly Ala Gly
            165                 170                 175
Ala Gly Gly Gly Ala Gly Gly Ala Gly Ala Gly Gly Ala Gly Gly
            180                 185                 190
Ala Gly Gly Ala Gly Ala Gly Gly Ala Gly Ala Gly Gly Ala Gly
            195                 200                 205
Gly Ala Gly Gly Ala Gly Ala Gly Gly Ala Gly Ala Gly Gly Ala
            210                 215                 220
Gly Gly Ala Gly Gly Ala Gly Gly Ala Gly Ala Gly Gly Gly Ala
225                 230                 235                 240
Gly Ala Gly Gly Ala Gly Ala Gly Gly Ala Gly Gly Ala Gly Ala
            245                 250                 255
Gly Ala Gly Gly Ala Gly Ala Gly Gly Ala Gly Ala Gly Ala Gly
            260                 265                 270
Gly Gly Ala Gly Gly Ala Gly Ala Gly Gly Ala Gly Gly Ala Gly
            275                 280                 285
Ala Gly Gly Ala Gly Gly Ala Gly Ala Gly Gly Ala Gly Ala Gly
            290                 295                 300
Ala Gly Gly Ala Gly Gly Ala Gly Ala Gly Gly Ala Gly Ala Gly
305                 310                 315                 320
Gly Ala Gly Ala Gly Gly Gly Gly Arg Gly Arg Gly Gly Ser Gly Gly
            325                 330                 335
Arg Gly Arg Gly Gly Ser Gly Gly Arg Gly Arg Gly Gly Ser Gly Gly
            340                 345                 350
Arg Arg Gly Arg Gly Arg Glu Arg Ala Arg Gly Gly Ser Arg Glu Arg
            355                 360                 365
Ala Arg Gly Arg Gly Arg Gly Arg Gly Glu Lys Arg Pro Arg Ser Pro
            370                 375                 380
Ser Ser Gln Ser Ser Ser Gly Ser Pro Pro Arg Arg Pro Pro Pro
385                 390                 395                 400
Gly Arg Arg Pro Phe Phe His Pro Val Gly Glu Ala Asp Tyr Phe Glu
            405                 410                 415
Tyr His Gln Glu Gly Gly Pro Asp Gly Glu Pro Asp Val Pro Pro Gly
            420                 425                 430
Ala Ile Glu Gln Gly Pro Ala Asp Asp Pro Gly Glu Gly Pro Ser Thr
            435                 440                 445
Gly Pro Arg Gly Gln Gly Asp Gly Gly Arg Arg Lys Lys Gly Gly Trp
            450                 455                 460
Phe Gly Lys His Arg Gly Gln Gly Gly Ser Asn Pro Lys Phe Glu Asn
465                 470                 475                 480
Ile Ala Glu Gly Leu Arg Ala Leu Leu Ala Arg Ser His Val Glu Arg
            485                 490                 495
Thr Thr Asp Glu Gly Thr Trp Val Ala Gly Val Phe Val Tyr Gly Gly
            500                 505                 510

Ser Lys Thr Ser Leu Tyr Asn Leu Arg Arg Gly Thr Ala Leu Ala Ile
515 520 525

Pro Gln Cys Arg Leu Thr Pro Leu Ser Arg Leu Pro Phe Gly Met Ala
530 535 540

Pro Gly Pro Gly Pro Gln Pro Gly Pro Leu Arg Glu Ser Ile Val Cys
545 550 555 560

Tyr Phe Met Val Phe Leu Gln Thr His Ile Phe Ala Glu Val Leu Lys
565 570 575

Asp Ala Ile Lys Asp Leu Val Met Thr Lys Pro Ala Pro Thr Cys Asn
580 585 590

Ile Arg Val Thr Val Cys Ser Phe Asp Asp Gly Val Asp Leu Pro Pro
595 600 605

Trp Phe Pro Pro Met Val Glu Gly Ala Ala Ala Glu Gly Asp Asp Gly
610 615 620

Asp Asp Gly Asp Glu Gly Gly Asp Gly Asp Glu Gly Glu Glu Gly Gln
625 630 635 640

Glu

<210> SEQ ID NO 9
<211> LENGTH: 450
<212> TYPE: PRT
<213> ORGANISM: Homo sapiens

<400> SEQUENCE: 9

Gln Val Gln Leu Gln Gln Ser Gly Pro Gly Leu Val Lys Pro Ser Gln
1 5 10 15

Thr Leu Ser Leu Thr Cys Ala Ile Ser Gly Asp Ser Leu Ser Ser Thr
20 25 30

Ser Ala Ala Trp Asn Trp Ile Arg Gln Ser Pro Ser Gly Gly Leu Glu
35 40 45

Trp Leu Gly Arg Thr Tyr Tyr Arg Ser Lys Trp Tyr Asn Asp Tyr Ala
50 55 60

Val Ser Val Lys Ser Arg Ile Thr Ile Asn Pro Asp Thr Ser Lys Asn
65 70 75 80

Gln Phe Ser Leu Gln Leu Asn Ser Val Thr Pro Glu Asp Thr Ser Val
85 90 95

Tyr Tyr Cys Ala Arg Asp Arg Gly Tyr Tyr Asn Gly Val Asp Val Trp
100 105 110

Gly Gln Gly Thr Met Val Thr Val Ser Ser Ala Ser Thr Lys Gly Pro
115 120 125

Ser Val Phe Pro Leu Ala Pro Ser Ser Lys Ser Thr Ser Gly Gly Thr
130 135 140

Ala Ala Leu Gly Cys Leu Val Lys Asp Tyr Phe Pro Glu Pro Val Thr
145 150 155 160

Val Ser Trp Asn Ser Gly Ala Leu Thr Ser Gly Val His Thr Phe Pro
165 170 175

Ala Val Leu Gln Ser Ser Gly Leu Tyr Ser Leu Ser Ser Val Val Thr
180 185 190

Val Pro Ser Ser Ser Leu Gly Thr Gln Thr Tyr Ile Cys Asn Val Asn
195 200 205

His Lys Pro Ser Asn Thr Lys Val Asp Lys Lys Val Glu Pro Lys Ser
210 215 220

Cys Asp Lys Thr His Thr Cys Pro Pro Cys Pro Ala Pro Glu Leu Leu
225 230 235 240

```
Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro
    450

<210> SEQ ID NO 10
<211> LENGTH: 212
<212> TYPE: PRT
<213> ORGANISM: Homo sapiens

<400> SEQUENCE: 10

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Ser Trp Tyr Gln Gln Arg Pro Gly Gln Ser Pro Leu Leu Val Ile Tyr
        35                  40                  45

Gln Asp Asn Lys Arg Pro Ser Gly Ile Pro Gln Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Phe Cys Gln Ala Trp Asp Ser Gly Thr Phe Val
                85                  90                  95

Phe Gly Thr Gly Thr Lys Val Thr Ile Leu Arg Gln Pro Lys Ala Asn
            100                 105                 110

Pro Thr Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
    130                 135                 140

Thr Val Ala Trp Lys Ala Asp Gly Ser Pro Val Lys Ala Gly Val Glu
145                 150                 155                 160
```

```
Thr Thr Lys Pro Ser Lys Gln Ser Asn Asn Lys Tyr Ala Ala Ser Ser
            165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
            195                 200                 205

Thr Glu Cys Ser
    210
```

<210> SEQ ID NO 11
<211> LENGTH: 448
<212> TYPE: PRT
<213> ORGANISM: Homo sapiens

<400> SEQUENCE: 11

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Ala Arg Ala Pro Gly His Tyr Tyr Gly Met Asp Val Trp Gly Gln
        100                 105                 110

Gly Thr Thr Val Thr Val Ser Ser Ala Ser Thr Lys Gly Pro Ser Val
    115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
    195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
```

```
                305                 310                 315                 320
Glu Tyr Lys Cys Lys Val Ser Asn Lys Ala Leu Pro Ala Pro Ile Glu
                    325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445
```

<210> SEQ ID NO 12
<211> LENGTH: 214
<212> TYPE: PRT
<213> ORGANISM: Homo sapiens

<400> SEQUENCE: 12

```
Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Glu Asp Lys Tyr Ala
                20                  25                  30

Ser Trp Tyr Gln Leu Lys Pro Gly His Ser Pro Val Leu Val Ile Tyr
            35                  40                  45

Gln Asp Ser Lys Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Arg Ala Trp Asp Ser Asn Thr Gly Asp
                85                  90                  95

Val Val Phe Gly Gly Gly Thr Lys Leu Thr Val Leu Arg Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210
```

<210> SEQ ID NO 13
<211> LENGTH: 452

<212> TYPE: PRT
<213> ORGANISM: Artificial Sequence
<220> FEATURE:
<223> OTHER INFORMATION: H chain of human/mouse chimeric and human/mouse corss-reactive anti-plexin A1 antibody hPANL#240-mFc

<400> SEQUENCE: 13

```
Gln Val Gln Leu Gln Gln Ser Gly Pro Gly Leu Val Lys Pro Ser Gln
  1               5                  10                  15

Thr Leu Ser Leu Thr Cys Ala Ile Ser Gly Asp Ser Leu Ser Ser Thr
             20                  25                  30

Ser Ala Ala Trp Asn Trp Ile Arg Gln Ser Pro Ser Gly Gly Leu Glu
         35                  40                  45

Trp Leu Gly Arg Thr Tyr Tyr Arg Ser Lys Trp Tyr Asn Asp Tyr Ala
     50                  55                  60

Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ser Val
             85                  90                  95

Tyr Tyr Cys Ala Arg Asp Arg Gly Tyr Tyr Asn Gly Val Asp Val Trp
        100                 105                 110

Gly Gln Gly Thr Met Val Thr Val Ser Ser Ala Lys Thr Thr Ala Pro
        115                 120                 125

Ser Val Tyr Pro Leu Ala Pro Val Cys Gly Asp Thr Thr Gly Ser Ser
        130                 135                 140

Val Thr Leu Gly Cys Leu Val Lys Gly Tyr Phe Pro Glu Pro Val Thr
145                 150                 155                 160

Leu Thr Trp Asn Ser Gly Ser Leu Ser Ser Gly Val His Thr Phe Pro
                165                 170                 175

Ala Val Leu Gln Ser Asp Leu Tyr Thr Leu Ser Ser Ser Val Thr Val
                180                 185                 190

Thr Ser Ser Thr Trp Pro Ser Gln Ser Ile Thr Cys Asn Val Ala His
                195                 200                 205

Pro Ala Ser Ser Thr Lys Val Asp Lys Lys Ile Glu Pro Arg Gly Pro
        210                 215                 220

Thr Ile Lys Pro Cys Pro Pro Cys Lys Cys Pro Ala Pro Asn Leu Arg
225                 230                 235                 240

Arg Gly Pro Lys Val Phe Ile Phe Pro Pro Lys Ile Lys Asp Val Leu
                245                 250                 255

Met Ile Ser Leu Ser Pro Ile Val Thr Cys Val Val Val Asp Val Ser
                260                 265                 270

Glu Asp Asp Pro Asp Val Gln Ile Ser Trp Phe Val Asn Asn Val Glu
            275                 280                 285

Val His Thr Ala Gln Thr Gln Thr His Arg Glu Asp Tyr Asn Ser Thr
        290                 295                 300

Leu Arg Val Val Ser Ala Leu Pro Ile Gln His Gln Asp Trp Met Ser
305                 310                 315                 320

Gly Lys Glu Phe Lys Cys Lys Val Asn Asn Lys Asp Leu Pro Ala Pro
                325                 330                 335

Ile Glu Arg Thr Ile Ser Lys Pro Lys Gly Ser Val Arg Ala Pro Gln
            340                 345                 350

Val Tyr Val Leu Pro Pro Pro Glu Glu Glu Met Thr Lys Lys Gln Val
        355                 360                 365

Thr Leu Thr Cys Met Val Thr Asp Phe Met Pro Glu Asp Ile Tyr Val
370                 375                 380
```

```
Glu Trp Thr Asn Asn Gly Lys Thr Glu Leu Asn Tyr Lys Asn Thr Glu
385                 390                 395                 400

Pro Val Leu Asp Ser Asp Gly Ser Tyr Phe Met Tyr Ser Lys Leu Arg
                405                 410                 415

Val Glu Lys Lys Asn Trp Val Glu Arg Asn Ser Tyr Ser Cys Ser Val
            420                 425                 430

Val His Glu Gly Leu His Asn His Thr Thr Lys Ser Phe Ser Arg
        435                 440                 445

Thr Pro Gly Lys
        450

<210> SEQ ID NO 14
<211> LENGTH: 450
<212> TYPE: PRT
<213> ORGANISM: Artificial Sequence
<220> FEATURE:
<223> OTHER INFORMATION: H chain of human/mouse chimeric and human/mouse
      corss-reactive anti-plexin A1 antibody 359B2-2-3-6-mFc

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ala Pro Gly His Tyr Tyr Tyr Gly Met Asp Val Trp Gly Gln
            100                 105                 110

Gly Thr Thr Val Thr Val Ser Ser Ala Lys Thr Thr Ala Pro Ser Val
        115                 120                 125

Tyr Pro Leu Ala Pro Val Cys Gly Asp Thr Thr Gly Ser Ser Val Thr
    130                 135                 140

Leu Gly Cys Leu Val Lys Gly Tyr Phe Pro Glu Pro Val Thr Leu Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Thr Ser
            180                 185                 190

Ser Thr Trp Pro Ser Gln Ser Ile Thr Cys Asn Val Ala His Pro Ala
        195                 200                 205

Ser Ser Thr Lys Val Asp Lys Lys Ile Glu Pro Arg Gly Pro Thr Ile
    210                 215                 220

Lys Pro Cys Pro Pro Cys Lys Cys Pro Ala Pro Asn Leu Arg Arg Gly
225                 230                 235                 240

Pro Lys Val Phe Ile Phe Pro Pro Lys Ile Lys Asp Val Leu Met Ile
                245                 250                 255

Ser Leu Ser Pro Ile Val Thr Cys Val Val Val Asp Val Ser Glu Asp
            260                 265                 270

Asp Pro Asp Val Gln Ile Ser Trp Phe Val Asn Asn Val Glu Val His
```

```
                275                 280                 285
Thr Ala Gln Thr Gln Thr His Arg Glu Asp Tyr Asn Ser Thr Leu Arg
290                 295                 300

Val Val Ser Ala Leu Pro Ile Gln His Gln Asp Trp Met Ser Gly Lys
305                 310                 315                 320

Glu Phe Lys Cys Lys Val Asn Asn Lys Asp Leu Pro Ala Pro Ile Glu
                325                 330                 335

Arg Thr Ile Ser Lys Pro Lys Gly Ser Val Arg Ala Pro Gln Val Tyr
            340                 345                 350

Val Leu Pro Pro Pro Glu Glu Glu Met Thr Lys Lys Gln Val Thr Leu
        355                 360                 365

Thr Cys Met Val Thr Asp Phe Met Pro Glu Asp Ile Tyr Val Glu Trp
370                 375                 380

Thr Asn Asn Gly Lys Thr Glu Leu Asn Tyr Lys Asn Thr Glu Pro Val
385                 390                 395                 400

Leu Asp Ser Asp Gly Ser Tyr Phe Met Tyr Ser Lys Leu Arg Val Glu
                405                 410                 415

Lys Lys Asn Trp Val Glu Arg Asn Ser Tyr Ser Cys Ser Val Val His
            420                 425                 430

Glu Gly Leu His Asn His His Thr Thr Lys Ser Phe Ser Arg Thr Pro
        435                 440                 445

Gly Lys
    450

<210> SEQ ID NO 15
<211> LENGTH: 1305
<212> TYPE: PRT
<213> ORGANISM: Artificial Sequence
<220> FEATURE:
<223> OTHER INFORMATION: Human plexin A1 recombinant protein

<400> SEQUENCE: 15

Met Trp Trp Arg Leu Trp Trp Leu Leu Leu Leu Leu Leu Leu Leu Trp
1               5                   10                  15

Pro Met Val Trp Ala Glu Ala Gly Leu Pro Arg Ala Gly Gly Gly Ser
            20                  25                  30

Gln Pro Pro Phe Arg Thr Phe Ser Ala Ser Asp Trp Gly Leu Thr His
        35                  40                  45

Leu Val Val His Glu Gln Thr Gly Glu Val Tyr Val Gly Ala Val Asn
    50                  55                  60

Arg Ile Tyr Lys Leu Ser Gly Asn Leu Thr Leu Leu Arg Ala His Val
65                  70                  75                  80

Thr Gly Pro Val Glu Asp Asn Glu Lys Cys Tyr Pro Pro Pro Ser Val
                85                  90                  95

Gln Ser Cys Pro His Gly Leu Gly Ser Thr Asp Asn Val Asn Lys Leu
            100                 105                 110

Leu Leu Leu Asp Tyr Ala Ala Asn Arg Leu Leu Ala Cys Gly Ser Ala
        115                 120                 125

Ser Gln Gly Ile Cys Gln Phe Leu Arg Leu Asp Asp Leu Phe Lys Leu
    130                 135                 140

Gly Glu Pro His His Arg Lys Glu His Tyr Leu Ser Ser Val Gln Glu
145                 150                 155                 160

Ala Gly Ser Met Ala Gly Val Leu Ile Ala Gly Pro Pro Gly Gln Gly
                165                 170                 175

Gln Ala Lys Leu Phe Val Gly Thr Pro Ile Asp Gly Lys Ser Glu Tyr
```

-continued

```
                180                 185                 190
Phe Pro Thr Leu Ser Ser Arg Arg Leu Met Ala Asn Glu Glu Asp Ala
            195                 200                 205
Asp Met Phe Gly Phe Val Tyr Gln Asp Glu Phe Val Ser Ser Gln Leu
        210                 215                 220
Lys Ile Pro Ser Asp Thr Leu Ser Lys Phe Pro Ala Phe Asp Ile Tyr
225                 230                 235                 240
Tyr Val Tyr Ser Phe Arg Ser Glu Gln Phe Val Tyr Tyr Leu Thr Leu
                245                 250                 255
Gln Leu Asp Thr Gln Leu Thr Ser Pro Asp Ala Ala Gly Glu His Phe
            260                 265                 270
Phe Thr Ser Lys Ile Val Arg Leu Cys Val Asp Asp Pro Lys Phe Tyr
        275                 280                 285
Ser Tyr Val Glu Phe Pro Ile Gly Cys Glu Gln Ala Gly Val Glu Tyr
    290                 295                 300
Arg Leu Val Gln Asp Ala Tyr Leu Ser Arg Pro Gly Arg Ala Leu Ala
305                 310                 315                 320
His Gln Leu Gly Leu Ala Glu Asp Glu Asp Val Leu Phe Thr Val Phe
                325                 330                 335
Ala Gln Gly Gln Lys Asn Arg Val Lys Pro Pro Lys Glu Ser Ala Leu
            340                 345                 350
Cys Leu Phe Thr Leu Arg Ala Ile Lys Glu Lys Ile Lys Glu Arg Ile
        355                 360                 365
Gln Ser Cys Tyr Arg Gly Glu Gly Lys Leu Ser Leu Pro Trp Leu Leu
    370                 375                 380
Asn Lys Glu Leu Gly Cys Ile Asn Ser Pro Leu Gln Ile Asp Asp Asp
385                 390                 395                 400
Phe Cys Gly Gln Asp Phe Asn Gln Pro Leu Gly Gly Thr Val Thr Ile
                405                 410                 415
Glu Gly Thr Pro Leu Phe Val Asp Lys Asp Asp Gly Leu Thr Ala Val
            420                 425                 430
Ala Ala Tyr Asp Tyr Arg Gly Arg Thr Val Val Phe Ala Gly Thr Arg
        435                 440                 445
Ser Gly Arg Ile Arg Lys Ile Leu Val Asp Leu Ser Asn Pro Gly Gly
    450                 455                 460
Arg Pro Ala Leu Ala Tyr Glu Ser Val Val Ala Gln Glu Gly Ser Pro
465                 470                 475                 480
Ile Leu Arg Asp Leu Val Leu Ser Pro Asn His Gln Tyr Leu Tyr Ala
                485                 490                 495
Met Thr Glu Lys Gln Val Thr Arg Val Pro Val Glu Ser Cys Val Gln
            500                 505                 510
Tyr Thr Ser Cys Glu Leu Cys Leu Gly Ser Arg Asp Pro His Cys Gly
        515                 520                 525
Trp Cys Val Leu His Ser Ile Cys Ser Arg Arg Asp Ala Cys Glu Arg
    530                 535                 540
Ala Asp Glu Pro Gln Arg Phe Ala Ala Asp Leu Leu Gln Cys Val Gln
545                 550                 555                 560
Leu Thr Val Gln Pro Arg Asn Val Ser Val Thr Met Ser Gln Val Pro
                565                 570                 575
Leu Val Leu Gln Ala Trp Asn Val Pro Asp Leu Ser Ala Gly Val Asn
            580                 585                 590
Cys Ser Phe Glu Asp Phe Thr Glu Ser Glu Ser Val Leu Glu Asp Gly
        595                 600                 605
```

-continued

Arg Ile His Cys Arg Ser Pro Ser Ala Arg Glu Val Ala Pro Ile Thr
610                 615                 620

Arg Gly Gln Gly Asp Gln Arg Val Val Lys Leu Tyr Leu Lys Ser Lys
625                 630                 635                 640

Glu Thr Gly Lys Lys Phe Ala Ser Val Asp Phe Val Phe Tyr Asn Cys
                645                 650                 655

Ser Val His Gln Ser Cys Leu Ser Cys Val Asn Gly Ser Phe Pro Cys
            660                 665                 670

His Trp Cys Lys Tyr Arg His Val Cys Thr His Asn Val Ala Asp Cys
        675                 680                 685

Ala Phe Leu Glu Gly Arg Val Asn Val Ser Glu Asp Cys Pro Gln Ile
690                 695                 700

Leu Pro Ser Thr Gln Ile Tyr Val Pro Val Gly Val Val Lys Pro Ile
705                 710                 715                 720

Thr Leu Ala Ala Arg Asn Leu Pro Gln Pro Gln Ser Gly Gln Arg Gly
                725                 730                 735

Tyr Glu Cys Leu Phe His Ile Pro Gly Ser Pro Ala Arg Val Thr Ala
            740                 745                 750

Leu Arg Phe Asn Ser Ser Leu Gln Cys Gln Asn Ser Ser Tyr Ser
        755                 760                 765

Tyr Glu Gly Asn Asp Val Ser Asp Leu Pro Val Asn Leu Ser Val Val
770                 775                 780

Trp Asn Gly Asn Phe Val Ile Asp Asn Pro Gln Asn Ile Gln Ala His
785                 790                 795                 800

Leu Tyr Lys Cys Pro Ala Leu Arg Glu Ser Cys Gly Leu Cys Leu Lys
                805                 810                 815

Ala Asp Pro Arg Phe Glu Cys Gly Trp Cys Val Ala Glu Arg Arg Cys
            820                 825                 830

Ser Leu Arg His His Cys Ala Ala Asp Thr Pro Ala Ser Trp Met His
        835                 840                 845

Ala Arg His Gly Ser Ser Arg Cys Thr Asp Pro Lys Ile Leu Lys Leu
850                 855                 860

Ser Pro Glu Thr Gly Pro Arg Gln Gly Gly Thr Arg Leu Thr Ile Thr
865                 870                 875                 880

Gly Glu Asn Leu Gly Leu Arg Phe Glu Asp Val Arg Leu Gly Val Arg
                885                 890                 895

Val Gly Lys Val Leu Cys Ser Pro Val Glu Ser Glu Tyr Ile Ser Ala
            900                 905                 910

Glu Gln Ile Val Cys Glu Ile Gly Asp Ala Ser Ser Val Arg Ala His
        915                 920                 925

Asp Ala Leu Val Glu Val Cys Val Arg Asp Cys Ser Pro His Tyr Arg
930                 935                 940

Ala Leu Ser Pro Lys Arg Phe Thr Phe Val Thr Pro Thr Phe Tyr Arg
945                 950                 955                 960

Val Ser Pro Ser Arg Gly Pro Leu Ser Gly Thr Trp Ile Gly Ile
                965                 970                 975

Glu Gly Ser His Leu Asn Ala Gly Ser Asp Val Ala Val Ser Val Gly
            980                 985                 990

Gly Arg Pro Cys Ser Phe Ser Trp Arg Asn Ser Arg Glu Ile Arg Cys
        995                 1000                1005

Leu Thr Pro Pro Gly Gln Ser Pro Gly Ser Ala Pro Ile Ile Ile
    1010                1015                1020

Asn Ile Asn Arg Ala Gln Leu Thr Asn Pro Glu Val Lys Tyr Asn
1025                1030                1035

Tyr Thr Glu Asp Pro Thr Ile Leu Arg Ile Asp Pro Glu Trp Ser
    1040                1045                1050

Ile Asn Ser Gly Gly Thr Leu Leu Thr Val Thr Gly Thr Asn Leu
    1055                1060                1065

Ala Thr Val Arg Glu Pro Arg Ile Arg Ala Lys Tyr Gly Gly Ile
    1070                1075                1080

Glu Arg Glu Asn Gly Cys Leu Val Tyr Asn Asp Thr Thr Met Val
    1085                1090                1095

Cys Arg Ala Pro Ser Val Ala Asn Pro Val Arg Ser Pro Pro Glu
    1100                1105                1110

Leu Gly Glu Arg Pro Asp Glu Leu Gly Phe Val Met Asp Asn Val
    1115                1120                1125

Arg Ser Leu Leu Val Leu Asn Ser Thr Ser Phe Leu Tyr Tyr Pro
    1130                1135                1140

Asp Pro Val Leu Glu Pro Leu Ser Pro Thr Gly Leu Leu Glu Leu
    1145                1150                1155

Lys Pro Ser Ser Pro Leu Ile Leu Lys Gly Arg Asn Leu Leu Pro
    1160                1165                1170

Pro Ala Pro Gly Asn Ser Arg Leu Asn Tyr Thr Val Leu Ile Gly
    1175                1180                1185

Ser Thr Pro Cys Thr Leu Thr Val Ser Glu Thr Gln Leu Leu Cys
    1190                1195                1200

Glu Ala Pro Asn Leu Thr Gly Gln His Lys Val Thr Val Arg Ala
    1205                1210                1215

Gly Gly Phe Glu Phe Ser Pro Gly Thr Leu Gln Val Tyr Ser Asp
    1220                1225                1230

Ser Leu Leu Thr Leu Pro Ala Ile Val Gly Ile Gly Gly Gly Gly
    1235                1240                1245

Gly Leu Leu Leu Leu Val Ile Val Ala Val Leu Ile Ala Tyr Lys
    1250                1255                1260

Arg Lys Ser Arg Asp Ala Asp Arg Thr Leu Lys Arg Leu Gln Leu
    1265                1270                1275

Gln Met Asp Asn Leu Glu Ser Arg Val Ala Leu Glu Cys Lys Glu
    1280                1285                1290

Ala Phe Glu Gln Lys Leu Ile Ser Glu Glu Asp Leu
    1295                1300                1305

<210> SEQ ID NO 16
<211> LENGTH: 1247
<212> TYPE: PRT
<213> ORGANISM: Artificial Sequence
<220> FEATURE:
<223> OTHER INFORMATION: Soluble mouse plexin A1 protein

<400> SEQUENCE: 16

Met Trp Trp Arg Leu Trp Trp Leu Leu Leu Leu Leu Leu Leu Trp
1               5                   10                  15

Pro Met Val Trp Ala Ala Ile Ser Ser Pro Pro Ala Gly Leu Gly Pro
                20                  25                  30

Gln Pro Ala Phe Arg Thr Phe Val Ala Ser Asp Trp Gly Leu Thr His
            35                  40                  45

Leu Val Val His Glu Gln Thr Gly Glu Val Tyr Val Gly Ala Val Asn
    50                  55                  60

-continued

```
Arg Ile Tyr Lys Leu Ser Gly Asn Leu Thr Leu Arg Ala His Val
 65                  70                  75                  80

Thr Gly Pro Val Glu Asp Asn Glu Lys Cys Tyr Pro Pro Ser Val
                 85                  90                  95

Gln Ser Cys Pro His Gly Leu Gly Ser Thr Asp Asn Val Asn Lys Leu
            100                 105                 110

Leu Leu Leu Asp Tyr Ala Ala Asn Arg Leu Leu Ala Cys Gly Ser Ala
        115                 120                 125

Ser Gln Gly Ile Cys Gln Phe Leu Arg Leu Asp Asp Leu Phe Lys Leu
    130                 135                 140

Gly Glu Pro His His Arg Lys Glu His Tyr Leu Ser Ser Val Arg Glu
145                 150                 155                 160

Ala Gly Ser Met Ala Gly Val Leu Ile Ala Gly Pro Pro Gly Gln Gly
                165                 170                 175

Gln Ala Lys Leu Phe Val Gly Thr Pro Ile Asp Gly Lys Ser Glu Tyr
            180                 185                 190

Phe Pro Thr Leu Ser Ser Arg Arg Leu Met Ala Asn Glu Glu Asp Ala
        195                 200                 205

Asp Met Phe Gly Phe Val Tyr Gln Asp Glu Phe Val Ser Ser Gln Leu
    210                 215                 220

Lys Ile Pro Ser Asp Thr Leu Ser Lys Phe Pro Ala Phe Asp Ile Tyr
225                 230                 235                 240

Tyr Val Tyr Ser Phe Arg Ser Glu Gln Phe Val Tyr Tyr Leu Thr Leu
                245                 250                 255

Gln Leu Asp Thr Gln Leu Thr Ser Pro Asp Ala Ala Gly Glu His Phe
            260                 265                 270

Phe Thr Ser Lys Ile Val Arg Leu Cys Val Asn Asp Pro Lys Phe Tyr
        275                 280                 285

Ser Tyr Val Glu Phe Pro Ile Gly Cys Glu Gln Ala Gly Val Glu Tyr
    290                 295                 300

Arg Leu Val Gln Asp Ala Tyr Leu Ser Arg Pro Gly Gln Ala Leu Ala
305                 310                 315                 320

Lys Gln Leu Gly Leu Ala Glu Asp Glu Glu Val Leu Phe Thr Val Phe
                325                 330                 335

Ala Gln Gly Gln Lys Asn Arg Val Lys Pro Pro Lys Glu Ser Ala Leu
            340                 345                 350

Cys Leu Phe Thr Leu Arg Ala Ile Lys Glu Lys Ile Lys Glu Arg Ile
        355                 360                 365

Gln Ser Cys Tyr Arg Gly Glu Gly Lys Leu Ser Leu Pro Trp Leu Leu
    370                 375                 380

Asn Lys Glu Leu Gly Cys Ile Asn Ser Pro Leu Gln Ile Asp Asp
385                 390                 395                 400

Phe Cys Gly Gln Asp Phe Asn Gln Pro Leu Gly Gly Thr Val Thr Ile
                405                 410                 415

Glu Gly Thr Pro Leu Phe Val Asp Lys Glu Asp Gly Leu Thr Ala Val
            420                 425                 430

Ala Ala Tyr Asp Tyr Gln Gly Arg Thr Val Val Phe Ala Gly Thr Arg
        435                 440                 445

Ser Gly Arg Ile Arg Lys Ile Leu Val Asp Leu Ala Asn Pro Ser Gly
    450                 455                 460

Arg Pro Ala Leu Ala Tyr Glu Ser Val Val Ala Gln Glu Gly Asn Pro
465                 470                 475                 480

Ile Leu Arg Asp Leu Val Leu Ser Pro Asn Arg Gln Tyr Leu Tyr Ala
```

-continued

```
                485                 490                 495
Met Thr Glu Lys Gln Val Thr Gln Val Pro Val Glu Ser Cys Val Gln
                500                 505                 510
Tyr Thr Ser Cys Glu Leu Cys Leu Gly Ser Arg Asp Pro His Cys Gly
                515                 520                 525
Trp Cys Val Leu His Ser Ile Cys Ser Arg Gln Asp Ala Cys Glu Arg
                530                 535                 540
Ala Glu Glu Pro Gln Arg Phe Ala Ser Asp Leu Leu Gln Cys Val Gln
545                 550                 555                 560
Leu Thr Val Gln Pro Arg Asn Val Ser Val Thr Met Ser Gln Val Pro
                565                 570                 575
Leu Val Leu Gln Ala Trp Asn Val Pro Asp Leu Ser Ala Gly Val Asn
                580                 585                 590
Cys Ser Phe Glu Asp Phe Thr Glu Thr Glu Ser Ile Leu Glu Asp Gly
                595                 600                 605
Arg Ile His Cys His Ser Pro Ser Ala Arg Glu Val Ala Pro Ile Thr
                610                 615                 620
Gln Gly Gln Gly Asp Gln Arg Val Val Lys Leu Tyr Leu Lys Ser Lys
625                 630                 635                 640
Glu Thr Gly Lys Lys Phe Ala Ser Val Asp Phe Val Phe Tyr Asn Cys
                645                 650                 655
Ser Val His Gln Ser Cys Leu Ala Cys Val Asn Gly Ser Phe Pro Cys
                660                 665                 670
His Trp Cys Lys Tyr Arg His Val Cys Thr Asn Asn Ala Ala Asp Cys
                675                 680                 685
Ala Phe Leu Glu Gly Arg Val Asn Met Ser Glu Asp Cys Pro Gln Ile
                690                 695                 700
Leu Pro Ser Thr His Ile Tyr Val Pro Val Gly Val Val Lys Pro Ile
705                 710                 715                 720
Thr Leu Ala Ala Arg Asn Leu Pro Gln Pro Gln Ser Gly Gln Arg Gly
                725                 730                 735
Tyr Glu Cys Leu Phe His Ile Pro Gly Ser Pro Ala Arg Val Thr Ala
                740                 745                 750
Leu Arg Phe Asn Ser Ser Ser Leu Gln Cys Gln Asn Ser Ser Tyr Ser
                755                 760                 765
Tyr Glu Gly Asn Asp Val Ser Asp Leu Pro Val Asn Leu Ser Val Val
                770                 775                 780
Trp Asn Gly Asn Phe Val Ile Asp Asn Pro Gln Asn Ile Gln Ala His
785                 790                 795                 800
Leu Tyr Lys Cys Pro Ala Leu Arg Gln Ser Cys Gly Leu Cys Leu Lys
                805                 810                 815
Ala Asp Pro Arg Phe Glu Cys Gly Trp Cys Val Ala Glu Arg Arg Cys
                820                 825                 830
Ser Leu Arg His His Cys Pro Ala Asp Ser Pro Ala Ser Trp Met His
                835                 840                 845
Ala His His Gly Ser Ser Arg Cys Thr Asp Pro Lys Ile Leu Lys Leu
                850                 855                 860
Ser Pro Glu Thr Gly Pro Arg Gln Gly Gly Thr Arg Leu Thr Ile Thr
865                 870                 875                 880
Gly Glu Asn Leu Gly Leu Arg Phe Glu Asp Val Arg Leu Gly Val His
                885                 890                 895
Val Gly Lys Val Leu Cys Ser Pro Val Glu Ser Glu Tyr Ile Ser Ala
                900                 905                 910
```

Glu Gln Ile Val Cys Glu Ile Gly Asp Ala Ser Thr Leu Arg Ala His
            915                 920                 925

Asp Ala Leu Val Glu Val Cys Val Arg Asp Cys Ser Leu His Tyr Arg
        930                 935                 940

Ala Leu Ser Pro Lys Arg Phe Thr Phe Val Thr Pro Thr Phe Tyr Arg
945                 950                 955                 960

Val Ser Pro Ser Arg Gly Pro Leu Ser Gly Gly Thr Trp Ile Gly Ile
            965                 970                 975

Glu Gly Ser His Leu Asn Ala Gly Ser Asp Val Ala Val Ser Ile Gly
        980                 985                 990

Gly Arg Pro Cys Ser Phe Ser Trp Arg Asn Ser Arg Glu Ile Arg Cys
            995                 1000                1005

Leu Thr Pro Pro Gly His Thr Pro Gly Ser Ala Pro Ile Val Ile
        1010                1015                1020

Asn Ile Asn Arg Ala Gln Leu Ser Asn Pro Glu Val Lys Tyr Asn
        1025                1030                1035

Tyr Thr Glu Asp Pro Thr Ile Leu Arg Ile Asp Pro Glu Trp Ser
        1040                1045                1050

Ile Asn Ser Gly Gly Thr Leu Leu Thr Val Thr Gly Thr Asn Leu
        1055                1060                1065

Ala Thr Val Arg Glu Pro Arg Ile Arg Ala Lys Tyr Gly Gly Ile
        1070                1075                1080

Glu Arg Glu Asn Ser Cys Met Val Tyr Asn Asp Thr Thr Met Val
        1085                1090                1095

Cys Arg Ala Pro Ser Ile Asp Asn Pro Lys Arg Ser Pro Pro Glu
        1100                1105                1110

Leu Gly Glu Arg Pro Asp Glu Ile Gly Phe Ile Met Asp Asn Val
        1115                1120                1125

Arg Thr Leu Leu Val Leu Asn Ser Ser Ser Phe Leu Tyr Tyr Pro
        1130                1135                1140

Asp Pro Val Leu Glu Pro Leu Ser Pro Thr Gly Leu Leu Glu Leu
        1145                1150                1155

Lys Pro Ser Ser Pro Leu Ile Leu Lys Gly Arg Asn Leu Leu Pro
        1160                1165                1170

Pro Ala Pro Gly Asn Ser Arg Leu Asn Tyr Thr Val Leu Ile Gly
        1175                1180                1185

Ser Thr Pro Cys Ile Leu Thr Val Ser Glu Thr Gln Leu Leu Cys
        1190                1195                1200

Glu Ala Pro Asn Leu Thr Gly Gln His Lys Val Thr Val Arg Ala
        1205                1210                1215

Gly Gly Phe Glu Phe Ser Pro Gly Met Leu Gln Val Tyr Ser Asp
        1220                1225                1230

Ser Leu Leu Thr Leu Pro Asp Tyr Lys Asp Asp Asp Lys
        1235                1240                1245

<210> SEQ ID NO 17
<211> LENGTH: 323
<212> TYPE: PRT
<213> ORGANISM: Oryctolagus cuniculus

<400> SEQUENCE: 17

Gly Gln Pro Lys Ala Pro Ser Val Phe Pro Leu Ala Pro Cys Cys Gly
1               5                   10                  15

Asp Thr Pro Ser Ser Thr Val Thr Leu Gly Cys Leu Val Lys Gly Tyr

```
            20                  25                  30
Leu Pro Glu Pro Val Thr Val Thr Trp Asn Ser Gly Thr Leu Thr Asn
            35                  40                  45
Gly Val Arg Thr Phe Pro Ser Val Arg Gln Ser Ser Gly Leu Tyr Ser
        50                  55                  60
Leu Ser Ser Val Val Ser Val Thr Ser Ser Ser Gln Pro Val Thr Cys
 65                  70                  75                  80
Asn Val Ala His Pro Ala Thr Asn Thr Lys Val Asp Lys Thr Val Ala
                85                  90                  95
Pro Ser Thr Cys Ser Lys Pro Met Cys Pro Pro Pro Glu Leu Leu Gly
            100                 105                 110
Gly Pro Ser Val Phe Ile Phe Pro Pro Lys Pro Lys Asp Thr Leu Met
            115                 120                 125
Ile Ser Arg Thr Pro Glu Val Thr Cys Val Val Val Asp Val Ser Gln
            130                 135                 140
Asp Asp Pro Glu Val Gln Phe Thr Trp Tyr Ile Asn Asn Glu Gln Val
145                 150                 155                 160
Arg Thr Ala Arg Pro Pro Leu Arg Glu Gln Gln Phe Asn Ser Thr Ile
                165                 170                 175
Arg Val Val Ser Thr Leu Pro Ile Ala His Gln Asp Trp Leu Arg Gly
                180                 185                 190
Lys Glu Phe Lys Cys Lys Val His Asn Lys Ala Leu Pro Ala Pro Ile
                195                 200                 205
Glu Lys Thr Ile Ser Lys Ala Arg Gly Gln Pro Leu Glu Pro Lys Val
            210                 215                 220
Tyr Thr Met Gly Pro Pro Arg Glu Glu Leu Ser Ser Arg Ser Val Ser
225                 230                 235                 240
Leu Thr Cys Met Ile Asn Gly Phe Tyr Pro Ser Asp Ile Ser Val Glu
                245                 250                 255
Trp Glu Lys Asn Gly Lys Ala Glu Asp Asn Tyr Lys Thr Thr Pro Thr
                260                 265                 270
Val Leu Asp Ser Asp Gly Ser Tyr Phe Leu Tyr Ser Lys Leu Ser Val
            275                 280                 285
Pro Thr Ser Glu Trp Gln Arg Gly Asp Val Phe Thr Cys Ser Val Met
            290                 295                 300
His Glu Ala Leu His Asn His Tyr Thr Gln Lys Ser Ile Ser Arg Ser
305                 310                 315                 320
Pro Gly Lys

<210> SEQ ID NO 18
<211> LENGTH: 104
<212> TYPE: PRT
<213> ORGANISM: Oryctolagus cuniculus

<400> SEQUENCE: 18

Gly Asp Pro Val Ala Pro Thr Val Leu Ile Phe Pro Pro Ala Ala Asp
 1               5                  10                  15
Gln Val Ala Thr Gly Thr Val Thr Ile Val Cys Val Ala Asn Lys Tyr
            20                  25                  30
Phe Pro Asp Val Thr Val Thr Trp Glu Val Asp Gly Thr Thr Gln Thr
            35                  40                  45
Thr Gly Ile Glu Asn Ser Lys Thr Pro Gln Asn Ser Ala Asp Cys Thr
        50                  55                  60
Tyr Asn Leu Ser Ser Thr Leu Thr Leu Thr Ser Thr Gln Tyr Asn Ser
```

```
                65                  70                  75                  80
His Lys Glu Tyr Thr Cys Lys Val Thr Gln Gly Thr Thr Ser Val Val
                    85                  90                  95

Gln Ser Phe Asn Arg Gly Asp Cys
                100
```

<210> SEQ ID NO 19
<211> LENGTH: 124
<212> TYPE: PRT
<213> ORGANISM: Oryctolagus cuniculus

<400> SEQUENCE: 19

```
Gln Ser Leu Glu Glu Ser Gly Gly Asp Leu Val Lys Pro Glu Gly Ser
1               5                   10                  15

Leu Thr Leu Ser Cys Thr Ala Ser Gly Phe Thr Ile Ser Ser Ser Tyr
                20                  25                  30

Trp Ile Cys Trp Val Arg Gln Ala Pro Gly Lys Gly Leu Glu Trp Ile
                35                  40                  45

Ala Cys Ile Tyr Val Gly Ser Gly Asp Gly Tyr Thr Tyr Tyr Ala Ser
        50                  55                  60

Trp Ala Lys Gly Arg Phe Thr Ile Ser Lys Thr Ser Ser Thr Thr Val
65                  70                  75                  80

Thr Leu Arg Met Thr Ser Leu Thr Ala Ala Asp Thr Ala Thr Tyr Phe
                85                  90                  95

Cys Ala Arg Gly Gly Asp Gly Val Gly Phe Asp Phe Asp
                100                 105                 110

Pro Trp Gly Pro Gly Thr Leu Val Thr Val Ser Ser
                115                 120
```

<210> SEQ ID NO 20
<211> LENGTH: 109
<212> TYPE: PRT
<213> ORGANISM: Oryctolagus cuniculus

<400> SEQUENCE: 20

```
Asp Val Val Leu Thr Gln Thr Pro Ala Ser Val Ser Glu Pro Val Gly
1               5                   10                  15

Gly Thr Val Thr Ile Lys Cys Gln Ala Thr Glu Ser Ile Asn Arg Asn
                20                  25                  30

Cys Ala Trp Tyr Gln Gln Lys Pro Gly Gln Pro Pro Lys Leu Leu Ile
                35                  40                  45

Tyr Arg Ala Ser Thr Leu Ala Ser Gly Val Pro Ser Arg Phe Lys Gly
        50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Cys Thr Asp Tyr Gly Thr Tyr
                85                  90                  95

Tyr Val Ala Phe Gly Gly Gly Thr Glu Val Val Val Lys
                100                 105
```

<210> SEQ ID NO 21
<211> LENGTH: 122
<212> TYPE: PRT
<213> ORGANISM: Homo sapiens

<400> SEQUENCE: 21

```
Gln Val Gln Leu Gln Gln Ser Gly Pro Gly Leu Val Lys Pro Ser Gln
1               5                   10                  15
```

Thr Leu Ser Leu Thr Cys Ala Ile Ser Gly Asp Ser Leu Ser Ser Thr
            20                  25                  30

Ser Ala Ala Trp Asn Trp Ile Arg Gln Ser Pro Ser Gly Gly Leu Glu
            35                  40                  45

Trp Leu Gly Arg Thr Tyr Tyr Arg Ser Lys Trp Tyr Asn Asp Tyr Ala
50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ser Val
                85                  90                  95

Tyr Tyr Cys Ala Arg Asp Arg Gly Tyr Tyr Asn Gly Val Asp Val Trp
            100                 105                 110

Gly Gln Gly Thr Met Val Thr Val Ser Ser
            115                 120

<210> SEQ ID NO 22
<211> LENGTH: 106
<212> TYPE: PRT
<213> ORGANISM: Homo sapiens

<400> SEQUENCE: 22

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Ser Trp Tyr Gln Gln Arg Pro Gly Gln Ser Pro Leu Leu Val Ile Tyr
            35                  40                  45

Gln Asp Asn Lys Arg Pro Ser Gly Ile Pro Gln Arg Phe Ser Gly Ser
50                  55                  60

Asn Ser Gly Asn Thr Ala Thr Leu Thr Ile Ser Gly Thr Gln Ala Met
65                  70                  75                  80

Asp Glu Ala Asp Tyr Phe Cys Gln Ala Trp Asp Ser Gly Thr Phe Val
                85                  90                  95

Phe Gly Thr Gly Thr Lys Val Thr Ile Leu
            100                 105

<210> SEQ ID NO 23
<211> LENGTH: 7
<212> TYPE: PRT
<213> ORGANISM: Homo sapiens

<400> SEQUENCE: 23

Ser Thr Ser Ala Ala Trp Asn
1               5

<210> SEQ ID NO 24
<211> LENGTH: 18
<212> TYPE: PRT
<213> ORGANISM: Homo sapiens

<400> SEQUENCE: 24

Arg Thr Tyr Tyr Arg Ser Lys Trp Tyr Asn Asp Tyr Ala Val Ser Val
1               5                   10                  15

Lys Ser

<210> SEQ ID NO 25
<211> LENGTH: 10
<212> TYPE: PRT

```
<213> ORGANISM: Homo sapiens

<400> SEQUENCE: 25

Asp Arg Gly Tyr Tyr Asn Gly Val Asp Val
1               5                   10

<210> SEQ ID NO 26
<211> LENGTH: 11
<212> TYPE: PRT
<213> ORGANISM: Homo sapiens

<400> SEQUENCE: 26

Ser Gly Asp Lys Leu Gly Asp Lys Tyr Ala Ser
1               5                   10

<210> SEQ ID NO 27
<211> LENGTH: 7
<212> TYPE: PRT
<213> ORGANISM: Homo sapiens

<400> SEQUENCE: 27

Gln Asp Asn Lys Arg Pro Ser
1               5

<210> SEQ ID NO 28
<211> LENGTH: 9
<212> TYPE: PRT
<213> ORGANISM: Homo sapiens

<400> SEQUENCE: 28

Gln Ala Trp Asp Ser Gly Thr Phe Val
1               5

<210> SEQ ID NO 29
<211> LENGTH: 5
<212> TYPE: PRT
<213> ORGANISM: Homo sapiens

<400> SEQUENCE: 29

Ser Tyr Tyr Met His
1               5

<210> SEQ ID NO 30
<211> LENGTH: 17
<212> TYPE: PRT
<213> ORGANISM: Homo sapiens

<400> SEQUENCE: 30

Ile Ile Asn Pro Ser Gly Gly Ser Thr Ser Tyr Ala Gln Lys Phe Gln
1               5                   10                  15

Gly

<210> SEQ ID NO 31
<211> LENGTH: 11
<212> TYPE: PRT
<213> ORGANISM: Homo sapiens

<400> SEQUENCE: 31

Ala Pro Gly His Tyr Tyr Tyr Gly Met Asp Val
1               5                   10

<210> SEQ ID NO 32
<211> LENGTH: 11
<212> TYPE: PRT
```

```
<213> ORGANISM: Homo sapiens

<400> SEQUENCE: 32

Ser Gly Asp Lys Leu Glu Asp Lys Tyr Ala Ser
1               5                   10

<210> SEQ ID NO 33
<211> LENGTH: 7
<212> TYPE: PRT
<213> ORGANISM: Homo sapiens

<400> SEQUENCE: 33

Gln Asp Ser Lys Arg Pro Ser
1               5

<210> SEQ ID NO 34
<211> LENGTH: 11
<212> TYPE: PRT
<213> ORGANISM: Homo sapiens

<400> SEQUENCE: 34

Arg Ala Trp Asp Ser Asn Thr Gly Asp Val Val
1               5                   10

<210> SEQ ID NO 35
<211> LENGTH: 120
<212> TYPE: PRT
<213> ORGANISM: Homo sapiens

<400> SEQUENCE: 35

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ala Pro Gly His Tyr Tyr Gly Met Asp Val Trp Gly Gln
            100                 105                 110

Gly Thr Thr Val Thr Val Ser Ser
            115                 120

<210> SEQ ID NO 36
<211> LENGTH: 108
<212> TYPE: PRT
<213> ORGANISM: Homo sapiens

<400> SEQUENCE: 36

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Glu Asp Lys Tyr Ala
                20                  25                  30

Ser Trp Tyr Gln Leu Lys Pro Gly His Ser Pro Val Leu Val Ile Tyr
            35                  40                  45

Gln Asp Ser Lys Arg Pro Ser Gly Ile Pro Glu Arg Phe Ser Gly Ser
```

```
                  50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Arg Ala Trp Asp Ser Asn Thr Gly Asp
                 85                  90                  95

Val Val Phe Gly Gly Gly Thr Lys Leu Thr Val Leu
                100                 105

<210> SEQ ID NO 37
<211> LENGTH: 1297
<212> TYPE: PRT
<213> ORGANISM: Artificial Sequence
<220> FEATURE:
<223> OTHER INFORMATION: Mouse plexin A1 recombinant protein

<400> SEQUENCE: 37

Met Trp Trp Arg Leu Trp Trp Leu Leu Leu Leu Leu Leu Leu Leu Trp
 1               5                  10                  15

Pro Met Val Trp Ala Ala Ile Ser Ser Pro Ala Gly Leu Gly Pro
                 20                  25                  30

Gln Pro Ala Phe Arg Thr Phe Val Ala Ser Asp Trp Gly Leu Thr His
                 35                  40                  45

Leu Val Val His Glu Gln Thr Gly Glu Val Tyr Val Gly Ala Val Asn
 50                  55                  60

Arg Ile Tyr Lys Leu Ser Gly Asn Leu Thr Leu Arg Ala His Val
 65                  70                  75                  80

Thr Gly Pro Val Glu Asp Asn Glu Lys Cys Tyr Pro Pro Pro Ser Val
                 85                  90                  95

Gln Ser Cys Pro His Gly Leu Gly Ser Thr Asp Asn Val Asn Lys Leu
                100                 105                 110

Leu Leu Leu Asp Tyr Ala Ala Asn Arg Leu Leu Ala Cys Gly Ser Ala
                115                 120                 125

Ser Gln Gly Ile Cys Gln Phe Leu Arg Leu Asp Asp Leu Phe Lys Leu
                130                 135                 140

Gly Glu Pro His His Arg Lys Glu His Tyr Leu Ser Ser Val Arg Glu
145                 150                 155                 160

Ala Gly Ser Met Ala Gly Val Leu Ile Ala Gly Pro Pro Gly Gln Gly
                165                 170                 175

Gln Ala Lys Leu Phe Val Gly Thr Pro Ile Asp Gly Lys Ser Glu Tyr
                180                 185                 190

Phe Pro Thr Leu Ser Ser Arg Arg Leu Met Ala Asn Glu Glu Asp Ala
                195                 200                 205

Asp Met Phe Gly Phe Val Tyr Gln Asp Glu Phe Val Ser Ser Gln Leu
                210                 215                 220

Lys Ile Pro Ser Asp Thr Leu Ser Lys Phe Pro Ala Phe Asp Ile Tyr
225                 230                 235                 240

Tyr Val Tyr Ser Phe Arg Ser Glu Gln Phe Val Tyr Tyr Leu Thr Leu
                245                 250                 255

Gln Leu Asp Thr Gln Leu Thr Ser Pro Asp Ala Ala Gly Glu His Phe
                260                 265                 270

Phe Thr Ser Lys Ile Val Arg Leu Cys Val Asn Asp Pro Lys Phe Tyr
                275                 280                 285

Ser Tyr Val Glu Phe Pro Ile Gly Cys Glu Gln Ala Gly Val Glu Tyr
                290                 295                 300

Arg Leu Val Gln Asp Ala Tyr Leu Ser Arg Pro Gly Gln Ala Leu Ala
```

```
            305                 310                 315                 320
Lys Gln Leu Gly Leu Ala Glu Asp Glu Val Leu Phe Thr Val Phe
                325                 330                 335

Ala Gln Gly Gln Lys Asn Arg Val Lys Pro Lys Glu Ser Ala Leu
                340                 345                 350

Cys Leu Phe Thr Leu Arg Ala Ile Lys Glu Lys Ile Lys Glu Arg Ile
                355                 360                 365

Gln Ser Cys Tyr Arg Gly Glu Gly Lys Leu Ser Leu Pro Trp Leu Leu
                370                 375                 380

Asn Lys Glu Leu Gly Cys Ile Asn Ser Pro Leu Gln Ile Asp Asp Asp
385                             390                 395                 400

Phe Cys Gly Gln Asp Phe Asn Gln Pro Leu Gly Gly Thr Val Thr Ile
                        405                 410                 415

Glu Gly Thr Pro Leu Phe Val Asp Lys Glu Asp Gly Leu Thr Ala Val
                    420                 425                 430

Ala Ala Tyr Asp Tyr Gln Gly Arg Thr Val Val Phe Ala Gly Thr Arg
            435                 440                 445

Ser Gly Arg Ile Arg Lys Ile Leu Val Asp Leu Ala Asn Pro Ser Gly
        450                 455                 460

Arg Pro Ala Leu Ala Tyr Glu Ser Val Val Ala Gln Glu Gly Asn Pro
465                     470                 475                 480

Ile Leu Arg Asp Leu Val Leu Ser Pro Asn Arg Gln Tyr Leu Tyr Ala
                    485                 490                 495

Met Thr Glu Lys Gln Val Thr Gln Val Pro Val Glu Ser Cys Val Gln
                500                 505                 510

Tyr Thr Ser Cys Glu Leu Cys Leu Gly Ser Arg Asp Pro His Cys Gly
            515                 520                 525

Trp Cys Val Leu His Ser Ile Cys Ser Arg Gln Asp Ala Cys Glu Arg
        530                 535                 540

Ala Glu Glu Pro Gln Arg Phe Ala Ser Asp Leu Leu Gln Cys Val Gln
545                     550                 555                 560

Leu Thr Val Gln Pro Arg Asn Val Ser Val Thr Met Ser Gln Val Pro
                565                 570                 575

Leu Val Leu Gln Ala Trp Asn Val Pro Asp Leu Ser Ala Gly Val Asn
                580                 585                 590

Cys Ser Phe Glu Asp Phe Thr Glu Thr Glu Ser Ile Leu Glu Asp Gly
            595                 600                 605

Arg Ile His Cys His Ser Pro Ser Ala Arg Glu Val Ala Pro Ile Thr
        610                 615                 620

Gln Gly Gln Gly Asp Gln Arg Val Val Lys Leu Tyr Leu Lys Ser Lys
625                     630                 635                 640

Glu Thr Gly Lys Lys Phe Ala Ser Val Asp Phe Val Phe Tyr Asn Cys
                    645                 650                 655

Ser Val His Gln Ser Cys Leu Ala Cys Val Asn Gly Ser Phe Pro Cys
                660                 665                 670

His Trp Cys Lys Tyr Arg His Val Cys Thr Asn Asn Ala Ala Asp Cys
            675                 680                 685

Ala Phe Leu Glu Gly Arg Val Asn Met Ser Glu Asp Cys Pro Gln Ile
        690                 695                 700

Leu Pro Ser Thr His Ile Tyr Val Pro Val Gly Val Val Lys Pro Ile
705                     710                 715                 720

Thr Leu Ala Ala Arg Asn Leu Pro Gln Pro Gln Ser Gly Gln Arg Gly
                    725                 730                 735
```

```
Tyr Glu Cys Leu Phe His Ile Pro Gly Ser Pro Ala Arg Val Thr Ala
            740                 745                 750

Leu Arg Phe Asn Ser Ser Ser Leu Gln Cys Gln Asn Ser Ser Tyr Ser
            755                 760                 765

Tyr Glu Gly Asn Asp Val Ser Asp Leu Pro Val Asn Leu Ser Val Val
            770                 775                 780

Trp Asn Gly Asn Phe Val Ile Asp Asn Pro Gln Asn Ile Gln Ala His
785                 790                 795                 800

Leu Tyr Lys Cys Pro Ala Leu Arg Gln Ser Cys Gly Leu Cys Leu Lys
            805                 810                 815

Ala Asp Pro Arg Phe Glu Cys Gly Trp Cys Val Ala Glu Arg Arg Cys
            820                 825                 830

Ser Leu Arg His His Cys Pro Ala Asp Ser Pro Ala Ser Trp Met His
            835                 840                 845

Ala His His Gly Ser Ser Arg Cys Thr Asp Pro Lys Ile Leu Lys Leu
            850                 855                 860

Ser Pro Glu Thr Gly Pro Arg Gln Gly Gly Thr Arg Leu Thr Ile Thr
865                 870                 875                 880

Gly Glu Asn Leu Gly Leu Arg Phe Glu Asp Val Arg Leu Gly Val His
            885                 890                 895

Val Gly Lys Val Leu Cys Ser Pro Val Glu Ser Glu Tyr Ile Ser Ala
            900                 905                 910

Glu Gln Ile Val Cys Glu Ile Gly Asp Ala Ser Thr Leu Arg Ala His
            915                 920                 925

Asp Ala Leu Val Glu Val Cys Val Arg Asp Cys Ser Leu His Tyr Arg
            930                 935                 940

Ala Leu Ser Pro Lys Arg Phe Thr Phe Val Thr Pro Thr Phe Tyr Arg
945                 950                 955                 960

Val Ser Pro Ser Arg Gly Pro Leu Ser Gly Gly Thr Trp Ile Gly Ile
            965                 970                 975

Glu Gly Ser His Leu Asn Ala Gly Ser Asp Val Ala Val Ser Ile Gly
            980                 985                 990

Gly Arg Pro Cys Ser Phe Ser Trp Arg Asn Ser Arg Glu Ile Arg Cys
            995                 1000                1005

Leu Thr Pro Pro Gly His Thr Pro Gly Ser Ala Pro Ile Val Ile
            1010                1015                1020

Asn Ile Asn Arg Ala Gln Leu Ser Asn Pro Glu Val Lys Tyr Asn
            1025                1030                1035

Tyr Thr Glu Asp Pro Thr Ile Leu Arg Ile Asp Pro Glu Trp Ser
            1040                1045                1050

Ile Asn Ser Gly Gly Thr Leu Leu Thr Val Thr Gly Thr Asn Leu
            1055                1060                1065

Ala Thr Val Arg Glu Pro Arg Ile Arg Ala Lys Tyr Gly Gly Ile
            1070                1075                1080

Glu Arg Glu Asn Ser Cys Met Val Tyr Asn Asp Thr Thr Met Val
            1085                1090                1095

Cys Arg Ala Pro Ser Ile Asp Asn Pro Lys Arg Ser Pro Pro Glu
            1100                1105                1110

Leu Gly Glu Arg Pro Asp Glu Ile Gly Phe Ile Met Asp Asn Val
            1115                1120                1125

Arg Thr Leu Leu Val Leu Asn Ser Ser Ser Phe Leu Tyr Tyr Pro
            1130                1135                1140
```

```
Asp Pro  Val Leu Glu Pro Leu  Ser Pro Thr Gly Leu  Leu Glu Leu
    1145             1150                 1155

Lys Pro  Ser Ser Pro Leu Ile  Leu Lys Gly Arg Asn  Leu Leu Pro
    1160             1165                 1170

Pro Ala  Pro Gly Asn Ser Arg  Leu Asn Tyr Thr Val  Leu Ile Gly
    1175             1180                 1185

Ser Thr  Pro Cys Ile Leu Thr  Val Ser Glu Thr Gln  Leu Leu Cys
    1190             1195                 1200

Glu Ala  Pro Asn Leu Thr Gly  Gln His Lys Val Thr  Val Arg Ala
    1205             1210                 1215

Gly Gly  Phe Glu Phe Ser Pro  Gly Met Leu Gln Val  Tyr Ser Asp
    1220             1225                 1230

Ser Leu  Leu Thr Leu Pro Ala  Ile Val Gly Ile Gly  Gly Gly Gly
    1235             1240                 1245

Gly Leu  Leu Leu Leu Val Ile  Val Ala Val Leu Ile  Ala Tyr Lys
    1250             1255                 1260

Arg Lys  Ser Arg Asp Ala Asp  Arg Thr Leu Lys Arg  Leu Gln Leu
    1265             1270                 1275

Gln Met  Asp Asn Leu Glu Ser  Arg Val Glu Gln Lys  Leu Ile Ser
    1280             1285                 1290

Glu Glu  Asp Leu
    1295

<210> SEQ ID NO 38
<211> LENGTH: 515
<212> TYPE: PRT
<213> ORGANISM: Artificial Sequence
<220> FEATURE:
<223> OTHER INFORMATION: Mouse plexin A1 sema domain recombinant protein

<400> SEQUENCE: 38

Met Trp Trp Arg Leu Trp Trp Leu Leu Leu Leu Leu Leu Leu Trp
1               5                   10                  15

Pro Met Val Trp Ala Ala Ile Ser Ser Pro Ala Gly Leu Gly Pro
            20                  25                  30

Gln Pro Ala Phe Arg Thr Phe Val Ala Ser Asp Trp Gly Leu Thr His
            35                  40                  45

Leu Val Val His Glu Gln Thr Gly Glu Val Tyr Val Gly Ala Val Asn
 50                  55                  60

Arg Ile Tyr Lys Leu Ser Gly Asn Leu Thr Leu Leu Arg Ala His Val
65                  70                  75                  80

Thr Gly Pro Val Glu Asp Asn Glu Lys Cys Tyr Pro Pro Pro Ser Val
                85                  90                  95

Gln Ser Cys Pro His Gly Leu Gly Ser Thr Asp Asn Val Asn Lys Leu
            100                 105                 110

Leu Leu Leu Asp Tyr Ala Ala Asn Arg Leu Leu Ala Cys Gly Ser Ala
            115                 120                 125

Ser Gln Gly Ile Cys Gln Phe Leu Arg Leu Asp Asp Leu Phe Lys Leu
        130                 135                 140

Gly Glu Pro His His Arg Lys Glu His Tyr Leu Ser Ser Val Arg Glu
145                 150                 155                 160

Ala Gly Ser Met Ala Gly Val Leu Ile Ala Gly Pro Pro Gly Gln Gly
                165                 170                 175

Gln Ala Lys Leu Phe Val Gly Thr Pro Ile Asp Gly Lys Ser Glu Tyr
            180                 185                 190
```

```
Phe Pro Thr Leu Ser Ser Arg Arg Leu Met Ala Asn Glu Glu Asp Ala
            195                 200                 205

Asp Met Phe Gly Phe Val Tyr Gln Asp Glu Phe Val Ser Ser Gln Leu
    210                 215                 220

Lys Ile Pro Ser Asp Thr Leu Ser Lys Phe Pro Ala Phe Asp Ile Tyr
225                 230                 235                 240

Tyr Val Tyr Ser Phe Arg Ser Glu Gln Phe Val Tyr Leu Thr Leu
                245                 250                 255

Gln Leu Asp Thr Gln Leu Thr Ser Pro Asp Ala Ala Gly Glu His Phe
                260                 265                 270

Phe Thr Ser Lys Ile Val Arg Leu Cys Val Asn Asp Pro Lys Phe Tyr
                275                 280                 285

Ser Tyr Val Glu Phe Pro Ile Gly Cys Glu Gln Ala Gly Val Glu Tyr
            290                 295                 300

Arg Leu Val Gln Asp Ala Tyr Leu Ser Arg Pro Gly Gln Ala Leu Ala
305                 310                 315                 320

Lys Gln Leu Gly Leu Ala Glu Asp Glu Val Leu Phe Thr Val Phe
                325                 330                 335

Ala Gln Gly Gln Lys Asn Arg Val Lys Pro Pro Lys Glu Ser Ala Leu
            340                 345                 350

Cys Leu Phe Thr Leu Arg Ala Ile Lys Glu Lys Ile Lys Glu Arg Ile
            355                 360                 365

Gln Ser Cys Tyr Arg Gly Glu Gly Lys Leu Ser Leu Pro Trp Leu Leu
        370                 375                 380

Asn Lys Glu Leu Gly Cys Ile Asn Ser Pro Leu Gln Ile Asp Asp
385                 390                 395                 400

Phe Cys Gly Gln Asp Phe Asn Gln Pro Leu Gly Gly Thr Val Thr Ile
                405                 410                 415

Glu Gly Thr Pro Leu Phe Val Asp Lys Glu Asp Gly Leu Thr Ala Val
            420                 425                 430

Ala Ala Tyr Asp Tyr Gln Gly Arg Thr Val Val Phe Ala Gly Thr Arg
        435                 440                 445

Ser Gly Arg Ile Arg Lys Ile Arg Ala Asp Gly Pro Pro His Gly Gly
450                 455                 460

Val Gln Tyr Glu Met Val Ser Val Phe Lys Asp Gly Ser Pro Ile Leu
465                 470                 475                 480

Arg Asp Met Ala Phe Ser Ile Asn Gln Leu Tyr Leu Tyr Val Met Ser
                485                 490                 495

Glu Arg Gln Val Thr Arg Val Pro Val Glu Ser Asp Tyr Lys Asp Asp
            500                 505                 510

Asp Asp Lys
        515

<210> SEQ ID NO 39
<211> LENGTH: 508
<212> TYPE: PRT
<213> ORGANISM: Artificial Sequence
<220> FEATURE:
<223> OTHER INFORMATION: Mouse plexin A2 sema domain recombinant protein

<400> SEQUENCE: 39

Met Trp Trp Arg Leu Trp Trp Leu Leu Leu Leu Leu Leu Leu Trp
1               5                   10                  15

Pro Met Val Trp Ala Thr Thr Gly Met Pro Gln Tyr Ser Thr Phe His
                20                  25                  30
```

```
Ser Glu Asn Arg Asp Trp Thr Phe Asn His Leu Thr Val His Arg Arg
         35                  40                  45

Thr Gly Ala Val Tyr Val Gly Ala Ile Asn Arg Val Tyr Lys Leu Thr
 50                  55                  60

Gly Asn Leu Thr Ile Gln Val Ala His Lys Thr Gly Pro Glu Glu Asp
 65                  70                  75                  80

Asn Lys Ala Cys Tyr Pro Pro Leu Ile Val Gln Pro Cys Ser Glu Val
                 85                  90                  95

Leu Thr Leu Thr Asn Asn Val Asn Lys Leu Leu Ile Ile Asp Tyr Ser
                100                 105                 110

Glu Asn Arg Leu Leu Ala Cys Gly Ser Leu Tyr Gln Gly Val Cys Lys
            115                 120                 125

Leu Leu Arg Leu Asp Asp Leu Phe Ile Leu Val Glu Pro Ser His Lys
    130                 135                 140

Lys Glu His Tyr Leu Ser Ser Val Asn Lys Thr Gly Thr Met Tyr Gly
145                 150                 155                 160

Val Ile Val Arg Ser Glu Gly Glu Asp Gly Lys Leu Phe Ile Gly Thr
                165                 170                 175

Ala Val Asp Gly Lys Gln Asp Tyr Phe Pro Thr Leu Ser Ser Arg Lys
                180                 185                 190

Leu Pro Arg Asp Pro Glu Ser Ser Ala Met Leu Asp Tyr Glu Leu His
    195                 200                 205

Ser Asp Phe Val Ser Ser Leu Ile Lys Ile Pro Ser Asp Thr Leu Ala
210                 215                 220

Leu Val Ser His Phe Asp Ile Phe Tyr Ile Tyr Gly Phe Ala Ser Gly
225                 230                 235                 240

Gly Phe Val Tyr Phe Leu Thr Val Gln Pro Glu Thr Pro Asp Gly Met
                245                 250                 255

Ala Ile Asn Ser Ala Gly Asp Leu Phe Tyr Thr Ser Arg Ile Val Arg
                260                 265                 270

Leu Cys Lys Asp Asp Pro Lys Phe His Ser Tyr Val Ser Leu Pro Phe
    275                 280                 285

Gly Cys Thr Arg Ala Gly Val Glu Tyr Arg Leu Leu Gln Ala Ala Tyr
290                 295                 300

Leu Ala Lys Pro Gly Glu Ala Leu Ala Gln Ala Phe Asn Ile Ser Ser
305                 310                 315                 320

Asp Glu Asp Val Leu Phe Ala Ile Phe Ser Lys Gly Gln Lys Gln Tyr
                325                 330                 335

His His Pro Pro Asp Asp Ser Ala Leu Cys Ala Phe Pro Ile Arg Ala
            340                 345                 350

Ile Asn Leu Gln Ile Lys Glu Arg Leu Gln Ser Cys Tyr His Gly Glu
        355                 360                 365

Gly Asn Leu Glu Leu Asn Trp Leu Leu Gly Lys Asp Val Gln Cys Thr
    370                 375                 380

Lys Ala Pro Val Pro Ile Asp Asp Asn Phe Cys Gly Leu Asp Ile Asn
385                 390                 395                 400

Gln Pro Leu Gly Gly Ser Thr Pro Val Glu Gly Leu Thr Leu Tyr Thr
                405                 410                 415

Thr Ser Arg Asp Arg Leu Thr Ser Val Ala Ser Tyr Val Tyr Asn Gly
                420                 425                 430

Tyr Ser Val Val Phe Val Gly Thr Lys Ser Gly Lys Leu Lys Lys Ile
                435                 440                 445

Arg Ala Asp Gly Pro Pro His Gly Gly Val Gln Tyr Glu Met Val Ser
```

```
                450                 455                 460
Val Phe Lys Asp Gly Ser Pro Ile Leu Arg Asp Met Ala Phe Ser Ile
465                 470                 475                 480

Asn Gln Leu Tyr Leu Tyr Val Met Ser Glu Arg Gln Val Thr Arg Val
                485                 490                 495

Pro Val Glu Ser Asp Tyr Lys Asp Asp Asp Lys
            500                 505
```

<210> SEQ ID NO 40
<211> LENGTH: 515
<212> TYPE: PRT
<213> ORGANISM: Artificial Sequence
<220> FEATURE:
<223> OTHER INFORMATION: Mouse plexin A1/A2 sema domain chimeric protein

<400> SEQUENCE: 40

```
Met Trp Trp Arg Leu Trp Trp Leu Leu Leu Leu Leu Leu Leu Leu Trp
1               5                   10                  15

Pro Met Val Trp Ala Ala Ile Ser Ser Pro Ala Gly Leu Gly Pro
            20                  25                  30

Gln Pro Ala Phe Arg Thr Phe Val Ala Ser Asp Trp Gly Leu Thr His
                35                  40                  45

Leu Val Val His Glu Gln Thr Gly Glu Val Tyr Val Gly Ala Val Asn
        50                  55                  60

Arg Ile Tyr Lys Leu Ser Gly Asn Leu Thr Leu Leu Arg Ala His Val
65                  70                  75                  80

Thr Gly Pro Val Glu Asp Asn Glu Lys Cys Tyr Pro Pro Pro Ser Val
                85                  90                  95

Gln Ser Cys Pro His Gly Leu Gly Ser Thr Asp Asn Val Asn Lys Leu
            100                 105                 110

Leu Leu Leu Asp Tyr Ala Ala Asn Arg Leu Leu Ala Cys Gly Ser Ala
        115                 120                 125

Ser Gln Gly Ile Cys Gln Phe Leu Arg Leu Asp Asp Leu Phe Lys Leu
    130                 135                 140

Gly Glu Pro His His Arg Lys Glu His Tyr Leu Ser Ser Val Arg Glu
145                 150                 155                 160

Ala Gly Ser Met Ala Gly Val Leu Ile Ala Gly Pro Pro Gly Gln Gly
                165                 170                 175

Gln Ala Lys Leu Phe Val Gly Thr Pro Ile Asp Gly Lys Ser Glu Tyr
            180                 185                 190

Phe Pro Thr Leu Ser Ser Arg Arg Leu Met Ala Asn Glu Glu Asp Ala
        195                 200                 205

Asp Met Phe Gly Phe Val Tyr Gln Asp Glu Phe Val Ser Ser Gln Leu
    210                 215                 220

Lys Ile Pro Ser Asp Thr Leu Ser Lys Phe Pro Ala Phe Asp Ile Tyr
225                 230                 235                 240

Tyr Val Tyr Ser Phe Arg Ser Glu Gln Phe Val Tyr Tyr Leu Thr Leu
                245                 250                 255

Gln Leu Asp Thr Gln Leu Thr Ser Pro Asp Ala Ala Gly Glu His Phe
            260                 265                 270

Phe Thr Ser Lys Ile Val Arg Leu Cys Val Asn Asp Pro Lys Phe Tyr
        275                 280                 285

Ser Tyr Val Glu Phe Pro Ile Gly Cys Glu Gln Ala Gly Val Glu Tyr
    290                 295                 300

Arg Leu Val Gln Asp Ala Tyr Leu Ser Arg Pro Gly Gln Ala Leu Ala
```

```
            305                 310                 315                 320
Lys Gln Leu Gly Leu Ala Glu Asp Glu Val Leu Phe Thr Val Phe
                325                 330                 335

Ala Gln Gly Gln Lys Asn Arg Val Lys Pro Lys Glu Ser Ala Leu
                340                 345                 350

Cys Leu Phe Thr Leu Arg Ala Ile Lys Glu Lys Ile Lys Glu Arg Ile
                355                 360                 365

Gln Ser Cys Tyr Arg Gly Glu Gly Lys Leu Ser Leu Pro Trp Leu Leu
                370                 375                 380

Asn Lys Glu Leu Gly Cys Ile Asn Ser Pro Leu Gln Ile Asp Asp Asp
385                 390                 395                 400

Phe Cys Gly Gln Asp Phe Asn Gln Pro Leu Gly Gly Thr Val Thr Ile
                    405                 410                 415

Glu Gly Thr Pro Leu Phe Val Asp Lys Glu Asp Gly Leu Thr Ala Val
                420                 425                 430

Ala Ala Tyr Asp Tyr Gln Gly Arg Thr Val Val Phe Ala Gly Thr Arg
                435                 440                 445

Ser Gly Arg Ile Arg Lys Ile Arg Ala Asp Gly Pro Pro His Gly Gly
                450                 455                 460

Val Gln Tyr Glu Met Val Ser Val Phe Lys Asp Gly Ser Pro Ile Leu
465                 470                 475                 480

Arg Asp Met Ala Phe Ser Ile Asn Gln Leu Tyr Leu Tyr Val Met Ser
                    485                 490                 495

Glu Arg Gln Val Thr Arg Val Pro Val Glu Ser Asp Tyr Lys Asp Asp
                500                 505                 510

Asp Asp Lys
        515

<210> SEQ ID NO 41
<211> LENGTH: 116
<212> TYPE: PRT
<213> ORGANISM: Oryctolagus cuniculus

<400> SEQUENCE: 41

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Ser Ala
                20                  25                  30

Met Thr Trp Val Arg Gln Ala Pro Gly Lys Gly Leu Glu Trp Ile Gly
            35                  40                  45

Ile Ile Asn Asn Ser Asn Ile Ala Ala Tyr Ala Ser Trp Thr Lys Gly
        50                  55                  60

Arg Phe Thr Ile Ser Lys Thr Ser Thr Thr Val Asp Leu Lys Ile Thr
65                  70                  75                  80

Ser Pro Ile Ile Glu Asp Thr Ala Thr Tyr Phe Cys Ala Arg Gly Asp
                    85                  90                  95

Val Gly Thr Thr His Tyr Phe Asn Ile Trp Gly Pro Gly Thr Leu Val
                100                 105                 110

Thr Val Ser Ser
        115

<210> SEQ ID NO 42
<211> LENGTH: 111
<212> TYPE: PRT
<213> ORGANISM: Oryctolagus cuniculus
```

```
<400> SEQUENCE: 42

Ala Ala Val Leu Thr Gln Thr Pro Ser Pro Val Ser Ala Val Val Gly
1               5                   10                  15

Gly Thr Val Ser Ile Ser Cys Gln Ser Ser Lys Ser Val Tyr Asn Asn
            20                  25                  30

Asn Trp Leu Ser Trp Phe Gln Gln Lys Pro Gly Gln Pro Pro Lys Leu
        35                  40                  45

Leu Ile Tyr Gly Ala Ser Thr Leu Ala Ser Gly Val Pro Ser Arg Phe
    50                  55                  60

Lys Gly Ser Gly Ser Gly Thr Gln Phe Thr Leu Ala Ile Ser Asp Val
65                  70                  75                  80

Gln Cys Asp Asp Ala Ala Thr Tyr Tyr Cys Ala Gly Gly Tyr Ile Asn
                85                  90                  95

Ser Asp Asn Phe Ala Phe Gly Gly Gly Thr Glu Val Val Val Lys
            100                 105                 110

<210> SEQ ID NO 43
<211> LENGTH: 121
<212> TYPE: PRT
<213> ORGANISM: Oryctolagus cuniculus

<400> SEQUENCE: 43

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Ser Gly Gly Phe
            20                  25                  30

Tyr Ile Tyr Trp Val Arg Gln Ala Pro Gly Lys Gly Leu Glu Trp Ile
        35                  40                  45

Ala Cys Ile Gly Thr Gly Ser Ser Gly Asn Thr Asp Tyr Ala Ser Trp
    50                  55                  60

Ala Lys Gly Arg Phe Thr Ile Thr Gly Ser Ala Ser Leu Asn Thr Val
65                  70                  75                  80

Thr Leu Gln Leu Asn Ser Leu Thr Ala Ala Asp Thr Ala Thr Tyr Phe
                85                  90                  95

Cys Ala Arg Gly Pro Phe Gly Ala Gly Ser Tyr Tyr Asn Leu Trp Gly
            100                 105                 110

Pro Gly Thr Leu Val Thr Val Ser Ser
        115                 120

<210> SEQ ID NO 44
<211> LENGTH: 108
<212> TYPE: PRT
<213> ORGANISM: Oryctolagus cuniculus

<400> SEQUENCE: 44

Ala Phe Glu Leu Thr Gln Thr Pro Ala Ser Val Glu Ala Ala Val Gly
1               5                   10                  15

Gly Thr Val Thr Ile Lys Cys Gln Ala Ser Gln Ser Ile Ser Ser Tyr
            20                  25                  30

Phe Ser Trp Tyr Gln Gln Lys Pro Gly Gln Pro Pro Lys Leu Leu Ile
        35                  40                  45

Tyr Gln Ala Ser Lys Leu Ala Ser Gly Val Pro Ser Arg Phe Lys Gly
    50                  55                  60

Ser Gly Ser Gly Thr Glu Val Thr Leu Thr Ile Ser Asp Leu Glu Cys
65                  70                  75                  80

Ala Asp Ala Ala Thr Tyr Tyr Cys Gln Ser Tyr Tyr Gly Val Thr Thr
```

```
                    85                  90                  95
Asn Ile Phe Gly Gly Gly Thr Glu Val Val Lys
                100                 105

<210> SEQ ID NO 45
<211> LENGTH: 446
<212> TYPE: PRT
<213> ORGANISM: Artificial Sequence
<220> FEATURE:
<223> OTHER INFORMATION: H chain of human/mouse chimeric anti-plexin A1
      antibody PXB693

<400> SEQUENCE: 45

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Ser Ala
            20                  25                  30

Met Thr Trp Val Arg Gln Ala Pro Gly Lys Gly Leu Glu Trp Ile Gly
        35                  40                  45

Ile Ile Asn Asn Ser Asn Ile Ala Ala Tyr Ala Ser Trp Thr Lys Gly
    50                  55                  60

Arg Phe Thr Ile Ser Lys Thr Ser Thr Thr Val Asp Leu Lys Ile Thr
65                  70                  75                  80

Ser Pro Ile Ile Glu Asp Thr Ala Thr Tyr Phe Cys Ala Arg Gly Asp
                85                  90                  95

Val Gly Thr Thr His Tyr Phe Asn Ile Trp Gly Pro Gly Thr Leu Val
            100                 105                 110

Thr Val Ser Ser Ala Lys Thr Thr Ala Pro Ser Val Tyr Pro Leu Ala
        115                 120                 125

Pro Val Cys Gly Asp Thr Thr Gly Ser Ser Val Thr Leu Gly Cys Leu
    130                 135                 140

Val Lys Gly Tyr Phe Pro Glu Pro Val Thr Leu Thr Trp Asn Ser Gly
145                 150                 155                 160

Ser Leu Ser Ser Gly Val His Thr Phe Pro Ala Val Leu Gln Ser Asp
                165                 170                 175

Leu Tyr Thr Leu Ser Ser Ser Val Thr Val Thr Ser Ser Thr Trp Pro
            180                 185                 190

Ser Gln Ser Ile Thr Cys Asn Val Ala His Pro Ala Ser Ser Thr Lys
        195                 200                 205

Val Asp Lys Lys Ile Glu Pro Arg Gly Pro Thr Ile Lys Pro Cys Pro
    210                 215                 220

Pro Cys Lys Cys Pro Ala Pro Asn Leu Arg Arg Gly Pro Lys Val Phe
225                 230                 235                 240

Ile Phe Pro Pro Lys Ile Lys Asp Val Leu Met Ile Ser Leu Ser Pro
                245                 250                 255

Ile Val Thr Cys Val Val Val Asp Val Ser Glu Asp Asp Pro Asp Val
            260                 265                 270

Gln Ile Ser Trp Phe Val Asn Asn Val Glu Val His Thr Ala Gln Thr
        275                 280                 285

Gln Thr His Arg Glu Asp Tyr Asn Ser Thr Leu Arg Val Val Ser Ala
    290                 295                 300

Leu Pro Ile Gln His Gln Asp Trp Met Ser Gly Lys Glu Phe Lys Cys
305                 310                 315                 320

Lys Val Asn Asn Lys Asp Leu Pro Ala Pro Ile Glu Arg Thr Ile Ser
                325                 330                 335
```

```
Lys Pro Lys Gly Ser Val Arg Ala Pro Gln Val Tyr Val Leu Pro Pro
                340                 345                 350

Pro Glu Glu Glu Met Thr Lys Lys Gln Val Thr Leu Thr Cys Met Val
            355                 360                 365

Thr Asp Phe Met Pro Glu Asp Ile Tyr Val Glu Trp Thr Asn Asn Gly
        370                 375                 380

Lys Thr Glu Leu Asn Tyr Lys Asn Thr Glu Pro Val Leu Asp Ser Asp
385                 390                 395                 400

Gly Ser Tyr Phe Met Tyr Ser Lys Leu Arg Val Glu Lys Lys Asn Trp
                405                 410                 415

Val Glu Arg Asn Ser Tyr Ser Cys Ser Val Val His Glu Gly Leu His
            420                 425                 430

Asn His His Thr Thr Lys Ser Phe Ser Arg Thr Pro Gly Lys
        435                 440                 445

<210> SEQ ID NO 46
<211> LENGTH: 218
<212> TYPE: PRT
<213> ORGANISM: Artificial Sequence
<220> FEATURE:
<223> OTHER INFORMATION: L chain of human/mouse chimeric anti-plexin A1
      antibody PXB693

<400> SEQUENCE: 46

Ala Ala Val Leu Thr Gln Thr Pro Ser Pro Val Ser Ala Val Val Gly
1               5                   10                  15

Gly Thr Val Ser Ile Ser Cys Gln Ser Ser Lys Ser Val Tyr Asn Asn
                20                  25                  30

Asn Trp Leu Ser Trp Phe Gln Gln Lys Pro Gly Gln Pro Pro Lys Leu
            35                  40                  45

Leu Ile Tyr Gly Ala Ser Thr Leu Ala Ser Gly Val Pro Ser Arg Phe
        50                  55                  60

Lys Gly Ser Gly Ser Gly Thr Gln Phe Thr Leu Ala Ile Ser Asp Val
65                  70                  75                  80

Gln Cys Asp Asp Ala Ala Thr Tyr Tyr Cys Ala Gly Gly Tyr Ile Asn
                85                  90                  95

Ser Asp Asn Phe Ala Phe Gly Gly Gly Thr Glu Val Val Lys Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215

<210> SEQ ID NO 47
<211> LENGTH: 451
<212> TYPE: PRT
<213> ORGANISM: Artificial Sequence
```

<220> FEATURE:
<223> OTHER INFORMATION: H chain of human/mouse chimeric anti-plexin A1
      antibody PXB727

<400> SEQUENCE: 47

```
Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Ser Gly Gly Phe
            20                  25                  30

Tyr Ile Tyr Trp Val Arg Gln Ala Pro Gly Lys Gly Leu Glu Trp Ile
        35                  40                  45

Ala Cys Ile Gly Thr Gly Ser Ser Gly Asn Thr Asp Tyr Ala Ser Trp
    50                  55                  60

Ala Lys Gly Arg Phe Thr Ile Thr Gly Ser Ala Ser Leu Asn Thr Val
65                  70                  75                  80

Thr Leu Gln Leu Asn Ser Leu Thr Ala Ala Asp Thr Ala Thr Tyr Phe
                85                  90                  95

Cys Ala Arg Gly Pro Phe Gly Ala Gly Ser Tyr Tyr Asn Leu Trp Gly
            100                 105                 110

Pro Gly Thr Leu Val Thr Val Ser Ser Ala Lys Thr Thr Ala Pro Ser
        115                 120                 125

Val Tyr Pro Leu Ala Pro Val Cys Gly Asp Thr Thr Gly Ser Ser Val
    130                 135                 140

Thr Leu Gly Cys Leu Val Lys Gly Tyr Phe Pro Glu Pro Val Thr Leu
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Thr
            180                 185                 190

Ser Ser Thr Trp Pro Ser Gln Ser Ile Thr Cys Asn Val Ala His Pro
        195                 200                 205

Ala Ser Ser Thr Lys Val Asp Lys Lys Ile Glu Pro Arg Gly Pro Thr
    210                 215                 220

Ile Lys Pro Cys Pro Pro Cys Lys Cys Pro Ala Pro Asn Leu Arg Arg
225                 230                 235                 240

Gly Pro Lys Val Phe Ile Phe Pro Pro Lys Ile Lys Asp Val Leu Met
                245                 250                 255

Ile Ser Leu Ser Pro Ile Val Thr Cys Val Val Asp Val Ser Glu
            260                 265                 270

Asp Asp Pro Asp Val Gln Ile Ser Trp Phe Val Asn Asn Val Glu Val
        275                 280                 285

His Thr Ala Gln Thr Gln Thr His Arg Glu Asp Tyr Asn Ser Thr Leu
    290                 295                 300

Arg Val Val Ser Ala Leu Pro Ile Gln His Gln Asp Trp Met Ser Gly
305                 310                 315                 320

Lys Glu Phe Lys Cys Lys Val Asn Asn Lys Asp Leu Pro Ala Pro Ile
                325                 330                 335

Glu Arg Thr Ile Ser Lys Pro Lys Gly Ser Val Arg Ala Pro Gln Val
            340                 345                 350

Tyr Val Leu Pro Pro Pro Glu Glu Met Thr Lys Lys Gln Val Thr
        355                 360                 365

Leu Thr Cys Met Val Thr Asp Phe Met Pro Glu Asp Ile Tyr Val Glu
    370                 375                 380

Trp Thr Asn Asn Gly Lys Thr Glu Leu Asn Tyr Lys Asn Thr Glu Pro
```

```
                385                 390                 395                 400
Val Leu Asp Ser Asp Gly Ser Tyr Phe Met Tyr Ser Lys Leu Arg Val
                405                 410                 415

Glu Lys Lys Asn Trp Val Glu Arg Asn Ser Tyr Ser Cys Ser Val Val
                420                 425                 430

His Glu Gly Leu His Asn His Thr Thr Lys Ser Phe Ser Arg Thr
                435                 440                 445

Pro Gly Lys
    450

<210> SEQ ID NO 48
<211> LENGTH: 215
<212> TYPE: PRT
<213> ORGANISM: Artificial Sequence
<220> FEATURE:
<223> OTHER INFORMATION: L chain of human/mouse chimeric anti-plexin A1
      antibody PXB727

<400> SEQUENCE: 48

Ala Phe Glu Leu Thr Gln Thr Pro Ala Ser Val Glu Ala Ala Val Gly
1               5                   10                  15

Gly Thr Val Thr Ile Lys Cys Gln Ala Ser Gln Ser Ile Ser Ser Tyr
                20                  25                  30

Phe Ser Trp Tyr Gln Gln Lys Pro Gly Gln Pro Pro Lys Leu Leu Ile
            35                  40                  45

Tyr Gln Ala Ser Lys Leu Ala Ser Gly Val Pro Ser Arg Phe Lys Gly
    50                  55                  60

Ser Gly Ser Gly Thr Glu Val Thr Leu Thr Ile Ser Asp Leu Glu Cys
65                  70                  75                  80

Ala Asp Ala Ala Thr Tyr Tyr Cys Gln Ser Tyr Tyr Gly Val Thr Thr
                85                  90                  95

Asn Ile Phe Gly Gly Gly Thr Glu Val Val Val Lys Arg Ala Asp Ala
                100                 105                 110

Ala Pro Thr Val Ser Ile Phe Pro Pro Ser Ser Glu Gln Leu Thr Ser
            115                 120                 125

Gly Gly Ala Ser Val Val Cys Phe Leu Asn Asn Phe Tyr Pro Lys Asp
    130                 135                 140

Ile Asn Val Lys Trp Lys Ile Asp Gly Ser Glu Arg Gln Asn Gly Val
145                 150                 155                 160

Leu Asn Ser Trp Thr Asp Gln Asp Ser Lys Asp Ser Thr Tyr Ser Met
                165                 170                 175

Ser Ser Thr Leu Thr Leu Thr Lys Asp Glu Tyr Glu Arg His Asn Ser
            180                 185                 190

Tyr Thr Cys Glu Ala Thr His Lys Thr Ser Thr Ser Pro Ile Val Lys
    195                 200                 205

Ser Phe Asn Arg Asn Glu Cys
210                 215

<210> SEQ ID NO 49
<211> LENGTH: 448
<212> TYPE: PRT
<213> ORGANISM: Artificial Sequence
<220> FEATURE:
<223> OTHER INFORMATION: H chain of human/mouse chimeric anti-plexin A1
      antibody PXB361b

<400> SEQUENCE: 49

Gln Ser Leu Glu Glu Ser Gly Gly Asp Leu Val Lys Pro Glu Gly Ser
```

-continued

```
1               5                   10                  15
Leu Thr Leu Ser Cys Thr Ala Ser Gly Phe Thr Ile Ser Ser Ser Tyr
                20                  25                  30
Trp Ile Cys Trp Val Arg Gln Ala Pro Gly Lys Gly Leu Glu Trp Ile
                35                  40                  45
Ala Cys Ile Tyr Val Gly Ser Gly Asp Gly Tyr Thr Tyr Tyr Ala Ser
                50                  55                  60
Trp Ala Lys Gly Arg Phe Thr Ile Ser Lys Thr Ser Ser Thr Thr Val
65                  70                  75                  80
Thr Leu Arg Met Thr Ser Leu Thr Ala Ala Asp Thr Ala Thr Tyr Phe
                85                  90                  95
Cys Ala Arg Gly Gly Asp Gly Val Gly Gly Phe Asp Phe Phe Asp
                100                 105                 110
Pro Trp Gly Pro Gly Thr Leu Val Thr Val Ser Ser Ala Lys Thr Thr
                115                 120                 125
Pro Pro Ser Val Tyr Pro Leu Ala Pro Gly Ser Ala Ala Gln Thr Asn
                130                 135                 140
Ser Met Val Thr Leu Gly Cys Leu Val Lys Gly Tyr Phe Pro Glu Pro
145                 150                 155                 160
Val Thr Val Thr Trp Asn Ser Gly Ser Leu Ser Ser Gly Val His Thr
                165                 170                 175
Phe Pro Ala Val Leu Gln Ser Asp Leu Tyr Thr Leu Ser Ser Ser Val
                180                 185                 190
Thr Val Pro Ser Ser Thr Trp Pro Ser Glu Thr Val Thr Cys Asn Val
                195                 200                 205
Ala His Pro Ala Ser Ser Thr Lys Val Asp Lys Lys Ile Val Pro Arg
                210                 215                 220
Asp Cys Gly Cys Lys Pro Cys Ile Cys Thr Val Lys Glu Val Ser Lys
225                 230                 235                 240
Val Phe Ile Phe Pro Pro Lys Pro Lys Asp Val Leu Thr Ile Thr Leu
                245                 250                 255
Thr Pro Lys Val Thr Cys Val Val Asp Ile Ser Lys Asp Asp Pro
                260                 265                 270
Glu Val Gln Phe Ser Trp Phe Val Asp Asp Val Glu Val His Thr Ala
                275                 280                 285
Gln Thr Gln Pro Arg Glu Glu Gln Phe Asn Ser Thr Phe Arg Ser Val
                290                 295                 300
Ser Glu Leu Pro Ile Met His Gln Asp Trp Leu Asn Gly Lys Glu Phe
305                 310                 315                 320
Lys Cys Arg Val Asn Ser Ala Ala Phe Pro Ala Pro Ile Glu Lys Thr
                325                 330                 335
Ile Ser Lys Thr Lys Gly Arg Pro Lys Ala Pro Gln Val Tyr Thr Ile
                340                 345                 350
Pro Pro Pro Lys Glu Gln Met Ala Lys Asp Lys Val Ser Leu Thr Cys
                355                 360                 365
Met Ile Thr Asp Phe Phe Pro Glu Asp Ile Thr Val Glu Trp Gln Trp
                370                 375                 380
Asn Gly Gln Pro Ala Glu Asn Tyr Lys Asn Thr Gln Pro Ile Met Asp
385                 390                 395                 400
Thr Asp Gly Ser Tyr Phe Val Tyr Ser Lys Leu Asn Val Gln Lys Ser
                405                 410                 415
Asn Trp Glu Ala Gly Asn Thr Phe Thr Cys Ser Val Leu His Glu Gly
                420                 425                 430
```

Leu His Asn His His Thr Glu Lys Ser Leu Ser His Ser Pro Gly Lys
            435                 440                 445

<210> SEQ ID NO 50
<211> LENGTH: 216
<212> TYPE: PRT
<213> ORGANISM: Artificial Sequence
<220> FEATURE:
<223> OTHER INFORMATION: L chain of human/mouse chimeric anti-plexin A1
      antibody PXB361b

<400> SEQUENCE: 50

Asp Val Val Leu Thr Gln Thr Pro Ala Ser Val Ser Glu Pro Val Gly
1               5                   10                  15

Gly Thr Val Thr Ile Lys Cys Gln Ala Thr Glu Ser Ile Asn Arg Asn
            20                  25                  30

Cys Ala Trp Tyr Gln Gln Lys Pro Gly Gln Pro Pro Lys Leu Leu Ile
        35                  40                  45

Tyr Arg Ala Ser Thr Leu Ala Ser Gly Val Pro Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Cys Thr Asp Tyr Gly Thr Tyr
                85                  90                  95

Tyr Val Ala Phe Gly Gly Gly Thr Glu Val Val Val Lys Arg Ala Asp
            100                 105                 110

Ala Ala Pro Thr Val Ser Ile Phe Pro Pro Ser Ser Glu Gln Leu Thr
        115                 120                 125

Ser Gly Gly Ala Ser Val Val Cys Phe Leu Asn Asn Phe Tyr Pro Lys
130                 135                 140

Asp Ile Asn Val Lys Trp Lys Ile Asp Gly Ser Glu Arg Gln Asn Gly
145                 150                 155                 160

Val Leu Asn Ser Trp Thr Asp Gln Asp Ser Lys Asp Ser Thr Tyr Ser
                165                 170                 175

Met Ser Ser Thr Leu Thr Leu Thr Lys Asp Glu Tyr Glu Arg His Asn
            180                 185                 190

Ser Tyr Thr Cys Glu Ala Thr His Lys Thr Ser Thr Ser Pro Ile Val
        195                 200                 205

Lys Ser Phe Asn Arg Asn Glu Cys
    210                 215

<210> SEQ ID NO 51
<211> LENGTH: 10
<212> TYPE: PRT
<213> ORGANISM: Artificial Sequence
<220> FEATURE:
<223> OTHER INFORMATION: Myc tag sequence

<400> SEQUENCE: 51

Glu Gln Lys Leu Ile Ser Glu Glu Asp Leu
1               5                   10

<210> SEQ ID NO 52
<211> LENGTH: 1894
<212> TYPE: PRT
<213> ORGANISM: Mus musculus

<400> SEQUENCE: 52

Met Pro Leu Pro Pro Leu Ser Ser Arg Thr Leu Leu Leu Leu Leu Leu

-continued

```
1               5                   10                  15
Leu Leu Leu Arg Gly Val Trp Ile Ala Ile Ser Ser Pro Pro Ala Gly
                20                  25                  30
Leu Gly Pro Gln Pro Ala Phe Arg Thr Phe Val Ala Ser Asp Trp Gly
                35                  40                  45
Leu Thr His Leu Val Val His Glu Gln Thr Gly Glu Val Tyr Val Gly
    50                  55                  60
Ala Val Asn Arg Ile Tyr Lys Leu Ser Gly Asn Leu Thr Leu Leu Arg
65                  70                  75                  80
Ala His Val Thr Gly Pro Val Glu Asp Asn Glu Lys Cys Tyr Pro Pro
                85                  90                  95
Pro Ser Val Gln Ser Cys Pro His Gly Leu Gly Ser Thr Asp Asn Val
                100                 105                 110
Asn Lys Leu Leu Leu Leu Asp Tyr Ala Ala Asn Arg Leu Leu Ala Cys
                115                 120                 125
Gly Ser Ala Ser Gln Gly Ile Cys Gln Phe Leu Arg Leu Asp Asp Leu
                130                 135                 140
Phe Lys Leu Gly Glu Pro His His Arg Lys Glu His Tyr Leu Ser Ser
145                 150                 155                 160
Val Arg Glu Ala Gly Ser Met Ala Gly Val Leu Ile Ala Gly Pro Pro
                165                 170                 175
Gly Gln Gly Gln Ala Lys Leu Phe Val Gly Thr Pro Ile Asp Gly Lys
                180                 185                 190
Ser Glu Tyr Phe Pro Thr Leu Ser Ser Arg Arg Leu Met Ala Asn Glu
                195                 200                 205
Glu Asp Ala Asp Met Phe Gly Phe Val Tyr Gln Asp Glu Phe Val Ser
                210                 215                 220
Ser Gln Leu Lys Ile Pro Ser Asp Thr Leu Ser Lys Phe Pro Ala Phe
225                 230                 235                 240
Asp Ile Tyr Tyr Val Tyr Ser Phe Arg Ser Glu Gln Phe Val Tyr Tyr
                245                 250                 255
Leu Thr Leu Gln Leu Asp Thr Gln Leu Thr Ser Pro Asp Ala Ala Gly
                260                 265                 270
Glu His Phe Phe Thr Ser Lys Ile Val Arg Leu Cys Val Asn Asp Pro
                275                 280                 285
Lys Phe Tyr Ser Tyr Val Glu Phe Pro Ile Gly Cys Glu Gln Ala Gly
                290                 295                 300
Val Glu Tyr Arg Leu Val Gln Asp Ala Tyr Leu Ser Arg Pro Gly Gln
305                 310                 315                 320
Ala Leu Ala Lys Gln Leu Gly Leu Ala Glu Asp Glu Val Leu Phe
                325                 330                 335
Thr Val Phe Ala Gln Gly Gln Lys Asn Arg Val Lys Pro Pro Lys Glu
                340                 345                 350
Ser Ala Leu Cys Leu Phe Thr Leu Arg Ala Ile Lys Glu Lys Ile Lys
                355                 360                 365
Glu Arg Ile Gln Ser Cys Tyr Arg Gly Glu Gly Lys Leu Ser Leu Pro
                370                 375                 380
Trp Leu Leu Asn Lys Glu Leu Gly Cys Ile Asn Ser Pro Leu Gln Ile
385                 390                 395                 400
Asp Asp Asp Phe Cys Gly Gln Asp Phe Asn Gln Pro Leu Gly Gly Thr
                405                 410                 415
Val Thr Ile Glu Gly Thr Pro Leu Phe Val Asp Lys Glu Asp Gly Leu
                420                 425                 430
```

```
Thr Ala Val Ala Ala Tyr Asp Tyr Gln Gly Arg Thr Val Phe Ala
            435                 440                 445

Gly Thr Arg Ser Gly Arg Ile Arg Lys Ile Leu Val Asp Leu Ala Asn
    450                 455                 460

Pro Ser Gly Arg Pro Ala Leu Ala Tyr Glu Ser Val Val Ala Gln Glu
465                 470                 475                 480

Gly Asn Pro Ile Leu Arg Asp Leu Val Leu Ser Pro Asn Arg Gln Tyr
                485                 490                 495

Leu Tyr Ala Met Thr Glu Lys Gln Val Thr Gln Val Pro Val Glu Ser
            500                 505                 510

Cys Val Gln Tyr Thr Ser Cys Glu Leu Cys Leu Gly Ser Arg Asp Pro
            515                 520                 525

His Cys Gly Trp Cys Val Leu His Ser Ile Cys Ser Arg Gln Asp Ala
            530                 535                 540

Cys Glu Arg Ala Glu Glu Pro Gln Arg Phe Ala Ser Asp Leu Leu Gln
545                 550                 555                 560

Cys Val Gln Leu Thr Val Gln Pro Arg Asn Val Ser Val Thr Met Ser
                565                 570                 575

Gln Val Pro Leu Val Leu Gln Ala Trp Asn Val Pro Asp Leu Ser Ala
            580                 585                 590

Gly Val Asn Cys Ser Phe Glu Asp Phe Thr Glu Thr Glu Ser Ile Leu
            595                 600                 605

Glu Asp Gly Arg Ile His Cys His Ser Pro Ser Ala Arg Glu Val Ala
610                 615                 620

Pro Ile Thr Gln Gly Gln Gly Asp Gln Arg Val Val Lys Leu Tyr Leu
625                 630                 635                 640

Lys Ser Lys Glu Thr Gly Lys Lys Phe Ala Ser Val Asp Phe Val Phe
                645                 650                 655

Tyr Asn Cys Ser Val His Gln Ser Cys Leu Ala Cys Val Asn Gly Ser
            660                 665                 670

Phe Pro Cys His Trp Cys Lys Tyr Arg His Val Cys Thr Asn Asn Ala
            675                 680                 685

Ala Asp Cys Ala Phe Leu Glu Gly Arg Val Asn Met Ser Glu Asp Cys
            690                 695                 700

Pro Gln Ile Leu Pro Ser Thr His Ile Tyr Val Pro Val Gly Val Val
705                 710                 715                 720

Lys Pro Ile Thr Leu Ala Ala Arg Asn Leu Pro Gln Pro Gln Ser Gly
                725                 730                 735

Gln Arg Gly Tyr Glu Cys Leu Phe His Ile Pro Gly Ser Pro Ala Arg
            740                 745                 750

Val Thr Ala Leu Arg Phe Asn Ser Ser Ser Leu Gln Cys Gln Asn Ser
            755                 760                 765

Ser Tyr Ser Tyr Glu Gly Asn Asp Val Ser Asp Leu Pro Val Asn Leu
            770                 775                 780

Ser Val Val Trp Asn Gly Asn Phe Val Ile Asp Asn Pro Gln Asn Ile
785                 790                 795                 800

Gln Ala His Leu Tyr Lys Cys Pro Ala Leu Arg Gln Ser Cys Gly Leu
            805                 810                 815

Cys Leu Lys Ala Asp Pro Arg Phe Glu Cys Gly Trp Cys Val Ala Glu
            820                 825                 830

Arg Arg Cys Ser Leu Arg His His Cys Pro Ala Asp Ser Pro Ala Ser
            835                 840                 845
```

```
Trp Met His Ala His His Gly Ser Ser Arg Cys Thr Asp Pro Lys Ile
850                 855                 860

Leu Lys Leu Ser Pro Glu Thr Gly Pro Arg Gln Gly Gly Thr Arg Leu
865                 870                 875                 880

Thr Ile Thr Gly Glu Asn Leu Gly Leu Arg Phe Glu Asp Val Arg Leu
            885                 890                 895

Gly Val His Val Gly Lys Val Leu Cys Ser Pro Val Glu Ser Glu Tyr
            900                 905                 910

Ile Ser Ala Glu Gln Ile Val Cys Glu Ile Gly Asp Ala Ser Thr Leu
            915                 920                 925

Arg Ala His Asp Ala Leu Val Glu Val Cys Val Arg Asp Cys Ser Leu
930                 935                 940

His Tyr Arg Ala Leu Ser Pro Lys Arg Phe Thr Phe Val Pro Thr
945                 950                 955                 960

Phe Tyr Arg Val Ser Pro Ser Arg Gly Pro Leu Ser Gly Gly Thr Trp
                965                 970                 975

Ile Gly Ile Glu Gly Ser His Leu Asn Ala Gly Ser Asp Val Ala Val
            980                 985                 990

Ser Ile Gly Gly Arg Pro Cys Ser  Phe Ser Trp Arg Asn  Ser Arg Glu
            995                 1000                 1005

Ile Arg Cys Leu Thr Pro Pro  Gly His Thr Pro Gly  Ser Ala Pro
1010                 1015                 1020

Ile Val Ile Asn Ile Asn Arg  Ala Gln Leu Ser Asn  Pro Glu Val
1025                 1030                 1035

Lys Tyr Asn Tyr Thr Glu Asp  Pro Thr Ile Leu Arg  Ile Asp Pro
1040                 1045                 1050

Glu Trp Ser Ile Asn Ser Gly  Gly Thr Leu Leu Thr  Val Thr Gly
1055                 1060                 1065

Thr Asn Leu Ala Thr Val Arg  Glu Pro Arg Ile Arg  Ala Lys Tyr
1070                 1075                 1080

Gly Gly Ile Glu Arg Glu Asn  Ser Cys Met Val Tyr  Asn Asp Thr
1085                 1090                 1095

Thr Met Val Cys Arg Ala Pro  Ser Ile Asp Asn Pro  Lys Arg Ser
1100                 1105                 1110

Pro Pro Glu Leu Gly Glu Arg  Pro Asp Glu Ile Gly  Phe Ile Met
1115                 1120                 1125

Asp Asn Val Arg Thr Leu Leu  Val Leu Asn Ser Ser  Ser Phe Leu
1130                 1135                 1140

Tyr Tyr Pro Asp Pro Val Leu  Glu Pro Leu Ser Pro  Thr Gly Leu
1145                 1150                 1155

Leu Glu Leu Lys Pro Ser Ser  Pro Leu Ile Leu Lys  Gly Arg Asn
1160                 1165                 1170

Leu Leu Pro Pro Ala Pro Gly  Asn Ser Arg Leu Asn  Tyr Thr Val
1175                 1180                 1185

Leu Ile Gly Ser Thr Pro Cys  Ile Leu Thr Val Ser  Glu Thr Gln
1190                 1195                 1200

Leu Leu Cys Glu Ala Pro Asn  Leu Thr Gly Gln His  Lys Val Thr
1205                 1210                 1215

Val Arg Ala Gly Gly Phe Glu  Phe Ser Pro Gly Met  Leu Gln Val
1220                 1225                 1230

Tyr Ser Asp Ser Leu Leu Thr  Leu Pro Ala Ile Val  Gly Ile Gly
1235                 1240                 1245

Gly Gly Gly Gly Leu Leu Leu  Leu Val Ile Val Ala  Val Leu Ile
```

```
                1250                1255                1260

Ala Tyr Lys Arg Lys Ser Arg Asp Ala Asp Arg Thr Leu Lys Arg
    1265                1270                1275

Leu Gln Leu Gln Met Asp Asn Leu Glu Ser Arg Val Ala Leu Glu
    1280                1285                1290

Cys Lys Glu Ala Phe Ala Glu Leu Gln Thr Asp Ile His Glu Leu
    1295                1300                1305

Thr Ser Asp Leu Asp Gly Ala Gly Ile Pro Phe Leu Asp Tyr Arg
    1310                1315                1320

Thr Tyr Ala Met Arg Val Leu Phe Pro Gly Ile Glu Asp His Pro
    1325                1330                1335

Val Leu Lys Glu Met Glu Val Gln Ala Asn Val Glu Lys Ser Leu
    1340                1345                1350

Thr Leu Phe Gly Gln Leu Leu Thr Lys Lys His Phe Leu Leu Thr
    1355                1360                1365

Phe Ile Arg Thr Leu Glu Ala Gln Arg Ser Phe Ser Met Arg Asp
    1370                1375                1380

Arg Gly Asn Val Ala Ser Leu Ile Met Thr Ala Leu Gln Gly Glu
    1385                1390                1395

Met Glu Tyr Ala Thr Gly Val Leu Lys Gln Leu Leu Ser Asp Leu
    1400                1405                1410

Ile Glu Lys Asn Leu Glu Ser Lys Asn His Pro Lys Leu Leu Leu
    1415                1420                1425

Arg Arg Thr Glu Ser Val Ala Glu Lys Met Leu Thr Asn Trp Phe
    1430                1435                1440

Thr Phe Leu Leu Tyr Lys Phe Leu Lys Glu Cys Ala Gly Glu Pro
    1445                1450                1455

Leu Phe Met Leu Tyr Cys Ala Ile Lys Gln Gln Met Glu Lys Gly
    1460                1465                1470

Pro Ile Asp Ala Ile Thr Gly Glu Ala Arg Tyr Ser Leu Ser Glu
    1475                1480                1485

Asp Lys Leu Ile Arg Gln Gln Ile Asp Tyr Lys Thr Leu Thr Leu
    1490                1495                1500

Asn Cys Val Asn Pro Glu His Glu Asn Ala Pro Glu Val Pro Val
    1505                1510                1515

Lys Gly Leu Asn Cys Asp Thr Val Thr Gln Val Lys Glu Lys Leu
    1520                1525                1530

Leu Asp Ala Val Tyr Lys Gly Val Pro Tyr Ser Gln Arg Pro Lys
    1535                1540                1545

Ala Gly Asp Met Asp Leu Glu Trp Arg Gln Gly Arg Met Ala Arg
    1550                1555                1560

Ile Ile Leu Gln Asp Glu Asp Val Thr Thr Lys Ile Asp Asn Asp
    1565                1570                1575

Trp Lys Arg Leu Asn Thr Leu Ala His Tyr Gln Val Thr Asp Gly
    1580                1585                1590

Ser Ser Val Ala Leu Val Pro Lys Gln Thr Ser Ala Tyr Asn Ile
    1595                1600                1605

Ser Asn Ser Ser Thr Phe Thr Lys Ser Leu Ser Arg Tyr Glu Ser
    1610                1615                1620

Met Leu Arg Thr Ala Ser Ser Pro Asp Ser Leu Arg Ser Arg Thr
    1625                1630                1635

Pro Met Ile Thr Pro Asp Leu Glu Ser Gly Thr Lys Leu Trp His
    1640                1645                1650
```

-continued

```
Leu Val Lys Asn His Asp His Leu Asp Gln Arg Glu Gly Asp Arg
    1655            1660                1665

Gly Ser Lys Met Val Ser Glu Ile Tyr Leu Thr Arg Leu Leu Ala
    1670            1675                1680

Thr Lys Gly Thr Leu Gln Lys Phe Val Asp Asp Leu Phe Glu Thr
    1685            1690                1695

Ile Phe Ser Thr Ala His Arg Gly Ser Ala Leu Pro Leu Ala Ile
    1700            1705                1710

Lys Tyr Met Phe Asp Phe Leu Asp Glu Gln Ala Asp Lys His Gln
    1715            1720                1725

Ile His Asp Ser Asp Val Arg His Thr Trp Lys Ser Asn Cys Leu
    1730            1735                1740

Pro Leu Arg Phe Trp Val Asn Val Ile Lys Asn Pro Gln Phe Val
    1745            1750                1755

Phe Asp Ile His Lys Asn Ser Ile Thr Asp Ala Cys Leu Ser Val
    1760            1765                1770

Val Ala Gln Thr Phe Met Asp Ser Cys Ser Thr Ser Glu His Lys
    1775            1780                1785

Leu Gly Lys Asp Ser Pro Ser Asn Lys Leu Leu Tyr Ala Lys Asp
    1790            1795                1800

Ile Pro Asn Tyr Lys Ser Trp Val Glu Arg Tyr Tyr Ala Asp Ile
    1805            1810                1815

Ala Lys Met Pro Ala Ile Ser Asp Gln Asp Met Ser Ala Tyr Leu
    1820            1825                1830

Ala Glu Gln Ser Arg Leu His Leu Ser Gln Phe Asn Ser Met Ser
    1835            1840                1845

Ala Leu His Glu Ile Tyr Ser Tyr Ile Ala Lys Tyr Lys Asp Glu
    1850            1855                1860

Ile Leu Val Ala Leu Glu Lys Asp Glu Gln Ala Arg Arg Gln Arg
    1865            1870                1875

Leu Arg Ser Lys Leu Glu Gln Val Val Asp Thr Met Ala Leu Ser
    1880            1885                1890

Ser
```

<210> SEQ ID NO 53
<211> LENGTH: 1894
<212> TYPE: PRT
<213> ORGANISM: Mus musculus

<400> SEQUENCE: 53

```
Met Glu Gln Arg Arg Phe Tyr Leu Arg Ala Met Gln Ala Asp Asn Leu
1               5                   10                  15

Ser Val Val Leu Leu Ser Val Ala Trp Leu Leu Leu Ala Arg Gly Thr
                20                  25                  30

Thr Gly Met Pro Gln Tyr Ser Thr Phe His Ser Glu Asn Arg Asp Trp
            35                  40                  45

Thr Phe Asn His Leu Thr Val His Arg Arg Thr Gly Ala Val Tyr Val
        50                  55                  60

Gly Ala Ile Asn Arg Val Tyr Lys Leu Thr Gly Asn Leu Thr Ile Gln
65                  70                  75                  80

Val Ala His Lys Thr Gly Pro Glu Glu Asp Asn Lys Ala Cys Tyr Pro
                85                  90                  95

Pro Leu Ile Val Gln Pro Cys Ser Glu Val Leu Thr Leu Thr Asn Asn
                100                 105                 110
```

```
Val Asn Lys Leu Leu Ile Ile Asp Tyr Ser Glu Asn Arg Leu Leu Ala
            115                 120                 125

Cys Gly Ser Leu Tyr Gln Gly Val Cys Lys Leu Leu Arg Leu Asp Asp
        130                 135                 140

Leu Phe Ile Leu Val Glu Pro Ser His Lys Lys Glu His Tyr Leu Ser
145                 150                 155                 160

Ser Val Asn Lys Thr Gly Thr Met Tyr Gly Val Ile Val Arg Ser Glu
                165                 170                 175

Gly Glu Asp Gly Lys Leu Phe Ile Gly Thr Ala Val Asp Gly Lys Gln
            180                 185                 190

Asp Tyr Phe Pro Thr Leu Ser Ser Arg Lys Leu Pro Arg Asp Pro Glu
        195                 200                 205

Ser Ser Ala Met Leu Asp Tyr Glu Leu His Ser Asp Phe Val Ser Ser
    210                 215                 220

Leu Ile Lys Ile Pro Ser Asp Thr Leu Ala Leu Val Ser His Phe Asp
225                 230                 235                 240

Ile Phe Tyr Ile Tyr Gly Phe Ala Ser Gly Gly Phe Val Tyr Phe Leu
                245                 250                 255

Thr Val Gln Pro Glu Thr Pro Asp Gly Met Ala Ile Asn Ser Ala Gly
            260                 265                 270

Asp Leu Phe Tyr Thr Ser Arg Ile Val Arg Leu Cys Lys Asp Asp Pro
        275                 280                 285

Lys Phe His Ser Tyr Val Ser Leu Pro Phe Gly Cys Thr Arg Ala Gly
    290                 295                 300

Val Glu Tyr Arg Leu Leu Gln Ala Ala Tyr Leu Ala Lys Pro Gly Glu
305                 310                 315                 320

Ala Leu Ala Gln Ala Phe Asn Ile Ser Ser Asp Glu Asp Val Leu Phe
                325                 330                 335

Ala Ile Phe Ser Lys Gly Gln Lys Gln Tyr His His Pro Pro Asp Asp
            340                 345                 350

Ser Ala Leu Cys Ala Phe Pro Ile Arg Ala Ile Asn Leu Gln Ile Lys
        355                 360                 365

Glu Arg Leu Gln Ser Cys Tyr His Gly Glu Gly Asn Leu Glu Leu Asn
    370                 375                 380

Trp Leu Leu Gly Lys Asp Val Gln Cys Thr Lys Ala Pro Val Pro Ile
385                 390                 395                 400

Asp Asp Asn Phe Cys Gly Leu Asp Ile Asn Gln Pro Leu Gly Gly Ser
                405                 410                 415

Thr Pro Val Glu Gly Leu Thr Leu Tyr Thr Thr Ser Arg Asp Arg Leu
            420                 425                 430

Thr Ser Val Ala Ser Tyr Val Tyr Asn Gly Tyr Ser Val Val Phe Val
        435                 440                 445

Gly Thr Lys Ser Gly Lys Leu Lys Lys Ile Arg Ala Asp Gly Pro Pro
    450                 455                 460

His Gly Gly Val Gln Tyr Glu Met Val Ser Val Phe Lys Asp Gly Ser
465                 470                 475                 480

Pro Ile Leu Arg Asp Met Ala Phe Ser Ile Asn Gln Leu Tyr Leu Tyr
                485                 490                 495

Val Met Ser Glu Arg Gln Val Thr Arg Val Pro Val Glu Ser Cys Glu
            500                 505                 510

Gln Tyr Thr Thr Cys Gly Glu Cys Leu Ser Ser Gly Asp Pro His Cys
        515                 520                 525
```

-continued

Gly Trp Cys Ala Leu His Asn Met Cys Ser Arg Arg Asp Lys Cys Gln
    530                 535                 540

Arg Ala Trp Glu Ala Asn Arg Phe Ala Ala Ser Ile Ser Gln Cys Met
545                 550                 555                 560

Ser Leu Glu Val His Pro Asn Ser Ile Ser Val Ser Asp His Ser Arg
                565                 570                 575

Leu Leu Ser Leu Val Asn Asp Ala Pro Asn Leu Ser Glu Gly Ile
            580                 585                 590

Ala Cys Ala Phe Gly Asn Leu Thr Glu Val Gly Gln Val Ser Gly
        595                 600                 605

Ser Gln Val Ile Cys Ile Ser Pro Gly Pro Lys Asp Val Pro Val Ile
    610                 615                 620

Pro Leu Asp Gln Asp Trp Phe Gly Leu Glu Leu Gln Leu Arg Ser Lys
625                 630                 635                 640

Glu Thr Gly Lys Ile Phe Val Ser Thr Glu Phe Lys Phe Tyr Asn Cys
                645                 650                 655

Ser Ala His Gln Leu Cys Leu Ser Cys Val Asn Ser Ala Phe Arg Cys
            660                 665                 670

His Trp Cys Lys Tyr Arg Asn Leu Cys Thr His Asp Pro Thr Thr Cys
        675                 680                 685

Ser Phe Gln Glu Gly Arg Ile Asn Val Ser Glu Asp Cys Pro Gln Leu
    690                 695                 700

Val Pro Thr Glu Glu Ile Leu Ile Pro Val Gly Glu Val Lys Pro Ile
705                 710                 715                 720

Thr Leu Lys Ala Arg Asn Leu Pro Gln Pro Gln Ser Gly Gln Arg Gly
                725                 730                 735

Tyr Glu Cys Val Leu Ser Ile Gln Gly Ala Val His Arg Val Pro Ala
            740                 745                 750

Leu Arg Phe Asn Ser Ser Val Gln Cys Gln Asn Ser Ser Tyr Gln
        755                 760                 765

Tyr Asp Gly Met Asp Ile Ser Asn Leu Ala Val Asp Phe Ala Val Val
    770                 775                 780

Trp Asn Gly Asn Phe Ile Ile Asp Asn Pro Gln Asp Leu Lys Val His
785                 790                 795                 800

Leu Tyr Lys Cys Ala Ala Gln Arg Glu Ser Cys Gly Leu Cys Leu Lys
                805                 810                 815

Ala Asp His Lys Phe Glu Cys Gly Trp Cys Ser Gly Glu Arg Arg Cys
            820                 825                 830

Thr Leu His Gln His Cys Pro Ser Thr Ser Ser Pro Trp Leu Asp Trp
        835                 840                 845

Ser Ser His Asn Val Lys Cys Ser Asn Pro Gln Ile Thr Glu Ile Leu
    850                 855                 860

Thr Val Ser Gly Pro Pro Glu Gly Gly Thr Arg Val Thr Ile His Gly
865                 870                 875                 880

Val Asn Leu Gly Leu Asp Phe Ser Glu Ile Ala His His Val Gln Val
                885                 890                 895

Ala Gly Val Pro Cys Thr Pro Ile Pro Gly Glu Tyr Ile Ile Ala Glu
            900                 905                 910

Gln Ile Val Cys Glu Met Gly His Ala Val Ile Gly Thr Thr Ser Gly
        915                 920                 925

Pro Val Arg Leu Cys Ile Gly Glu Cys Lys Pro Glu Phe Met Thr Lys
    930                 935                 940

Ser His Gln Gln Tyr Thr Phe Val Asn Pro Ser Val Leu Ser Leu Ser

-continued

```
           945                 950                 955                 960
Pro Ile Arg Gly Pro Glu Ser Gly Gly Thr Met Val Thr Ile Thr Gly
               965                 970                 975
His Tyr Leu Gly Ala Gly Ser Ser Val Ala Val Tyr Leu Gly Asn Gln
               980                 985                 990
Thr Cys Glu Phe Tyr Gly Arg Ser Met Asn Glu Ile Val Cys Val Ser
               995                 1000                1005
Pro Pro Ser Ser Asn Gly Leu Gly Pro Val Pro Val Ser Val Ser
    1010                1015                1020
Val Asp Arg Ala Arg Val Asp Ser Ser Leu Gln Phe Glu Tyr Ile
    1025                1030                1035
Asp Asp Pro Arg Val Gln Arg Ile Glu Pro Glu Trp Ser Ile Thr
    1040                1045                1050
Ser Gly His Thr Pro Leu Thr Ile Thr Gly Phe Asn Leu Asp Val
    1055                1060                1065
Ile Gln Glu Pro Arg Val Arg Val Lys Phe Asn Gly Lys Glu Ser
    1070                1075                1080
Val Asn Val Cys Thr Val Val Asn Thr Thr Thr Leu Thr Cys Leu
    1085                1090                1095
Ala Pro Ser Leu Thr Ser Asp Tyr Arg Pro Gly Leu Asp Thr Val
    1100                1105                1110
Glu Arg Pro Asp Glu Phe Gly Phe Leu Phe Asn Asn Val Gln Ser
    1115                1120                1125
Leu Leu Ile Tyr Asn Asp Thr Lys Phe Ile Tyr Tyr Pro Asn Pro
    1130                1135                1140
Thr Phe Glu Leu Leu Ser Pro Thr Gly Ile Leu Asp Gln Lys Pro
    1145                1150                1155
Gly Ser Pro Ile Ile Leu Lys Gly Lys Asn Leu Cys Pro Pro Ala
    1160                1165                1170
Ser Gly Gly Ala Lys Leu Asn Tyr Thr Val Met Ile Gly Glu Thr
    1175                1180                1185
Pro Cys Thr Val Thr Val Ser Glu Thr Gln Leu Leu Cys Glu Pro
    1190                1195                1200
Pro Asn Leu Thr Gly Gln His Lys Val Met Val His Val Gly Gly
    1205                1210                1215
Met Val Phe Ser Pro Gly Ser Val Ser Val Ile Ser Asp Ser Leu
    1220                1225                1230
Leu Thr Leu Pro Ala Ile Ile Ser Ile Ala Ala Gly Gly Ser Leu
    1235                1240                1245
Leu Leu Ile Ile Val Ile Ile Val Leu Ile Ala Tyr Lys Arg Lys
    1250                1255                1260
Ser Arg Glu Asn Asp Leu Thr Leu Lys Arg Leu Gln Met Gln Met
    1265                1270                1275
Asp Asn Leu Glu Ser Arg Val Ala Leu Glu Cys Lys Glu Ala Phe
    1280                1285                1290
Ala Glu Leu Gln Thr Asp Ile Asn Glu Leu Thr Ser Asp Leu Asp
    1295                1300                1305
Arg Ser Gly Ile Pro Tyr Leu Asp Tyr Arg Thr Tyr Ala Met Arg
    1310                1315                1320
Val Leu Phe Pro Gly Ile Glu Asp His Pro Val Leu Arg Glu Leu
    1325                1330                1335
Glu Val Gln Gly Asn Gly Gln Gln His Val Glu Lys Ala Leu Lys
    1340                1345                1350
```

-continued

```
Leu Phe Ala Gln Leu Ile Asn Asn Lys Val Phe Leu Leu Thr Phe
    1355                1360                1365
Ile Arg Thr Leu Glu Leu Gln Arg Ser Phe Ser Met Arg Asp Arg
    1370                1375                1380
Gly Asn Val Ala Ser Leu Ile Met Thr Gly Leu Gln Gly Arg Leu
    1385                1390                1395
Glu Tyr Ala Thr Asp Val Leu Lys Gln Leu Leu Ser Asp Leu Ile
    1400                1405                1410
Asp Lys Asn Leu Glu Asn Lys Asn His Pro Lys Leu Leu Leu Arg
    1415                1420                1425
Arg Thr Glu Ser Val Ala Glu Lys Met Leu Thr Asn Trp Phe Ala
    1430                1435                1440
Phe Leu Leu His Lys Phe Leu Lys Glu Cys Ala Gly Glu Pro Leu
    1445                1450                1455
Phe Met Leu Tyr Cys Ala Ile Lys Gln Gln Met Glu Lys Gly Pro
    1460                1465                1470
Ile Asp Ala Ile Thr Gly Glu Ala Arg Tyr Ser Leu Ser Glu Asp
    1475                1480                1485
Lys Leu Ile Arg Gln Gln Ile Glu Tyr Lys Thr Leu Ile Leu Asn
    1490                1495                1500
Cys Val Asn Pro Asp Asn Glu Asn Ser Pro Glu Ile Pro Val Lys
    1505                1510                1515
Val Leu Asn Cys Asp Thr Ile Thr Gln Val Lys Glu Lys Ile Leu
    1520                1525                1530
Asp Ala Val Tyr Lys Asn Val Pro Tyr Ser Gln Arg Pro Arg Ala
    1535                1540                1545
Val Asp Met Asp Leu Glu Trp Arg Gln Gly Arg Ile Ala Arg Val
    1550                1555                1560
Val Leu Gln Asp Glu Asp Ile Thr Thr Lys Ile Glu Gly Asp Trp
    1565                1570                1575
Lys Arg Leu Asn Thr Leu Met His Tyr Gln Val Ser Asp Arg Ser
    1580                1585                1590
Val Val Ala Leu Val Pro Lys Gln Thr Ser Ser Tyr Asn Ile Pro
    1595                1600                1605
Ala Ser Ala Ser Ile Ser Arg Thr Ser Ile Ser Arg Tyr Asp Ser
    1610                1615                1620
Ser Phe Arg Tyr Thr Gly Ser Pro Asp Ser Leu Arg Ser Arg Val
    1625                1630                1635
Pro Met Ile Thr Pro Asp Leu Glu Ser Gly Val Lys Val Trp His
    1640                1645                1650
Leu Val Lys Asn His Asp His Gly Asp Gln Lys Glu Gly Asp Arg
    1655                1660                1665
Gly Ser Lys Met Val Ser Glu Ile Tyr Leu Thr Arg Leu Leu Ala
    1670                1675                1680
Thr Lys Gly Thr Leu Gln Lys Phe Val Asp Asp Leu Phe Glu Thr
    1685                1690                1695
Leu Phe Ser Thr Val His Arg Gly Ser Ala Leu Pro Leu Ala Ile
    1700                1705                1710
Lys Tyr Met Phe Asp Phe Leu Asp Glu Gln Ala Asp Arg His Ser
    1715                1720                1725
Ile His Asp Thr Asp Val Arg His Thr Trp Lys Ser Asn Cys Leu
    1730                1735                1740
```

-continued

```
Pro Leu Arg Phe Trp Val Asn Val Ile Lys Asn Pro Gln Phe Val
    1745                1750                1755

Phe Asp Ile His Lys Gly Ser Ile Thr Asp Ala Cys Leu Ser Val
    1760                1765                1770

Val Ala Gln Thr Phe Met Asp Ser Cys Ser Thr Ser Glu His Arg
    1775                1780                1785

Leu Gly Lys Asp Ser Pro Ser Asn Lys Leu Leu Tyr Ala Lys Asp
    1790                1795                1800

Ile Pro Ser Tyr Lys Asn Trp Val Glu Arg Tyr Tyr Ala Asp Ile
    1805                1810                1815

Ala Lys Leu Pro Ala Ile Ser Asp Gln Asp Met Asn Ala Tyr Leu
    1820                1825                1830

Ala Glu Gln Ser Arg Leu His Ala Thr Glu Phe Asn Met Leu Ser
    1835                1840                1845

Ala Leu Asn Glu Ile Tyr Ser Tyr Val Ser Lys Tyr Ser Glu Glu
    1850                1855                1860

Leu Ile Gly Ala Leu Glu Gln Asp Glu Gln Ala Arg Arg Gln Arg
    1865                1870                1875

Leu Ala Tyr Lys Val Glu His Leu Ile Asn Ala Met Ser Ile Glu
    1880                1885                1890

Ser
```